US009585865B2

(12) United States Patent
Krohn et al.

(10) Patent No.: US 9,585,865 B2
(45) Date of Patent: Mar. 7, 2017

(54) SMALL MOLECULE MODULATORS OF THE COLD AND MENTHOL RECEPTOR TRPM8

(71) Applicant: B.R.A.I.N. Biotechnology Research and Information Network AG, Zwingenberg (DE)

(72) Inventors: Michael Krohn, Lorsch (DE); Holger Zinke, Heppenheim (DE)

(73) Assignee: B.R.A.I.N. Biotechnology Research and Information Network AG, Zwingenberg (DE)

( * ) Notice: Subject to any disclaimer, the term of this patent is extended or adjusted under 35 U.S.C. 154(b) by 0 days.

(21) Appl. No.: 14/563,793

(22) Filed: Dec. 8, 2014

(65) Prior Publication Data

US 2015/0094365 A1    Apr. 2, 2015

Related U.S. Application Data

(62) Division of application No. 14/003,762, filed as application No. PCT/EP2012/054046 on Mar. 8, 2012, now abandoned.

(30) Foreign Application Priority Data

Mar. 8, 2011 (EP) .................................... 11157329

(51) Int. Cl.
| | | |
|---|---|---|
| *A61K 31/35* | (2006.01) | |
| *A61K 31/352* | (2006.01) | |
| *A61K 8/41* | (2006.01) | |
| *A61K 8/49* | (2006.01) | |
| *A61K 31/00* | (2006.01) | |
| *A61K 31/136* | (2006.01) | |
| *A61K 31/137* | (2006.01) | |
| *A61K 31/351* | (2006.01) | |
| *A61K 31/4439* | (2006.01) | |
| *A61K 31/496* | (2006.01) | |
| *A61K 31/513* | (2006.01) | |
| *A61Q 5/00* | (2006.01) | |
| *A61Q 11/00* | (2006.01) | |
| *A61Q 17/02* | (2006.01) | |
| *A61Q 19/00* | (2006.01) | |
| *A61K 31/353* | (2006.01) | |
| *C07D 311/36* | (2006.01) | |

(52) U.S. Cl.
CPC .......... *A61K 31/352* (2013.01); *A23L 27/204* (2016.08); *A23L 27/2052* (2016.08); *A23L 27/2054* (2016.08); *A23L 27/2056* (2016.08); *A23L 27/88* (2016.08); *A61K 8/41* (2013.01); *A61K 8/411* (2013.01); *A61K 8/49* (2013.01); *A61K 8/498* (2013.01); *A61K 8/4933* (2013.01); *A61K 31/00* (2013.01); *A61K 31/136* (2013.01); *A61K 31/137* (2013.01); *A61K 31/351* (2013.01); *A61K 31/353* (2013.01); *A61K 31/4439* (2013.01); *A61K 31/496* (2013.01); *A61K 31/513* (2013.01); *A61Q 5/00* (2013.01); *A61Q 11/00* (2013.01); *A61Q 17/02* (2013.01); *A61Q 19/00* (2013.01); *C07D 311/36* (2013.01); *A23V 2002/00* (2013.01); *A61K 31/35* (2013.01); *A61K 2800/244* (2013.01); *A61K 2800/782* (2013.01); *Y10T 428/249921* (2015.04)

(58) Field of Classification Search
CPC ....... A61K 31/37; A61K 31/353; A61K 31/35
USPC ........................................................ 514/456
See application file for complete search history.

(56) References Cited

U.S. PATENT DOCUMENTS

| | | | |
|---|---|---|---|
| 3,178,442 | A | 4/1965 | Bencze |
| 4,166,862 | A | 9/1979 | Feuer et al. |
| 2006/0280697 | A1 | 12/2006 | Freunscht |
| 2013/0345300 | A1 | 12/2013 | Krohn et al. |

FOREIGN PATENT DOCUMENTS

| | | | |
|---|---|---|---|
| EP | 2168957 | A2 | 3/2010 |
| EP | 2186506 | A1 | 5/2010 |
| WO | 031092697 | A1 | 11/2003 |
| WO | 2004/026840 | A1 | 4/2004 |
| WO | 2005/121116 | A1 | 12/2005 |
| WO | 2006/092074 | A1 | 9/2006 |
| WO | 2008/015403 | A1 | 2/2008 |
| WO | 2008/138162 | A1 | 11/2008 |
| WO | 2010/017609 | A2 | 2/2010 |

(Continued)

OTHER PUBLICATIONS

International Search Report and Written Opinion received for PCT Patent Application No. PCT/EP2012/054046, mailed on Jun. 18, 2013, 26 pages.

(Continued)

*Primary Examiner* — Kevin E Weddington
(74) *Attorney, Agent, or Firm* — Morrison & Foerster LLP

(57) ABSTRACT

The present invention relates to the use of compounds which are capable of producing a cooling sensation when they are brought into contact with the human body. In particular, the present invention relates to the use of compounds modulating TRPM8, and optionally to the use of compounds selectively exhibiting agonist activity at the TRPM8 channel. Such compounds have applications in many fields, particularly in oral and personal hygiene products and foodstuffs, but also in pharmaceutical composition products, cosmetics, textile products and packaging products. The present invention further relates to products containing such compounds and to the medical use of such compounds.

9 Claims, 7 Drawing Sheets

(56) References Cited

FOREIGN PATENT DOCUMENTS

Figure 1:
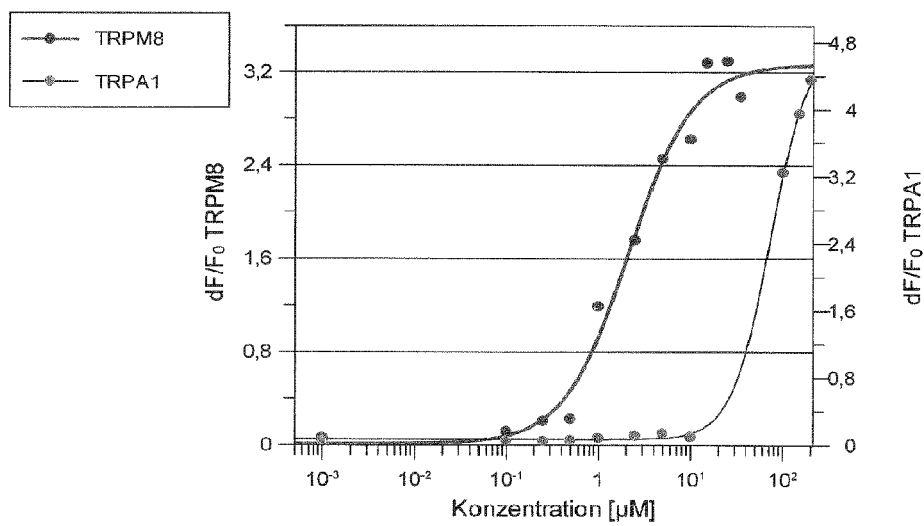
Figure 1:
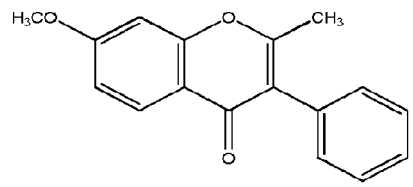

| WO | 2010/026094 A1 | 3/2010 | |
|---|---|---|---|
| WO | WO2012120099 A2 * | 9/2012 | ............... A61K 8/41 |

OTHER PUBLICATIONS

International Preliminary Report on Patentability received for PCT Patent Application No. PCT/EP2012/054046, mailed on Sep. 19, 2013, 17 pages.

European Search Report and Partial European Search Report received for European Patent Application No. 11157329.1, completed on Dec. 1, 2011, 18 pages.

Non Final Office Action received for U.S. Appl. No. 14/003,762, mailed on Sep. 8, 2014, 6 pages.

Anker et al., "Spectres De RMN Des Derives Benzopyroniques En Milieu Acide", Tetrahedron, vol. 25, 1969, pp. 5027-5045.

Antus et al., "Unusual Regioselectivity in the Reduction of α,β-Unsaturated Carbonyl Compounds with Diisobutylaluminum Hydride (DIBAH): Direct Conversion of Isoflavones to Isoflavan-4-ones", Synthesis, Jul. 1981, pp. 574-576.

Bandell et al., "Noxious Cold Ion Channel TRPA1 is Activated by Pungent Compounds and Bradykinin", Neuron, vol. 41, Mar. 25, 2004, pp. 849-857.

Behrendt et al., "Characterization of the Mouse Cold-Menthol Receptor TRPM8 and Vanilloid Receptor Type-1 VR1 using a Fluorometric Imaging Plate Reader (FLIPR) Assay", British Journal of Pharmacology, vol. 141, No. 4, 2004, pp. 737-745.

Furrer et al., "New Developments in the Chemistry of Cooling Compounds", Chemosensory Perception, vol. 1, Issue 2, 2008, pp. 119-126.

Genbank, Accession No. NM_007332, "*Homo sapiens* Transient Receptor Potential Cation Channel, Subfamily A, Member 1 (TRPA1), mRNA", available online at <www.ncbi.nlm.nih.gov/nuccorelNM_007332>, retrieved on Nov. 19, 2013, 8 pages.

Genbank, Accession No. NM_024080, "*Homo sapiens* Transient Receptor Potential Cation Channel, Subfamily M, Member 8 (TRPM8), mRNA", available online at <www.ncbi.nlm.nih.gov/nuccore/NM_024080#sequence_109689694>, retrieved on Nov. 19, 2013, 7 pages.

Jordt et al., "Mustard Oils and Cannabinoids Excite Sensory Nerve Fibres through the TRP Channel ANKTM1", Nature, vol. 427, Jan. 15, 2004, pp. 260-265.

Leffingwell, John C., "Cool without Menthol & Cooler than Menthol and Cooling Compounds as Insect Repellents", Leffingwell & Associates, availble online at <http://web.archive.org/web/20101203145738/http://leffingwell.com/cooler_than_menthol.htm> retrieved on Nov. 28, 2011, 19 pages.

Levai et al., "New Procedures for the Preparation of Isoflavones with Unsubstituted Ring A", ChemInform, 1992, 1 page.

Murti et al., "Insecticidal Properties and Chemical Constitution", Proceedings-Indian Academy of Sciences, Section A, vol. 27, 1948, pp. 33-36.

Ma et al., "Menthol Derivative WS-12 Selectively Activates Transient Receptor Potential Melastatin-8 (TRPM8) Ion Channels", Pakistan Journal of Pharmaceutical Sciences, vol. 21, No. 4, Oct. 2008, pp. 370-378.

McKemy et al., "Identification of a Cold Receptor Reveals a General Role for TRP Channels in Thermosensation", Nature, vol. 416, Mar. 7, 2002, pp. 52-58.

McKemy, David D., "How Cold is it? TRPM8 and TRPA1 in the Molecular Logic of Cold Sensation", Molecular Pain, vol. 1, No. 16, 2005, 7 pages.

Ortar et al., "(-)-Menthylamine Derivatives as Potent and Selective Antagonists of Transient Receptor Potential Melastatin Type-8 (TRPM8) Channels", Bioorganic & Medicinal Chemistry Letters, vol. 20, 2010, pp. 2729-2732.

Peier et al., "A TRP Channel that Senses Cold Stimuli and Menthol", Cell, vol. 108, Mar. 8, 2002, pp. 705-715.

Ross et al.,"Pharmacodynamics: Mechanisms of Drug Action and the Relationship Between Drug Concentration and Effect", Chapter 2 in Goodman and Gilman's The Pharmacological Basis of Therapeutics (Hardman and Limbird, 10 ed.), 2001, pp. 31-43.

Sherkheli et al., "Characterization of Selective TRPM8 Ligands and their Structure Activity Response (S.A.R) Relationship", Journal of Pharmacy & Pharmaceutical Sciences, vol. 13, No. 2, 2010, pp. 242-253.

Turov et al., "Use of Lanthanide Shift Reagents for Studying Pyridine Analogs of Isoflavones", Chemistry of Heterocyclic Compounds, vol. 34, No. 3, 1998, pp. 308-311.

Weil et al., "Conservation of Functional and Pharmacological Properties in the Distantly Related Temperature Sensors TRPV1 and TRPM8", Molecular Pharmacology, vol. 68, No. 2, 2005, pp. 518-527.

\* cited by examiner

SMALL MOLECULE MODULATORS OF THE COLD AND MENTHOL RECEPTOR TRPM8

CROSS REFERENCE TO RELATED APPLICATIONS

This application is a divisional of U.S. patent application Ser. No. 14/003,762, which is a U.S. National Phase Patent Application of PCT/EP2012/054046, filed on Mar. 8, 2012, which claims priority to European Patent Application No. 11157329.1, filed on Mar. 8, 2011, each of which is hereby incorporated by reference in the present disclosure in its entirety.

SUBJECT OF THE INVENTION

The present invention relates to the use of compounds which are capable of producing a cooling sensation when they are brought into contact with the human body. In particular, the present invention relates to the use of compounds modulating TRPM8, and optionally to the use of compounds selectively exhibiting agonist activity at the TRPM8 channel. Such compounds have applications in many fields, particularly in oral and personal hygiene products and foodstuffs, but also in pharmaceutical composition products, cosmetics, textile products and packaging products. The present invention further relates to products containing such compounds and to the medical use of such compounds.

BACKGROUND OF THE INVENTION

The transient receptor potential (TRP) ion channel family is a group of ion channels located mostly in the plasma membrane of numerous human and animal cell types. There are about 28 TRP channels that share some structural similarity to each other. Many of these channels mediate a variety of sensations like the sensations of pain, hotness, warmth or coldness, different kinds of tastes, pressure and vision. In the body, some TRP channels are thought to be involved in thermosensation and to be used in animals to sense hot or cold. Some TRP channels are activated by the pungent ingredients of spices like garlic, chilli pepper, wasabi; others are activated by menthol, camphor, peppermint, and cooling agents; yet others are activated by drugs like cannabinoids, e.g. marijuana. Some act as sensors of cellular stress such as osmotic pressure, volume, stretch, and vibration.

Six protein families are comprised by the mammalian TRP superfamily: the classic TRPs (TRPCs), the vanilloid receptor TRPs (TRPVs), the melastatin or long TRPs (TRPMs), the mucolipins (TRPMLs), the polycystins (TRPPs), and ankyrin transmembrane protein 1 (ANKTM1, TRPA1). With the exception of some polycystins, TRPs are generally assumed to have six transmembrane domains. The TRP channels are a family of ion channel proteins that mediate ion influx of $Na^+$ and $Ca^{2+}$ and, in several cases, $Mg^{2+}$ and other divalent cations. Since TRPs are intimately linked with intracellular $Ca^{2+}$ signaling, they are implicated in the control of cell cycle progression, cell migration, and programmed cell death.

The TRPM subfamily comprises eight members, including the cold and menthol receptor TRPM8, also designated as TRP melastatin 8, cold and menthol receptor 1 (CMR1) or transient receptor potential cation channel subfamily M member 8. In 2002, using divergent approaches, two scientific groups simultaneously identified and described TRPM8 (McKemy D D et al., Nature 2002, 416(6876):52-58; Peier A M et al., Cell 2002, 108(5):705-15). The channel is expressed, e.g., in small-diameter primary sensory neurones, where it presumably functions as a thermosensor. TRPM8 consists of six putative transmembrane spanning segments, a pore-forming loop and intracellularly located $NH_2$ and COOH termini. Assembly of channel subunits as tetramers results in the formation of cation-selective channels that permeate calcium ions. TRPM8 is involved in the detection of sensations such as coolness triggered, inter alia, by cooling agents and/or by cold (i.e. temperatures ranging from about 8° C. to about 28° C.).

Cooling agents are used extensively by flavor and fragrance suppliers in order to evoke associations with freshness and cleanliness. Hence, over the last 30 years a considerable number of compounds have been synthesized and evaluated for the physiological sensation of "cooling". For instance, the international patent application WO 2010/017609 discloses the use of the ingredients of *Mentha* and *Eucalyptus* oil as antiperspirants, the ingredients presumably acting as TRPM8 agonists. Furthermore, menthol, a cyclic terpene alcohol found in leaves of the genus *Mentha*, is used in a wide range of products, such as confectionary, candy, toothpastes, vaporubs, and aromatherapy inhalations. When applied at low concentrations to the skin or the oral mucosa, menthol elicits a pleasant cool sensation, while higher doses can cause burning, irritation, and pain.

It is known in the art that menthol can act as natural modulator of TRPM8 (McKemy D D et al., Nature 2002, 416(6876):52-58; Peier A M et al., Cell 2002, 108(5):705-15; McKemy D D, Molecular Pain 2005, 1:16). Upon activation, a signal transduction cascade is mediated by TRPM8, producing the perception of cold in the nervous system. For instance, activation of TRPM8 can induce an increase of intracellular calcium ions in cold-sensitive neurones. This calcium influx subsequently produces an inward current that provokes cold sensing.

In addition to menthol, a number of further cooling agents, including icilin (also designated as AG-3-5), CoolactP, Cooling Agent 10, FrescolatMGA, FrescolatML, geraniol, hydroxycitronellal, linalool, PMD38, WS-3, and WS-23 are known in the art to activate TRPM8 in vitro (McKemy D D et al., Nature 2002, 416(6876):52-58; Weil A et al., Mol. Pharmacol. 2005, 68(2):518-27; Behrendt H J et al., Br. J. Pharmacol. 2004, 141(4):737-45). Of these icilin, was first identified as a super-cooling agent in the early 1980s and bears little resemblance to menthol structurally (WO 2004/026840).

A number of methanol derivatives or other cooling agents which may exhibit a similar action at TRPM8 are known in the art. For instance, the international patent application WO 2010/026094 relates to modulators of TRPM8, to a method of modulating the TRPM8 channel, to the use of the modulators for induction of cold sensation and to the objects and means produced using said modulators. High concentrations of menthol can trigger other ion channels (e.g. TRPA1), presumably leading to these unpleasant sensations through activation of nociceptive sensory neurons (see e.g. review by McKemy D D, Mol. Pain 2005, 1:16). In addition menthol has a typical flavour and aroma which sometimes is disadvantageous for industrial applications in the food and cosmetic industry. Hence, there is a need for compounds which selectively modulate TRPM8, e.g. compounds which exhibit distinct activation concentrations at TRPM8 and TRPA1.

TRPA1 is a member of the TRPA branch of the TRP ion channel gene family. TRPA1 was identified as a potential mediator of noxious cold stimuli in nociceptive sensory neurons. Moreover, recent studies found evidence that TRPA1 is involved in sensory neural responses to mustard oil, allicin, and other chemical irritants (Jordt S E et al., Nature 2004, 427(6971):260-65; Bandell M et al., Neuron. 2004, 41(6):849-57). Hence, TRPA1 channels respond to a multitude of irritants with diverse origins and chemical structures, leading to, amongst others, sensations of pain, coughing, apnea, and lachrymation.

Some of the above-mentioned cooling agents have cooling effects at least to some extents, but may be insufficient and unsatisfactory in the retainability of the cooling effect. Hence, there is a strong demand in the art for providing cooling agents that have an improved sensory stimulating effect. Furthermore, some of the cooling agents known in the art may be insufficient with regard to their efficacy, their period of action, their scent, their taste, their solubility, and/or their volatility, and/or may cause irritation of the mucous membranes, itching of skin, tearing and/or the urge to cough. Accordingly, there is a need for alternative cooling agents that may overcome one or more of these drawbacks.

OBJECT AND SUMMARY OF THE INVENTION

It is an object of the invention to provide compounds that modulate the TRPM8 channel activity. In certain embodiments of the invention, such compounds exhibit agonist activity at the TRPM8 channel. In certain embodiments of the invention, such compounds exhibit partial agonist activity at the TRPM8 channel. In certain embodiments of the invention, such compounds exhibit selective agonist activity at the TRPM8 channel. In certain embodiments of the invention, such compounds exhibit antagonistic activity at the TRPM8 channel. In certain embodiments of the invention, such compounds exhibit partial antagonistic activity at the TRPM8 channel. In certain embodiments of the invention, such compounds exhibit selective antagonistic activity at the TRPM8 channel.

In certain embodiments of the invention, such compounds exhibit activity for activating TRPM8 in a lower concentration range than needed for activating TRPA1. In another embodiment, a compound of the invention acts as a TRPM8 agonist, but not as a TRPA1 agonist. In another embodiment, a compound of the invention acts as a TRPM8 partial agonist, but not as a TRPA1 agonist.

It is a further object of the invention to provide compounds which are excellent in evocation of cool and/or refreshing feeling or chilly and refreshing feeling without giving undesirable stimulation, peculiar odor, stinging, pungent or burning sensations and/or bitter taste, and which are usable as cooling agents and/or sensory stimulation agents. It is a further object of the invention to provide compounds which selectively modulate the cold and menthol receptor TRPM8. It is also an object of the invention to provide selective agonists of the cold and menthol receptor TRPM8. It is a further object of the invention to provide compounds which modulate the cold and menthol receptor TRPM8, but do not substantially trigger TRPA1, or at least to a lesser extent.

Also, the object of the invention is to provide cooling agent compositions comprising one or more of said compounds. Further, the object of the invention is to provide fragrance compositions, beverage or food products, cosmetic products, toiletry products, bathing agents, textile products, packaging products or pharmaceutical products comprising one or more of said compounds.

These objectives as well as others which will become apparent from the ensuing description are attained by the subject matter of the independent claims. Some of the embodiments of the present invention are defined by the subject matter of the dependent claims.

In one embodiment, the present invention relates to a product comprising a compound that selectively modulates TRPM8, and wherein the product is selected from the group consisting of a cosmetic product composition, a food product composition, a textile product, a pharmaceutical product composition and a packaging product.

According to an optional embodiment, the compound exhibits selective agonist activity at TRPM8.

According to a further optional embodiment, the compound exhibits activity at TRPM8, which activity is at least three times or even at least four times, greater than the activity of the compound at TRPA1.

According to a further optional embodiment, in a functional cell based assay the compound modulates the intracellular calcium level of human cells recombinantly expressing human TRPM8 at least four times more efficient than that of human cells recombinantly expressing human TRPA1.

Optionally, the compound is selected from the group consisting of Compounds I.1, II.1, III.1, IV.1, V.1, VI.1, and VII.1, the Compounds having the chemical structures as described hereinafter.

Optionally, the compound is selected from the group consisting of Compounds I.2, II.2, III.2, IV.2, V.2, VI.2, and VII.2, the Compounds having the chemical structures as described hereinafter.

Optionally, the compound is selected from the group consisting of Compounds I.3, II.3, III.3, IV.3, V.3, VI.3, and VII.3, the Compounds having the following chemical structures:

| Compound | Chemical structure |
|---|---|
| I.3 | 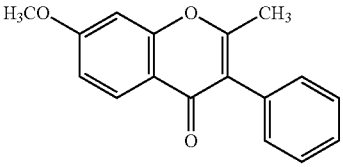 [SMILES: COc1ccc2c(=O)c(-c3ccccc3)c(C)oc2c1] |

| Compound | Chemical structure |
|---|---|
| II.3 | 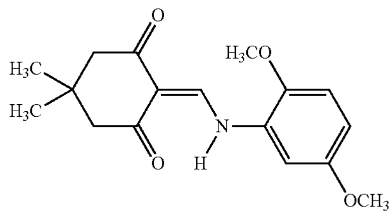 [SMILES: COc1ccc(OC)c(NC=C2C(=O)CC(C)(C)CC2=O)c1] |
| III.3 | 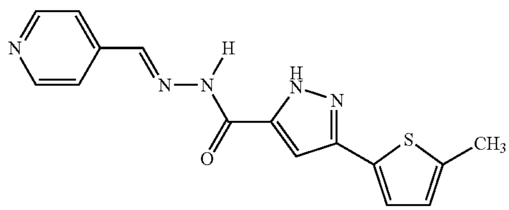 [SMILES: Cc1ccc(-c2cc(C(=O)N/N=C/c3ccncc3)[nH]n2)s1] |
| IV.3 | 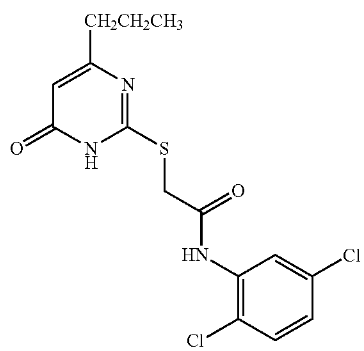 |
| V.3 | 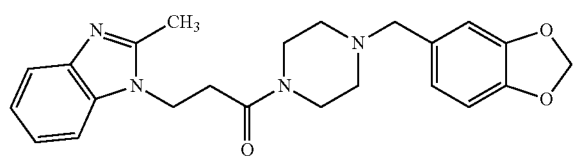 [SMILES: Cc1nc2ccccc2n1CCC(=O)N1CCN(Cc2ccc3c(c2)OCO3)CC1] |
| VI.3 | 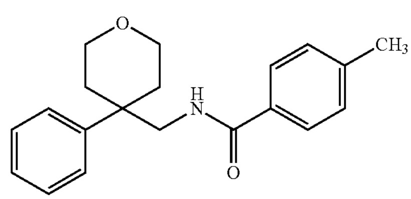 [SMILES: Cc1ccc(C(=O)NCC2(c3ccccc3)CCOCC2)cc1] |
| VII.3 | 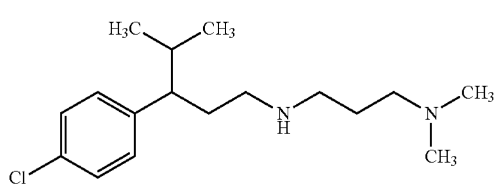 [SMILES: CC(C)C(CCNCCCN(C)C)c1ccc(Cl)cc1] |

In one further embodiment, the present invention relates to the use of a compound as defined in any of claims 1 to 6 and/or as described hereinafter in a product selected from the group consisting of a cosmetic product composition, a food product composition, a textile product, a pharmaceutical product composition, and a packaging product.

According to an optional embodiment, the cosmetic product composition is selected from the group consisting of an insect repellent composition, an oral hygiene composition, a skin care composition, and a hair care composition.

According to an optional embodiment, the food product composition is selected from the group consisting of ice cream, mousse, crème, beverages and confectionery.

According to an optional embodiment, the textile product is selected from the group consisting of shirts, trousers, socks, towels, headgear, underwear and shoes.

According to an optional embodiment, the pharmaceutical product composition is selected from the group consisting of anticancer medicaments, medicaments for the treatment of bladder diseases, and medicaments for the treatment of pain.

In one further embodiment, the present invention relates to a compound as defined in any of claims 1 to 6 and/or as described hereinafter for use in therapy.

In one further embodiment, the present invention relates to a compound as defined in any of claims 1 to 6 and/or as described hereinafter for use in the treatment of pain.

In one further embodiment, the present invention relates to a cosmetic use of a compound as defined in any of claims 1 to 6 and/or as described hereinafter as cooling agent.

In one further embodiment, the present invention relates to an in vitro method of modulating the cold and menthol receptor TRPM8, wherein TRPM8 is contacted with a compound as defined in any of claims 1 to 6 and/or as described hereinafter.

FIGURE LEGENDS

The accompanying drawings, which are incorporated and form part of the specification, merely illustrate certain embodiments of the present invention. They are meant to serve to explain specific modes of the present invention to those of skilled in the art. In the drawings:

FIG. 1 depicts a comparison of the $EC_{50}$ value of Compound I.3 acting as activator of TRPM8 with the $EC_{50}$ value of Compound I.3 acting as activator of TRPA1, as well as the chemical structure of Compound I.3. $EC_{50}$ of Compound I.3 acting as activator of TRPM8 is about 2.01 µM. $EC_{50}$ of Compound I.3 acting as activator of TRPA1 is about 72.42 µM. Hence, $EC_{50}$ of Compound I.3 acting as activator of TRPM8 is about 36 times lower than $EC_{50}$ of Compound I.3 acting as activator of TRPA1. The efficacy of Compound I.3 with respect to activation of TRPM8 has been evaluated to be about 110.06% (compared to 20 µM menthol).

Figure 2:
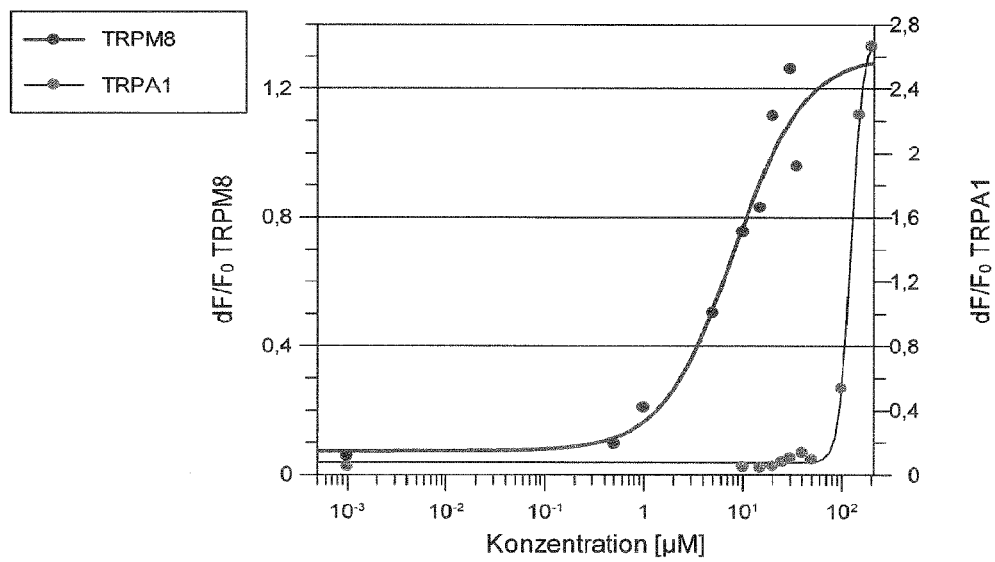
Figure 2:
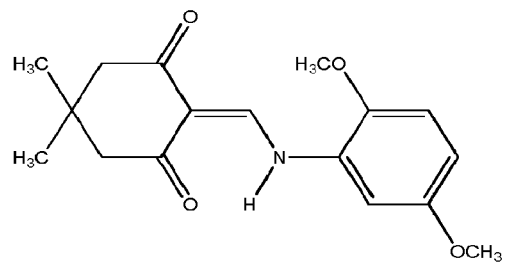

FIG. 2 depicts a comparison of the $EC_{50}$ value of Compound II.3 acting as activator of TRPM8 with the $EC_{50}$ value of Compound II.3 acting as activator of TRPA1, as well as the chemical structure of Compound II.3. $EC_{50}$ of Compound II.3 acting as activator of TRPM8 is about 8.01 µM. $EC_{50}$ of Compound II.3 acting as activator of TRPA1 is about 123.22 µM. Hence, $EC_{50}$ of Compound II.3 acting as activator of TRPM8 is about 15.4 times lower than $EC_{50}$ of Compound II.3 acting as activator of TRPA1. The efficacy of Compound II.3 with respect to activation of TRPM8 has been evaluated to be about 46.59% (compared to 20 µM menthol).

Figure 3:
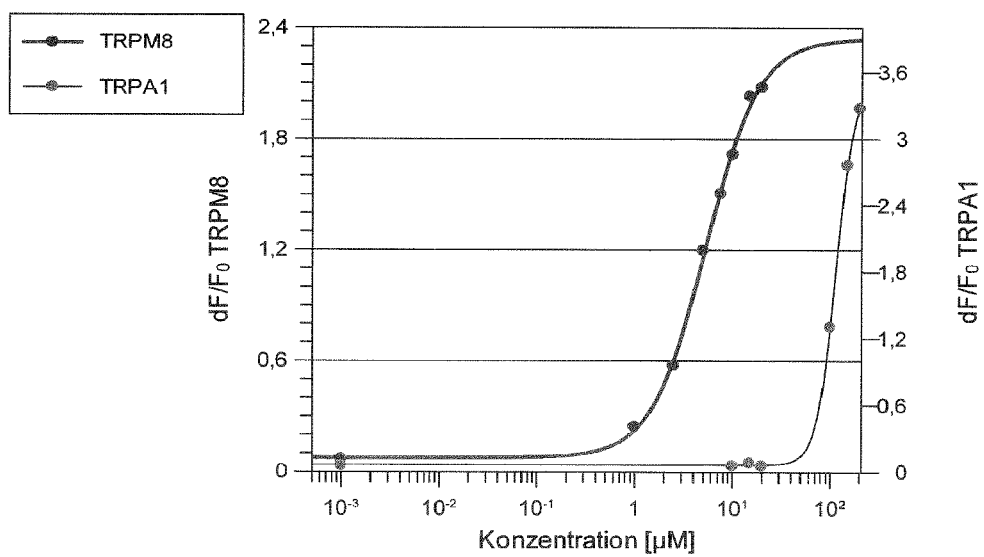
Figure 3:
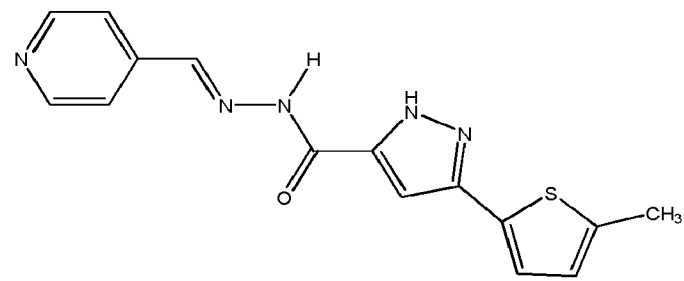

FIG. 3 depicts a comparison of the $EC_{50}$ value of Compound III.3 acting as activator of TRPM8 with the $EC_{50}$ value of Compound III.3 acting as activator of TRPA1, as well as the chemical structure of Compound III.3. $EC_{50}$ of Compound III.3 acting as activator of TRPM8 is about 5.27 µM. $EC_{50}$ of Compound III.3 acting as activator of TRPA1 is about 113.40 µM. Hence, $EC_{50}$ of Compound III.3 acting as activator of TRPM8 is about 21.5 times lower than $EC_{50}$ of Compound III.3 acting as activator of TRPA1. The efficacy of Compound III.3 with respect to activation of TRPM8 has been evaluated to be about 97.65% (compared to 20 µM menthol).

Figure 4:
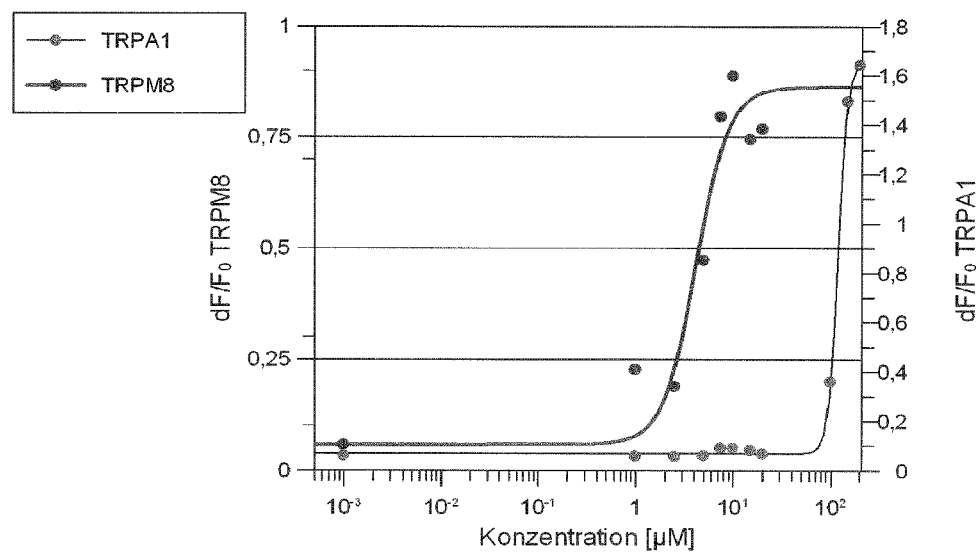
Figure 4:
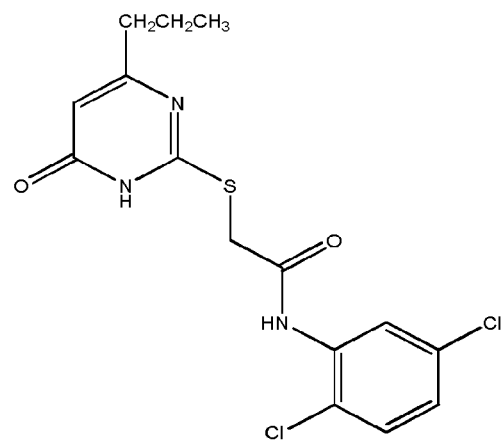

FIG. 4 depicts a comparison of the $EC_{50}$ value of Compound IV.3 acting as activator of TRPM8 with the $EC_{50}$ value of Compound IV.3 acting as activator of TRPA1, as well as the chemical structure of Compound IV.3. $EC_{50}$ of Compound IV.3 acting as activator of TRPM8 is about 4.12 µM. $EC_{50}$ of Compound IV.3 acting as activator of TRPA1 is about 117.89 µM. Hence, $EC_{50}$ of Compound IV.3 acting as activator of TRPM8 is about 28.6 times lower than $EC_{50}$ of Compound IV.3 acting as activator of TRPA1. The efficacy of Compound IV.3 with respect to activation of TRPM8 has been evaluated to be about 34.14% (compared to 20 µM menthol).

Figure 5:
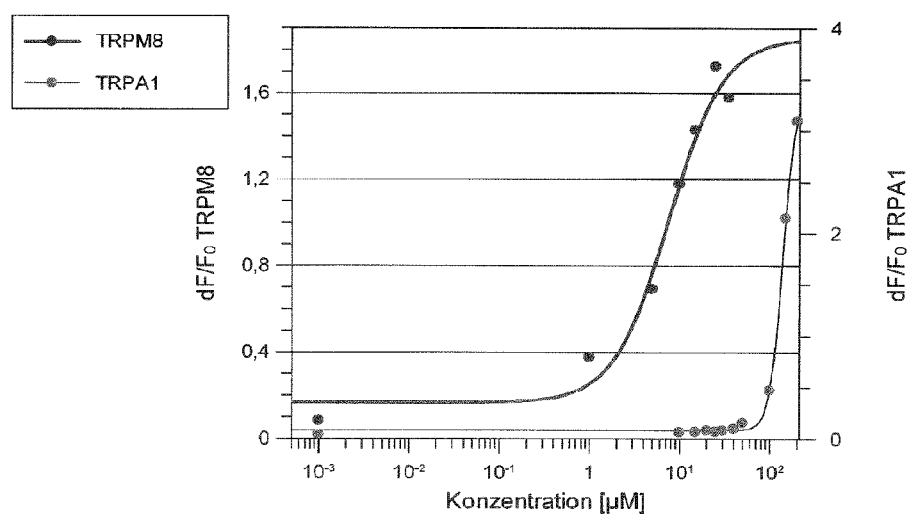
Figure 5:
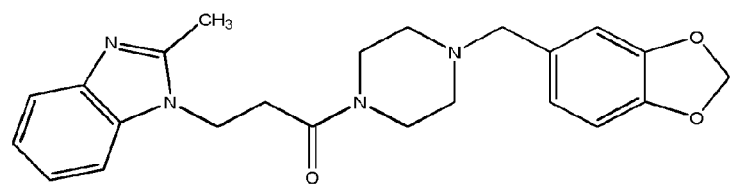

FIG. 5 depicts a comparison of the $EC_{50}$ value of Compound V.3 acting as activator of TRPM8 with the $EC_{50}$ value of Compound V.3 acting as activator of TRPA1, as well as the chemical structure of Compound V.3. $EC_{50}$ of Compound V.3 acting as activator of TRPM8 is about 7.53 µM. $EC_{50}$ of Compound V.3 acting as activator of TRPA1 is about 138.37 µM. Hence, $EC_{50}$ of Compound V.3 acting as activator of TRPM8 is about 18.4 times lower than $EC_{50}$ of Compound V.3 acting as activator of TRPA1. The efficacy of Compound V.3 with respect to activation of TRPM8 has been evaluated to be about 70.90% (compared to 20 µM menthol).

Figure 6:
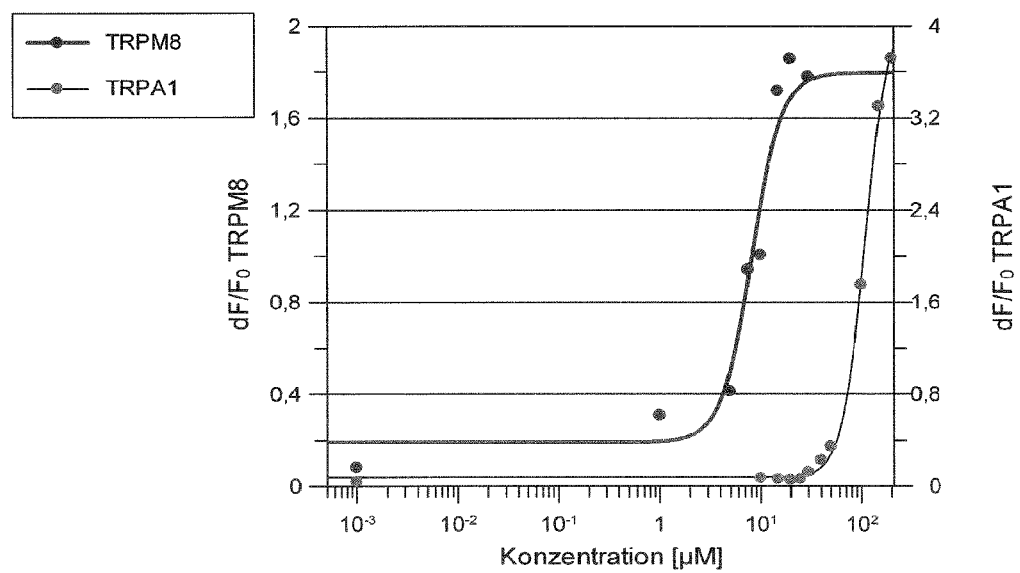
Figure 6:
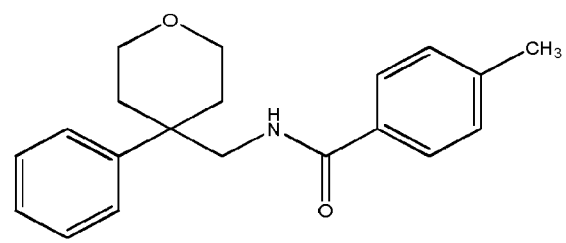

FIG. 6 depicts a comparison of the $EC_{50}$ value of Compound VI.3 acting as activator of TRPM8 with the $EC_{50}$ value of Compound VI.3 acting as activator of TRPA1, as well as the chemical structure of Compound VI.3. $EC_{50}$ of Compound VI.3 acting as activator of TRPM8 is about 8.15 µM. $EC_{50}$ of Compound VI.3 acting as activator of TRPA1 is about 107.64 µM. Hence, $EC_{50}$ of Compound VI.3 acting as activator of TRPM8 is about 13.2 times lower than $EC_{50}$ of Compound VI.3 acting as activator of TRPA1. The efficacy of Compound VI.3 with respect to activation of TRPM8 has been evaluated to be about 95.36% (compared to 20 µM menthol).

Figure 7:
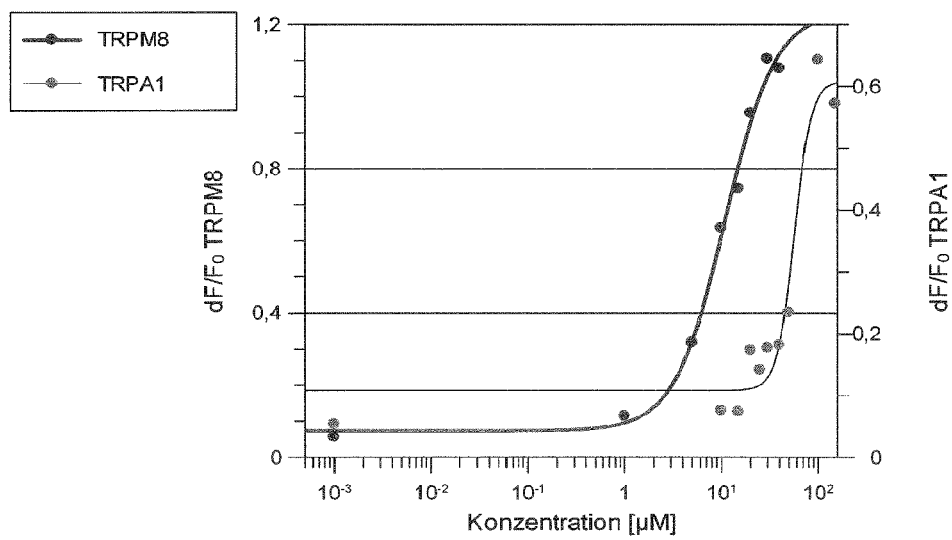
Figure 7:
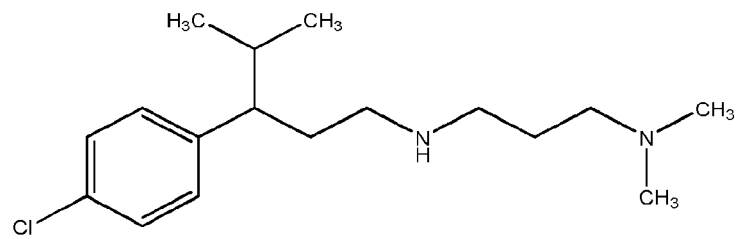

FIG. 7 depicts a comparison of the $EC_{50}$ value of Compound VII.3 acting as activator of TRPM8 with the $EC_{50}$ value of Compound VII.3 acting as activator of TRPA1, as well as the chemical structure of Compound VII.3. $EC_{50}$ of Compound VII.3 acting as activator of TRPM8 is about 10.94 µM. $EC_{50}$ of Compound VII.3 acting as activator of TRPA1 is about 56.62 µM. Hence, $EC_{50}$ of Compound VII.3 acting as activator of TRPM8 is about 5.2 times lower than $EC_{50}$ of Compound VII.3 acting as activator of TRPA1. The efficacy of Compound VII.3 with respect to activation of TRPM8 has been evaluated to be about 45.12% (compared to 20 µM menthol).

DETAILED DESCRIPTION OF THE INVENTION

The present invention illustratively described in the following may suitably be practiced in the absence of any element or elements, limitation or limitations, not specifically disclosed herein.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

Where the term "comprising" is used in the present description and claims, it does not exclude other elements or steps. For the purposes of the present invention, the term "consisting of" is considered to be a preferred embodiment of the term "comprising of". If hereinafter a group is defined to comprise at least a certain number of embodiments, this is also to be understood to disclose a group which optionally consists only of these embodiments.

Where an indefinite or definite article is used when referring to a singular noun e.g. "a" or "an", "the", this includes a plural of that noun unless something else is specifically stated.

The term "about" in the context of the present invention denotes an interval of accuracy that the person skilled in the art will understand to still ensure the technical effect of the feature in question. The term typically indicates deviation from the indicated numerical value of ±10%, and optionally ±5%.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Further definitions of term will be given in the following in the context of which the terms are used.

Compounds

In one embodiment, the present invention relates to a compound having the following general formula (I):

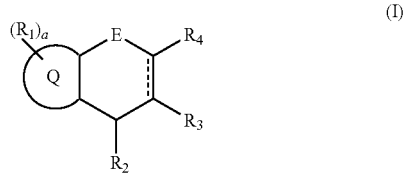

(I)

or a pharmaceutically acceptable derivative thereof wherein:
Q is selected from fused benzo or (5- or 6-membered) heteroaryl;
each $R_1$ is independently selected from:
(a) -halo, —CN, —$NO_2$; or
(b) —$OT_3$, —OC(=O)$T_3$, —OC(=O)N($T_1$)($T_2$), —OC(=O)O$T_3$; or
(c) —C(=O)$T_3$, —C(=O)O$T_3$, —C(=O)N($T_1$)($T_2$); or
(d) —S$T_3$, —S(=O)$T_3$, —S(=O)$_2T_3$, —S(=O)$_2$O$T_3$, —S(=O)$_2$N($T_1$)($T_2$), —S(=O)O$T_3$, —S(=O)N($T_1$)($T_2$); or
(e) —N($T_1$)($T_2$), —N($T_3$)N($T_1$)($T_2$), —N($T_3$)C(=O)$T_3$, —N($T_3$)C(=O)O$T_3$, —N($T_3$)C(=O)N($T_1$)($T_2$), —N($T_3$)S(=O)$_2T_3$, —N($T_3$)S(=O)$_2$N($T_1$)($T_2$), —N($T_3$)S(=O)$T_3$, —N($T_3$)S(=O)N($T_1$)($T_2$); or
(f) —($C_1$-$C_6$)alkyl, —($C_2$-$C_6$)alkenyl, —($C_2$-$C_6$)alkynyl, —($C_1$-$C_6$)alkoxy, —($C_3$-$C_7$)cycloalkyl, —($C_6$-$C_{14}$)bicycloalkyl, each of which is unsubstituted or substituted with 1, 2 or 3 independently selected $R_5$ groups; or
(g) -phenyl or -(5- or 6-membered)heteroaryl, each of which is unsubstituted or substituted with 1, 2 or 3 independently selected $R_6$ groups;
a is an integer selected from 0, 1, 2 or 3;
$R_2$ is selected from =O, =N$T_3$, =S, —O$T_3$, —OC(=O)$T_3$, —OC(=O)N($T_1$)($T_2$), —OC(=O)O$T_3$, —S$T_3$, —S(=O)$T_3$, —S(=O)$_2T_3$, —S(=O)$_2$O$T_3$, —S(=O)$_2$N($T_1$)($T_2$), —S(=O)O$T_3$, —S(=O)N($T_1$)($T_2$), —N($T_1$)($T_2$), —N($T_3$)N($T_1$)($T_2$), —N($T_3$)C(=O)$T_3$, —N($T_3$)C(=O)O$T_3$, —N($T_3$)C(=O)N($T_1$)($T_2$), —N($T_3$)S(=O)$_2T_3$, —N($T_3$)S(=O)$_2$N($T_1$)($T_2$), —N($T_3$)S(=O)$T_3$, or —N($T_3$)S(=O)N($T_1$)($T_2$);
$R_3$ and $R_4$ are each independently selected from:
(a) —H; or
(b) -halo, —CN, —$NO_2$; or
(c) —O$T_3$, —OC(=O)$T_3$, —OC(=O)N($T_1$)($T_2$), —OC(=O)O$T_3$; or
(d) —C(=O)$T_3$, —C(=O)O$T_3$, —C(=O)N($T_1$)($T_2$); or
(e) —S$T_3$, —S(=O)$T_3$, —S(=O)$_2T_3$, —S(=O)$_2$O$T_3$, —S(=O)$_2$N($T_1$)($T_2$), —S(=O)O$T_3$, —S(=O)N($T_1$)($T_2$); or
(f) —N($T_1$)($T_2$), —N($T_3$)N($T_1$)($T_2$), —N($T_3$)C(=O)$T_3$, —N($T_3$)C(=O)O$T_3$, —N($T_3$)C(=O)N($T_1$)($T_2$), —N($T_3$)S(=O)$_2T_3$, —N($T_3$)S(=O)$_2$N($T_1$)($T_2$), —N($T_3$)S(=O)$T_3$, —N($T_3$)S(=O)N($T_1$)($T_2$); or
(g) —($C_1$-$C_6$)alkyl, —($C_2$-$C_6$)alkenyl, —($C_2$-$C_6$)alkynyl, —($C_1$-$C_6$)alkoxy, —($C_3$-$C_7$)cycloalkyl, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(5- or 6-membered)heterocycle, or -(7- to 10-membered)bicycloheterocycle, each of which is unsubstituted or substituted with 1, 2 or 3 independently selected $R_5$ groups; or
(h) -phenyl or -(5- or 6-membered)heteroaryl, each of which is unsubstituted or substituted with 1, 2 or 3 independently selected $R_6$ groups;
E is selected from C($T_1$)($T_2$), O, S or N$T_3$;
each $R_5$ is independently selected from —($C_1$-$C_4$)alkyl, —($C_2$-$C_6$)alkenyl, —($C_2$-$C_6$)alkynyl, -(5- or 6-membered)heteroaryl, -phenyl, —($C_1$-$C_6$)alkylCOO$R_7$, —O$R_7$, —S$R_7$, —C(halo)$_3$, —CH(halo)$_2$, —$CH_2$(halo), —CN, =O, -halo, —$N_3$, —$NO_2$, —CH=N($R_7$), —N$R_7$($C_1$-$C_6$)alkylCOO$R_7$, —N($R_7$)$_2$, —N($R_7$)OH, —N($R_7$)S(=O)$R_8$, —N($R_7$)S(=O)$_2R_8$, —N($R_7$)C(=O)$R_8$, —N($R_7$)C(=O)N($R_7$)$_2$, —N($R_7$)C(=O)O$R_8$, —C(=O)$R_7$, —C(=O)—C(=O)O$R_7$, —C(=O)N($R_7$)$_2$, —C(=O)O$R_7$, —OC(=O)N($R_7$)$_2$, —OC(=O)O$R_7$, —S(=O)$R_7$, or —S(=O)$_2R_7$;
each $R_6$ is independently selected from —($C_1$-$C_4$)alkyl, —($C_2$-$C_6$)alkenyl, —($C_2$-$C_6$)alkynyl, —O$R_7$, —S$R_7$, —C(halo)$_3$, —CH(halo)$_2$, —$CH_2$(halo), —CN, -halo, —$N_3$, —$NO_2$, —CH=N($R_7$), —N($R_7$)$_2$, —N($R_7$)OH, —N($R_7$)S(=O)$R_8$, —N($R_7$)S(=O)$_2R_8$, —N($R_7$)C(=O)$R_8$, —N($R_7$)C(=O)N($R_7$)$_2$, —N($R_7$)C(=O)O$R_8$, —C(=O)$R_7$, —C(=O)N($R_7$)$_2$, —C(=O)O$R_7$, —OC(=O)$R_7$, —OC(=O)N($R_7$)$_2$, —OC(=O)O$R_7$, —S(=O)$R_7$, or —S(=O)$_2R_7$;
each $R_7$ is independently selected from —H, —($C_1$-$C_6$)alkyl, —($C_2$-$C_6$)alkenyl, —($C_2$-$C_6$)alkynyl, —($C_1$-$C_6$)alkoxy, —($C_3$-$C_8$)cycloalkyl, —($C_5$-$C_8$)cycloalkenyl, -phenyl, -benzyl, -(3- to 6-membered)heterocycle, -(5- to 10-membered)heteroaryl, —C(halo)$_3$, —CH(halo)$_2$, or —$CH_2$(halo);
each $R_8$ is independently selected from —H or —($C_1$-$C_4$)alkyl;
each $T_1$, $T_2$, and $T_3$ is independently —H or —($C_1$-$C_{10}$)alkyl which is unsubstituted or substituted with 1, 2 or 3 independently selected $R_5$ groups;
the dashed line in the 6-membered ring denotes the presence or absence of a bond; and
each halo is independently selected from —F, —Cl, —Br, or —I.

In a further embodiment, the present invention relates to a compound having the following general formula (I.1):

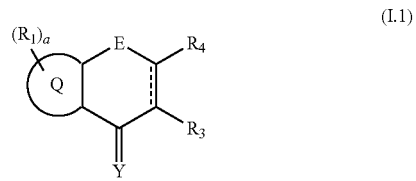

(I.1)

or a pharmaceutically acceptable derivative thereof wherein:
Q is selected from fused benzo or 6-membered heteroaryl;
each $R_1$ is independently selected from:
- (a) -halo, —CN, —NO$_2$; or
- (b) —OT$_3$, —OC(=O)T$_3$; or
- (c) —C(=O)T$_3$; or
- (d) —ST$_3$, —S(=O)T$_3$, —S(=O)$_2$T$_3$, —S(=O)$_2$OT$_3$; or
- (e) —(C$_1$-C$_4$)alkyl, —(C$_2$-C$_4$)alkenyl, —(C$_2$-C$_4$)alkynyl, —(C$_1$-C$_4$)alkoxy, each of which is unsubstituted or substituted with 1 or 2 independently selected $R_5$ groups;

a is an integer selected from 0, 1, or 2;
Y and E are each independently selected from O, S, or NT$_3$;
$R_3$ and $R_4$ are each independently selected from:
- (a) —H; or
- (b) —(C$_1$-C$_4$)alkyl, —(C$_2$-C$_4$)alkenyl, —(C$_2$-C$_4$)alkynyl, —(C$_1$-C$_4$)alkoxy, each of which is unsubstituted or substituted with 1 or 2 independently selected $R_5$ groups;
- (c) -phenyl or -(5- or 6-membered)heteroaryl containing 1 or 2 atoms selected from the group consisting of O, N and S, each of which is unsubstituted or substituted with 1 or 2 independently selected $R_6$ groups;

the dashed line in the 6-membered ring denotes the presence or absence of a bond;
each $R_5$ is independently selected from —(C$_1$-C$_3$)alkyl, —(C$_2$-C$_3$)alkenyl, —(C$_2$-C$_3$)alkynyl, —(C$_1$-C$_3$)alkyl-COOR$_7$, —OR$_7$, —SR$_7$, —C(halo)$_3$, —CH(halo)$_2$, —CH$_2$(halo), —CN, =O, =S, -halo, —N$_3$, —NO$_2$, —N(R$_7$)$_2$, —N(R$_7$)OH, —C(=O)R$_7$, —C(=O)OR$_7$, —OC(=O)R$_7$, —S(=O)R$_7$, or —S(=O)$_2$R$_7$;
each $R_6$ is independently selected from —(C$_1$-C$_3$)alkyl, —(C$_2$-C$_3$)alkenyl, —(C$_2$-C$_3$)alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)OR$_7$, —OC(=O)R$_7$, —S(=O)R$_7$, or —S(=O)$_2$R$_7$;
each $R_7$ is independently selected from —H, —CH$_3$, or —CH$_2$CH$_3$,
each $T_3$ is independently —H or —(C$_1$-C$_5$)alkyl which is unsubstituted or substituted with 1 or 2 independently selected $R_5$ groups; and
each halo is independently selected from —F, —Br, or —I.

In a further embodiment, the present invention relates to a compound having the following general formula (I.2):

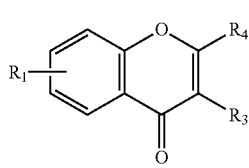
(I.2)

or a pharmaceutically acceptable derivative thereof wherein:
$R_1$ is selected from —H; —OT$_3$, —ST$_3$, or —(C$_1$-C$_3$)alkyl, wherein $T_3$ is selected from —H or —(C$_1$-C$_2$)alkyl;
$R_3$ is selected from -phenyl or -heteroaryl selected from the group consisting of pyridine, pyrazine, pyridazine and pyrimidine, each of which is unsubstituted or substituted with 1 or 2 independently selected $R_6$ groups;
$R_4$ is selected from —(C$_1$-C$_3$)alkyl, —(C$_2$-C$_3$)alkenyl, —(C$_2$-C$_3$)alkynyl, or —(C$_1$-C$_3$)alkoxy; and
$R_6$ is selected from —H, —(C$_1$-C$_2$)alkyl, —(C$_2$)alkenyl, —(C$_2$)alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)OR$_7$, —S(=O)R$_7$, or —S(=O)$_2$R$_7$;
each $R_7$ is independently selected from —H, or —CH$_3$; and
each halo is independently selected from —F, —Cl, —Br, or —I.

In an optional embodiment, the present invention relates to a compound having the general formula (I.2) or a pharmaceutically acceptable derivative thereof, wherein the fused benzo is substituted as follows:

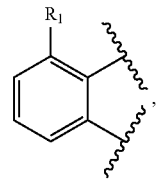

wherein $R_1$ is defined as above.

In an optional embodiment, the present invention relates to a compound having the general formula (I.2) or a pharmaceutically acceptable derivative thereof, wherein the fused benzo is substituted as follows:

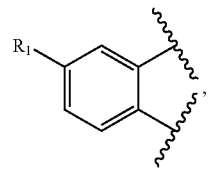

wherein $R_1$ is defined as above.

In an optional embodiment, the present invention relates to a compound having the general formula (I.2) or a pharmaceutically acceptable derivative thereof, wherein the fused benzo is substituted as follows:

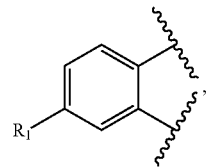

wherein $R_1$ is defined as above.

In an optional embodiment, the present invention relates to a compound having the general formula (I.2) or a pharmaceutically acceptable derivative thereof, wherein the fused benzo is substituted as follows:

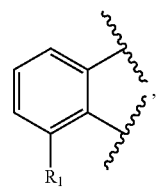

wherein $R_1$ is defined as above.

In an optional embodiment, the present invention relates to a compound having the general formula (I.2) or a pharmaceutically acceptable derivative thereof, wherein $R_1$ is selected from —H; —Cl, —OH, —OCH$_3$, —SH, —SCH$_3$ or —CH$_3$.

In an optional embodiment, the present invention relates to a compound having the general formula (I.2) or a pharmaceutically acceptable derivative thereof, wherein the fused benzo is substituted as follows:

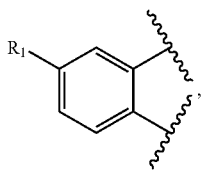

wherein $R_1$ is selected from —H; —OH, —OCH$_3$, or —CH$_3$.

In an optional embodiment, the present invention relates to a compound having the general formula (I.2) or a pharmaceutically acceptable derivative thereof, wherein $R_3$ is -phenyl, which is unsubstituted or substituted with 1 or 2 independently selected groups selected from —H, —CH$_3$, —OH, —SH, —OCH$_3$, and —Cl.

In an optional embodiment, the present invention relates to a compound having the general formula (I.2) or a pharmaceutically acceptable derivative thereof, wherein $R_3$ is -phenyl, which is unsubstituted.

In an optional embodiment, the present invention relates to a compound having the general formula (I.2) or a pharmaceutically acceptable derivative thereof, wherein $R_4$ is selected from —H, —CH$_3$, and —CH$_2$CH$_3$.

In an optional embodiment, the present invention relates to a compound having the general formula (I.2) or a pharmaceutically acceptable derivative thereof, wherein halo is Cl.

In a further embodiment, the present invention relates to a compound having the following general formula (II):

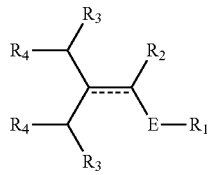

or a pharmaceutically acceptable derivative thereof wherein:
$R_1$ is selected from -phenyl or -(5- or 6-membered)heteroaryl, each of which is unsubstituted or substituted with 1, 2 or 3 independently selected $R_6$ groups;
$R_2$, each $R_3$ and each $R_4$ are each independently selected from:
  (a) —H; or
  (b) -halo, —CN, —NO$_2$; or
  (c) =O, —OT$_3$, —OC(=O)T$_3$, —OC(=O)N(T$_1$)(T$_2$), —OC(=O)OT$_3$; or
  (d) —C(=O)T$_3$, —C(=O)OT$_3$, —C(=O)N(T$_1$)(T$_2$); or
  (e) =S, —ST$_3$, —S(=O)T$_3$, —S(=O)$_2$T$_3$, —S(=O)$_2$OT$_3$, —S(=O)$_2$N(T$_1$)(T$_2$), —S(=O)OT$_3$, —S(=O)N(T$_1$)(T$_2$); or
  (f) =NT$_3$, —N(T$_1$)(T$_2$), —N(T$_3$)N(T$_1$)(T$_2$), —N(T$_3$)C(=O)T$_3$, —N(T$_3$)C(=O)OT$_3$, —N(T$_3$)C(=O)N(T$_1$)(T$_2$), —N(T$_3$)S(=O)$_2$T$_3$, —N(T$_3$)S(=O)$_2$N(T$_1$)(T$_2$), —N(T$_3$)S(=O)T$_3$, —N(T$_3$)S(=O)N(T$_1$)(T$_2$); or
  (g) —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(5- or 6-membered)heterocycle, or -(7- to 10-membered)bicycloheterocycle, each of which is unsubstituted or substituted with 1, 2 or 3 independently selected $R_5$ groups; or
  (h) -phenyl or -(5- or 6-membered)heteroaryl, each of which is unsubstituted or substituted with 1, 2 or 3 independently selected $R_6$ groups;
  wherein both $R_4$ can together form a (C$_2$-C$_6$)bridge, which is unsubstituted or substituted with 1, 2 or 3 independently selected $R_5$ groups;
E is selected from C(T$_1$)(T$_2$), O, S or NT$_3$;
each $R_5$ is independently selected from —(C$_1$-C$_4$)alkyl, —(C$_2$-C$_6$)alkenyl, —(C$_2$-C$_6$)alkynyl, -(5- or 6-membered)heteroaryl, -phenyl, —(C$_1$-C$_6$)alkylCOOR$_7$, —OR$_7$, —SR$_7$, —C(halo)$_3$, —CH(halo)$_2$, —CH$_2$(halo), —CN, =O, =S, -halo, —N$_3$, —NO$_2$, —CH=N(R$_7$), —NR$_7$(C$_1$-C$_6$)alkylCOOR$_7$, —N(R$_7$)$_2$, —N(R$_7$)OH, —N(R$_7$)S(=O)R$_8$, —N(R$_7$)S(=O)$_2$R$_8$, —N(R$_7$)C(=O)R$_8$, —N(R$_7$)C(=O)N(R$_7$)$_2$, —N(R$_7$)C(=O)OR$_8$, —C(=O)R$_7$, —C(=O)—C(=O)OR$_7$, —C(=O)N(R$_7$)$_2$, —C(=O)OR$_7$, —OC(=O)R$_7$, —OC(=O)N(R$_7$)$_2$, —OC(=O)OR$_7$, —S(=O)R$_7$, or —S(=O)$_2$R$_7$;
each $R_6$ is independently selected from —(C$_1$-C$_4$)alkyl, —(C$_2$-C$_6$)alkenyl, —(C$_2$-C$_6$)alkynyl, —OR$_7$, —SR$_7$, —C(halo)$_3$, —CH(halo)$_2$, —CH$_2$(halo), —CN, -halo, —N$_3$, —NO$_2$, —CH=N(R$_7$), —N(R$_7$)$_2$, —N(R$_7$)OH, —N(R$_7$)S(=O)R$_8$, —N(R$_7$)S(=O)$_2$R$_8$, —N(R$_7$)C(=O)R$_8$, —N(R$_7$)C(=O)N(R$_7$)$_2$, —N(R$_7$)C(=O)OR$_8$, —C(=O)R$_7$, —C(=O)N(R$_7$)$_2$, —C(=O)OR$_7$, —OC(=O)R$_7$, —OC(=O)N(R$_7$)$_2$, —OC(=O)OR$_7$, —S(=O)R$_7$, or —S(=O)$_2$R$_7$;
each $R_7$ is independently selected from —H, —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_8$)cycloalkyl, —(C$_5$-C$_8$)cycloalkenyl, -phenyl, -benzyl, -(3- to 6-membered)heterocycle, -(5- to 10-membered)heteroaryl, —C(halo)$_3$, —CH(halo)$_2$, or —CH$_2$(halo);
each $R_8$ is independently selected from —H or —(C$_1$-C$_4$)alkyl;
each $T_1$, $T_2$, and $T_3$ is independently is independently —H or —(C$_1$-C$_{10}$)alkyl which is unsubstituted or substituted with 1, 2 or 3 independently selected $R_5$ groups;
the dashed line denotes the presence or absence of a bond; and
each halo is independently selected from —F, —Cl, —Br, or —I.

In a further embodiment, the present invention relates to a compound having the following general formula (II.1):

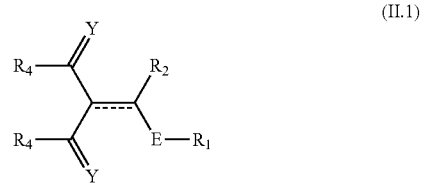

or a pharmaceutically acceptable derivative thereof wherein:
R₁ is selected from -phenyl or -(6-membered)heteroaryl, each of which is unsubstituted or substituted with 1, 2 or 3 independently selected $R_6$ groups;
$R_2$ and each $R_4$ are each independently selected from:
(a) —H; or
(b) -halo, —CN, —NO₂; or
(c) —OT₃, —OC(=O)T₃; or
(d) —C(=O)T₃; or
(e) —ST₃, —S(=O)T₃, —S(=O)₂T₃, —S(=O)₂OT₃; or
(f) —(C₁-C₅)alkyl, —(C₂-C₅)alkenyl, —(C₂-C₅)alkynyl, —(C₁-C₅)alkoxy, —(C₃-C₇)cycloalkyl, —(C₅-C₁₀)cycloalkenyl, or -(5- or 6-membered)heterocycle, each of which is unsubstituted or substituted with 1 or 2 independently selected $R_5$ groups;
wherein both $R_4$ can together form a (C₂-C₆)bridge, which is unsubstituted or substituted with 1 or 2 independently selected $R_5$ groups; or
E is selected from O, S or NT₃;
each Y is independently selected from O, S or NT₃;
each $R_5$ is independently selected from —(C₁-C₃)alkyl, —(C₂-C₃)alkenyl, —(C₂-C₃)alkynyl, —(C₁-C₃)alkyl-COOR₇, —OR₇, —SR₇, —C(halo)₃, —CH(halo)₂, —CH₂(halo), —CN, =O, =S, -halo, —N₃, —NO₂, —N(R₇)₂, —N(R₇)OH, —C(=O)R₇, —C(=O)OR₇, —OC(=O)R₇, —S(=O)R₇, or —S(=O)₂R₇;
each $R_6$ is independently selected from —(C₁-C₃)alkyl, —(C₂-C₃)alkenyl, —(C₂-C₃)alkynyl, —OR₇, —SR₇, —C(halo)₃, —CH(halo)₂, —CH₂(halo), —CN, -halo, —N₃, —NO₂, —N(R₇)₂, —N(R₇)OH, —C(=O)R₇, —C(=O)OR₇, —OC(=O)R₇, —S(=O)R₇, or —S(=O)₂R₇;
each $R_7$ is independently selected from —H, —CH₃, or —CH₂CH₃;
each T₃ is independently —H or —(C₁-C₅)alkyl which is unsubstituted or substituted with 1 or 2 independently selected $R_5$ groups;
the dashed line denotes the presence or absence of a bond; and
each halo is independently selected from —F, —Cl, —Br, or —I.

In a further embodiment, the present invention relates to a compound having the following general formula (II.2):

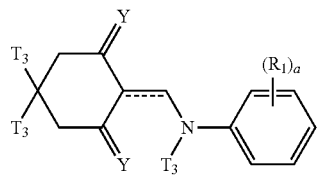

(II.2)

or a pharmaceutically acceptable derivative thereof wherein:
each $R_1$ is independently selected from —(C₁-C₂)alkyl, —(C₂)alkenyl, —(C₂)alkynyl, —OR₇, —SR₇, —C(halo)₃, —CH(halo)₂, —CH₂(halo), —CN, -halo, —N₃, —NO₂, —N(R₇)₂, —N(R₇)OH, —C(=O)R₇, —C(=O)OR₇, —S(=O)R₇, or —S(=O)₂R₇;
each $R_7$ is independently selected from —H, or —CH₃;
each halo is independently selected from —F, —Cl, —Br, or —I;
a is an integer selected from 1 or 2;
each T₃ is independently selected from —H or —(C₁-C₂)alkyl;
the dashed line denotes the presence or absence of a bond; and
each Y is independently selected from O, S or NT₃.

In an optional embodiment, the present invention relates to a compound having the general formula (II.2) or a pharmaceutically acceptable derivative thereof, wherein a is 2 and the phenyl group comprising —(R₁)ₐ is substituted as follows:

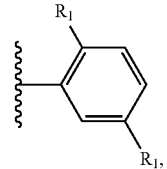

wherein $R_1$ is defined as above.

In an optional embodiment, the present invention relates to a compound having the general formula (II.2) or a pharmaceutically acceptable derivative thereof, wherein a is 2 and the phenyl group comprising —(R₁)ₐ is substituted as follows:

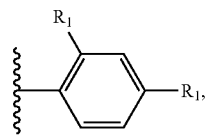

wherein $R_1$ is defined as above.

In an optional embodiment, the present invention relates to a compound having the general formula (II.2) or a pharmaceutically acceptable derivative thereof, wherein a=2 and each $R_1$ is independently selected from —H; —OH, —Cl, —OCH₃, —SH, —SCH₃ or —CH₃.

In an optional embodiment, the present invention relates to a compound having the general formula (II.2) or a pharmaceutically acceptable derivative thereof, wherein a=1 and $R_1$ is selected from —H; —OH, Cl, —OCH₃, —SH, —SCH₃ or —CH₃.

In an optional embodiment, the present invention relates to a compound having the general formula (II.2) or a pharmaceutically acceptable derivative thereof, wherein a is 2 and the phenyl group comprising —(R₁)ₐ is substituted as follows:

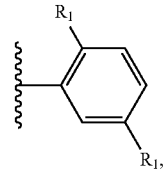

wherein each $R_1$ is independently selected from —H; —OH, —OCH₃, —SH, —SCH₃, —Cl or —CH₃.

In an optional embodiment, the present invention relates to a compound having the general formula (II.2) or a pharmaceutically acceptable derivative thereof, wherein each T₃ is independently selected from —H or —CH₃.

In an optional embodiment, the present invention relates to a compound having the general formula (II.2) or a pharmaceutically acceptable derivative thereof, wherein the dashed line denotes the presence of a bond.

In an optional embodiment, the present invention relates to a compound having the general formula (II.2) or a pharmaceutically acceptable derivative thereof, wherein each Y is O.

In a further embodiment, the present invention relates to a compound having the following general formula (III):

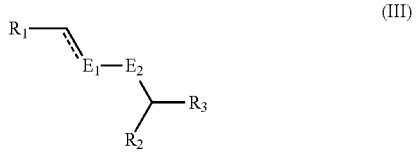

(III)

or a pharmaceutically acceptable derivative thereof wherein:
$R_1$ is selected from:
(a) —$(C_3-C_7)$cycloalkyl, —$(C_6-C_{14})$bicycloalkyl, —$(C_8-C_{20})$tricycloalkyl, —$(C_5-C_{10})$cycloalkenyl, —$(C_7-C_{14})$bicycloalkenyl, —$(C_8-C_{20})$tricycloalkenyl, -(5- or 6-membered)heterocycle, or -(7- to 10-membered)bicycloheterocycle, each of which is unsubstituted or substituted with 1, 2 or 3 independently selected $R_5$ groups; or
(b) -phenyl, -naphthalenyl, —$(C_{14})$aryl, or -(5- or 6-membered)heteroaryl, each of which is unsubstituted or substituted with 1, 2 or 3 independently selected $R_6$ groups;

$R_2$ is selected from =O, =$NT_3$, =S, —$OT_3$, —$OC(=O)T_3$, —$OC(=O)N(T_1)(T_2)$, —$OC(=O)OT_3$, —$ST_3$, —$S(=O)T_3$, —$S(=O)_2T_3$, —$S(=O)_2OT_3$, —$S(=O)_2N(T_1)(T_2)$, —$S(=O)OT_3$, —$S(=O)N(T_1)(T_2)$, —$N(T_1)(T_2)$, —$N(T_3)N(T_1)(T_2)$, —$N(T_3)C(=O)T_3$, —$N(T_3)C(=O)OT_3$, —$N(T_3)C(=O)N(T_1)(T_2)$, —$N(T_3)S(=O)_2T_3$, —$N(T_3)S(=O)_2N(T_1)(T_2)$, —$N(T_3)S(=O)T_3$, or —$N(T_3)S(=O)N(T_1)(T_2)$;

$R_3$ is selected from:
(a) —$(C_3-C_7)$cycloalkyl, —$(C_6-C_{14})$bicycloalkyl, —$(C_8-C_{20})$tricycloalkyl, —$(C_5-C_{10})$cycloalkenyl, —$(C_7-C_{14})$bicycloalkenyl, —$(C_8-C_{20})$tricycloalkenyl, -(5- or 6-membered)heterocycle, or -(7- to 10-membered)bicycloheterocycle, each of which is substituted with 1 or 2 independently selected $R_4$ groups; or
(b) -phenyl, -naphthalenyl, —$(C_{14})$aryl, or -(5- or 6-membered)heteroaryl, each of which is substituted with 1 or 2 independently selected $R_4$ groups;

each $R_4$ is independently selected from:
(a) —$(C_3-C_7)$cycloalkyl, —$(C_5-C_{10})$cycloalkenyl, or -(5- or 6-membered)heterocycle, each of which is unsubstituted or substituted with 1 or 2 independently selected $R_5$ groups; or
(b) -phenyl, or -(5- or 6-membered)heteroaryl, each of which is unsubstituted or substituted with 1 or 2 independently selected $R_6$ groups;

each $R_5$ is independently selected from —$(C_1-C_4)$alkyl, —$(C_2-C_6)$alkenyl, —$(C_2-C_6)$alkynyl, -(5- or 6-membered)heteroaryl, -phenyl, —$(C_1-C_6)$alkylCOOR$_7$, —$OR_7$, —$SR_7$, —$C(halo)_3$, —$CH(halo)_2$, —$CH_2(halo)$, —CN, =O, =S, -halo, —$N_3$, —$NO_2$, —CH=N($R_7$), —$NR_7(C_1-C_6)$alkylCOOR$_7$, —$N(R_7)_2$, —$N(R_7)OH$, —$N(R_7)S(=O)R_8$, —$N(R_7)S(=O)_2R_8$, —$N(R_7)C(=O)R_8$, —$N(R_7)C(=O)N(R_7)_2$, —$N(R_7)C(=O)OR_8$, —$C(=O)R_7$, —$C(=O)$—$C(=O)OR_7$, —$C(=O)N(R_7)_2$, —$C(=O)OR_7$, —$OC(=O)R_7$, —$OC(=O)N(R_7)_2$, —$OC(=O)OR_7$, —$S(=O)R_7$, or —$S(=O)_2R_7$;

each $R_6$ is independently selected from —$(C_1-C_4)$alkyl, —$(C_2-C_6)$alkenyl, —$(C_2-C_6)$alkynyl, —$OR_7$, —$SR_7$, —$C(halo)_3$, —$CH(halo)_2$, —$CH_2(halo)$, —CN, -halo, —$N_3$, —$NO_2$, —CH=N($R_7$), —$N(R_7)_2$, —$N(R_7)OH$, —$N(R_7)S(=O)R_8$, —$N(R_7)S(=O)_2R_3$, —$N(R_7)C(=O)R_8$, —$N(R_7)C(=O)N(R_7)_2$, —$N(R_7)C(=O)OR_8$, —$C(=O)R_7$, —$C(=O)N(R_7)_2$, —$C(=O)OR_7$, —$OC(=O)R_7$, —$OC(=O)N(R_7)_2$, —$OC(=O)OR_7$, —$S(=O)R_7$, or —$S(=O)_2R_7$;

each $R_7$ is independently selected from —H, —$(C_1-C_6)$alkyl, —$(C_2-C_6)$alkenyl, —$(C_2-C_6)$alkynyl, —$(C_1-C_6)$alkoxy, —$(C_3-C_8)$cycloalkyl, —$(C_5-C_8)$cycloalkenyl, -phenyl, -benzyl, -(3- to 6-membered)heterocycle, -(5- to 10-membered)heteroaryl, —$C(halo)_3$, —$CH(halo)_2$, or —$CH_2(halo)$;

each $R_8$ is independently selected from —H or —$(C_1-C_4)$alkyl;

the dashed line denotes the presence or absence of a bond, wherein $E_1$ is selected from $C(T_3)_2$, O, S or $NT_3$ if the bond is absent, and $E_1$ is selected from $CT_3$, or N if the bond is present;

$E_2$ is selected from $C(T_3)_2$, O, S or $NT_3$;

each $T_1$, $T_2$, and $T_3$ is independently is independently —H or —$(C_1-C_{10})$alkyl which is unsubstituted or substituted with 1, 2 or 3 independently selected $R_5$ groups; and each halo is independently selected from —F, —Cl, —Br, or —I.

In a further embodiment, the present invention relates to a compound having the following general formula (III.1):

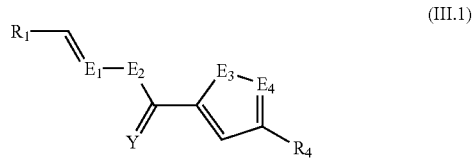

(III.1)

or a pharmaceutically acceptable derivative thereof wherein:
$R_1$ is selected from -phenyl, or -(5- or 6-membered)heteroaryl, each of which is unsubstituted or substituted with 1 or 2 independently selected $R_6$ groups;

Y is selected from O, S, or $NT_3$;

$R_4$ is selected from:
(a) —$(C_3-C_7)$cycloalkyl, —$(C_5-C_{10})$cycloalkenyl, or -(5- or 6-membered)heterocycle, each of which is unsubstituted or substituted with 1 or 2 independently selected $R_5$ groups; or
(b) -phenyl, or -(5- or 6-membered)heteroaryl, each of which is unsubstituted or substituted with 1 or 2 independently selected $R_6$ groups;

$E_1$ is selected from $CT_3$, or N;
$E_2$ is selected from $C(T_3)_2$, O, S or $NT_3$;
$E_3$ is selected from $C(T_3)_2$, O, S or $NT_3$;
$E_4$ is selected from $CT_3$, or N;

each $R_5$ is independently selected from —$(C_1-C_3)$alkyl, —$(C_2-C_3)$alkenyl, —$(C_2-C_3)$alkynyl, —$(C_1-C_3)$alkylCOOR$_7$, —$OR_7$, —$SR_7$, —$C(halo)_3$, —$CH(halo)_2$, —$CH_2(halo)$, —CN, =O, =S, -halo, —$N_3$, —$NO_2$, —$N(R_7)_2$, —$N(R_7)OH$, —$C(=O)R_7$, —$C(=O)OR_7$, —$OC(=O)R_7$, —$S(=O)R_7$, or —$S(=O)_2R_7$;

each $R_6$ is independently selected from —$(C_1-C_3)$alkyl, —$(C_2-C_3)$alkenyl, —$(C_2-C_3)$alkynyl, —$OR_7$, —$SR_7$, —$C(halo)_3$, —$CH(halo)_2$, —$CH_2(halo)$, —CN, -halo, —$N_3$, —$NO_2$, —$N(R_7)_2$, —$N(R_7)OH$, —$C(=O)R_7$, —$C(=O)OR_7$, —$OC(=O)R_7$, —$S(=O)R_7$, or —$S(=O)_2R_7$;

each $R_7$ is independently selected from —H, —CH$_3$, or —CH$_2$CH$_3$;
each $T_3$ is independently —H or —(C$_1$-C$_5$)alkyl which is unsubstituted or substituted with 1 or 2 independently selected $R_5$ groups; and
each halo is independently selected from —F, —Cl, —Br, or —I.

In a further embodiment, the present invention relates to a compound having the following general formula (III.2):

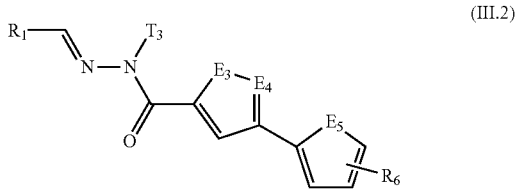
(III.2)

or a pharmaceutically acceptable derivative thereof wherein:
$R_1$ is selected from: -phenyl, or -heteroaryl selected from the group consisting of pyridine, pyrazine, pyridazine and pyrimidine, each of which is unsubstituted or substituted with 1 or 2 independently selected $R_6$ groups;
$E_3$ is selected from C(T$_3$)$_2$, O, S or NT$_3$;
$E_4$ is selected from CT$_3$, or N;
$E_5$ is selected from C(T$_3$)$_2$, O, or S;
$R_6$ is selected from —H, —(C$_1$-C$_2$)alkyl, —(C$_2$)alkenyl, —(C$_2$)alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)OR$_7$, —S(=O)R$_7$, or —S(=O)$_2$R$_7$;
each $R_7$ is independently selected from or —CH$_3$;
each $T_3$ is independently selected from —H or —CH$_3$; and
each halo is independently selected from —F, —Cl, —Br, or —I.

In an optional embodiment, the present invention relates to a compound having the general formula (III.2) or a pharmaceutically acceptable derivative thereof, wherein $R_1$ is:

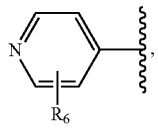

wherein $R_6$ is defined as above.

In an optional embodiment, the present invention relates to a compound having the general formula (III.2) or a pharmaceutically acceptable derivative thereof, wherein $R_1$ is:

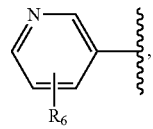

wherein $R_6$ is defined as above.

In an optional embodiment, the present invention relates to a compound having the general formula (III.2) or a pharmaceutically acceptable derivative thereof, wherein $R_1$ is:

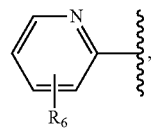

wherein $R_6$ is defined as above.

In an optional embodiment, the present invention relates to a compound having the general formula (III.2) or a pharmaceutically acceptable derivative thereof, wherein $R_1$ is:

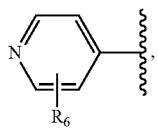

wherein $R_6$ is selected from —H, —CH$_3$, —OH, —SH, —OCH$_3$, or —Cl.

In an optional embodiment, the present invention relates to a compound having the general formula (III.2) or a pharmaceutically acceptable derivative thereof, wherein $R_1$ is:

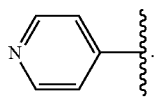

In an optional embodiment, the present invention relates to a compound having the general formula (III.2) or a pharmaceutically acceptable derivative thereof, wherein $E_3$ is NT$_3$ and $T_3$ is as defined above.

In an optional embodiment, the present invention relates to a compound having the general formula (III.2) or a pharmaceutically acceptable derivative thereof, wherein $E_4$ is N.

In an optional embodiment, the present invention relates to a compound having the general formula (III.2) or a pharmaceutically acceptable derivative thereof, wherein $E_5$ is S.

In an optional embodiment, the present invention relates to a compound having the general formula (III.2) or a pharmaceutically acceptable derivative thereof, wherein $E_3$ is NT$_3$, $E_4$ is N and $E_5$ is S, and $T_3$ is as defined above.

In an optional embodiment, the present invention relates to a compound having the general formula (III.2) or a pharmaceutically acceptable derivative thereof, wherein $R_6$ is selected from —H, —CH$_3$, —OH, —SH, —OCH$_3$, or —Cl.

In an optional embodiment, the present invention relates to a compound having the general formula (III.2) or a pharmaceutically acceptable derivative thereof, wherein $R_1$ is -phenyl, which is unsubstituted or substituted with 1 or 2 independently selected groups selected from —H, —CH$_3$, —OH, —SH, —OCH$_3$, —NH$_2$, —N(CH$_3$)$_2$ and —Cl.

In one embodiment, the present invention relates to a compound having the following general formula (IV):

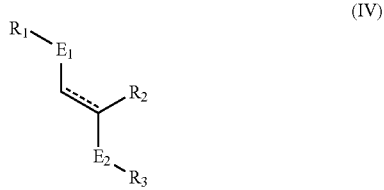

(IV)

or a pharmaceutically acceptable derivative thereof wherein:

$R_1$ is selected from:
(a) —$(C_3$-$C_7)$cycloalkyl, —$(C_6$-$C_{14})$bicycloalkyl, —$(C_8$-$C_{20})$tricycloalkyl, —$(C_5$-$C_{10})$cycloalkenyl, —$(C_7$-$C_{14})$bicycloalkenyl, —$(C_8$-$C_{20})$tricycloalkenyl, -(5- or 6-membered)heterocycle, or -(7- to 10-membered)bicycloheterocycle, each of which is unsubstituted or substituted with 1, 2 or 3 independently selected $R_4$ groups; or
(b) -phenyl, -naphthalenyl, —$(C_{14})$aryl, or -(5- or 6-membered)heteroaryl, each of which is unsubstituted or substituted with 1, 2 or 3 independently selected $R_4$ groups;

$R_2$ is selected from =O, =$NT_3$, =S, —$OT_3$, —OC(=O)$T_3$, —OC(=O)N($T_1$)($T_2$), —OC(=O)$OT_3$, —$ST_3$, —S(=O)$T_3$, —S(=O)$_2T_3$, —S(=O)$_2OT_3$, —S(=O)$_2$N($T_1$)($T_2$), —S(=O)$OT_3$, —S(=O)N($T_1$)($T_2$), —N($T_1$)($T_2$), —N($T_3$)N($T_1$)($T_2$), —N($T_3$)C(=O)$T_3$, —N($T_3$)C(=O)$OT_3$, —N($T_3$)C(=O)N($T_1$)($T_2$), —N($T_3$)S(=O)$_2T_3$, —N($T_3$)S(=O)$_2$N($T_1$)($T_2$), —N($T_3$)S(=O)$T_3$, or —N($T_3$)S(=O)N($T_1$)($T_2$);

$R_3$ is selected from:
(a) —$(C_3$-$C_7)$cycloalkyl, —$(C_6$-$C_{14})$bicycloalkyl, —$(C_8$-$C_{20})$tricycloalkyl, —$(C_5$-$C_{10})$cycloalkenyl, —$(C_7$-$C_{14})$bicycloalkenyl, —$(C_8$-$C_{20})$tricycloalkenyl, -(5- or 6-membered)heterocycle, or -(7- to 10-membered)bicycloheterocycle, each of which is unsubstituted or substituted with 1, 2 or 3 independently selected $R_5$ groups; or
(b) -phenyl, -naphthalenyl, —$(C_{14})$aryl, or -(5- or 6-membered)heteroaryl, each of which is unsubstituted or substituted with 1, 2 or 3 independently selected $R_6$ groups;

each $R_4$ is independently selected from:
(a) -halo, —CN, —$NO_2$; or
(b) —$OT_3$, —OC(=O)$T_3$, —OC(=O)N($T_1$)($T_2$), —OC(=O)$OT_3$; or
(c) —C(=O)$T_3$, —C(=O)$OT_3$, —C(=O)N($T_1$)($T_2$); or
(d) —$ST_3$, —S(=O)$T_3$, —S(=O)$_2T_3$, —S(=O)$_2OT_3$, —S(=O)$_2$N($T_1$)($T_2$), —S(=O)$OT_3$, —S(=O)N($T_1$)($T_2$); or
(e) —N($T_1$)($T_2$), —N($T_3$)N($T_1$)($T_2$), —N($T_3$)C(=O)$T_3$, —N($T_3$)C(=O)$OT_3$, —N($T_3$)C(=O)N($T_1$)($T_2$), —N($T_3$)S(=O)$_2T_3$, —N($T_3$)S(=O)$_2$N($T_1$)($T_2$), —N($T_3$)S(=O)$T_3$, —N($T_3$)S(=O)N($T_1$)($T_2$); or
(f) —$(C_1$-$C_6)$alkyl, —$(C_2$-$C_6)$alkenyl, —$(C_2$-$C_6)$alkynyl, —$(C_1$-$C_6)$alkoxy, —$(C_3$-$C_7)$cycloalkyl, —$(C_6$-$C_{14})$bicycloalkyl, each of which is unsubstituted or substituted with 1, 2 or 3 independently selected $R_5$ groups; or
(g) -phenyl or -(5- or 6-membered)heteroaryl, each of which is unsubstituted or substituted with 1, 2 or 3 independently selected $R_6$ groups;

$E_1$ and $E_2$ are each independently selected from C($T_3$)$_2$, O, S or $NT_3$;
the dashed line denotes the presence or absence of a bond;

each $R_5$ is independently selected from —$(C_1$-$C_4)$alkyl, —$(C_2$-$C_6)$alkenyl, —$(C_2$-$C_6)$alkynyl, -(5- or 6-membered)heteroaryl, -phenyl, —$(C_1$-$C_6)$alkylCOO$R_7$, —$OR_7$, —$SR_7$, —C(halo)$_3$, —CH(halo)$_2$, —$CH_2$(halo), —CN, =O, =S, -halo, —$N_3$, —$NO_2$, —CH=N($R_7$), —$NR_7(C_1$-$C_6)$alkyl-COO$R_7$, —N($R_7$)$_2$, —N($R_7$)OH, —N($R_7$)S(=O)$R_8$, —N($R_7$)S(=O)$_2R_8$, —N($R_7$)C(=O)$R_8$, —N($R_7$)C(=O)N($R_7$)$_2$, —N($R_7$)C(=O)$OR_8$, —C(=O)$R_7$, —C(=O)—C(=O)$OR_7$, —C(=O)N($R_7$)$_2$, —C(=O)$OR_7$, —OC(=O)$R_7$, —OC(=O)N($R_7$)$_2$, —OC(=O)$OR_7$, —S(=O)$R_7$, or —S(=O)$_2R_7$;

each $R_6$ is independently selected from —$(C_1$-$C_4)$alkyl, —$(C_2$-$C_6)$alkenyl, —$(C_2$-$C_6)$alkynyl, —$OR_7$, —$SR_7$, —C(halo)$_3$, —CH(halo)$_2$, —$CH_2$(halo), —CN, -halo, —$N_3$, —$NO_2$, —CH=N($R_7$), —N($R_7$)$_2$, —N($R_7$)OH, —N($R_7$)S(=O)$R_8$, —N($R_7$)S(=O)$_2R_8$, —N($R_7$)C(=O)$R_8$, —N($R_7$)C(=O)N($R_7$)$_2$, —N($R_7$)C(=O)$OR_8$, —C(=O)$R_7$, —C(=O)N($R_7$)$_2$, —C(=O)$OR_7$, —OC(=O)$R_7$, —OC(=O)N($R_7$)$_2$, —OC(=O)$OR_7$, —S(=O)$R_7$, or —S(=O)$_2R_7$;

each $R_7$ is independently selected from —H, —$(C_1$-$C_6)$alkyl, —$(C_2$-$C_6)$alkenyl, —$(C_2$-$C_6)$alkynyl, —$(C_1$-$C_6)$alkoxy, —$(C_3$-$C_8)$cycloalkyl, —$(C_5$-$C_8)$cycloalkenyl, -phenyl, -benzyl, -(3- to 6-membered)heterocycle, -(5- to 10-membered)heteroaryl, —C(halo)$_3$, —CH(halo)$_2$, or —$CH_2$(halo);

each $R_8$ is independently selected from —H or —$(C_1$-$C_4)$alkyl;

each $T_1$, $T_2$, and $T_3$ is independently —H or —$(C_1$-$C_{10})$alkyl which is unsubstituted or substituted with 1, 2 or 3 independently selected $R_5$ groups; and each halo is independently selected from —F, —Cl, —Br, or —I.

In one embodiment, the present invention relates to a compound having the following general formula (IV.1):

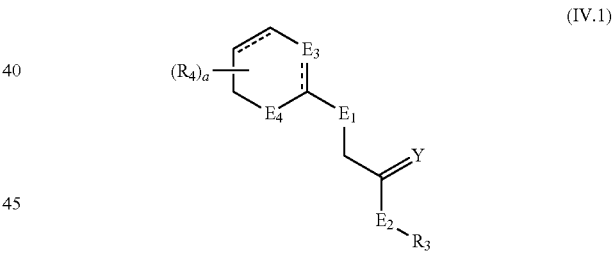

(IV.1)

or a pharmaceutically acceptable derivative thereof wherein:
$R_3$ is selected from -phenyl, or -(6-membered)heteroaryl, each of which is unsubstituted or substituted with 1 or 2 independently selected $R_6$ groups;

each $R_4$ is independently selected from:
(a) —$(C_1$-$C_4)$alkyl, —$(C_2$-$C_4)$alkenyl, —$(C_2$-$C_4)$alkynyl, —$(C_1$-$C_4)$alkoxy, each of which is unsubstituted or substituted with 1 or 2 independently selected $R_5$ groups; or
(b) —$OR_7$, —$SR_7$, —C(halo)$_3$, —CH(halo)$_2$, —$CH_2$(halo), —CN, =O, =S, -halo, —$N_3$, —$NO_2$, —N($R_7$)$_2$, —N($R_7$)OH, —C(=O)$R_7$, —C(=O)N($T_1$)($T_2$), —C(=O)$OR_7$, —OC(=O)$R_7$, —S(=O)$R_7$, or —S(=O)$_2R_7$;

Y is selected from O, S, or $NT_3$;
$E_1$ and $E_2$ are each independently selected from C($T_3$)$_2$, O, S or $NT_3$;
each dashed line in the 6-membered ring independently denotes the presence or absence of a bond, wherein $E_3$ is selected from C(T$_3$)$_2$, or NT$_3$ if the adjacent bond is absent, and E$_3$ is selected from CT$_3$, or N if the adjacent bond is present;
E$_4$ is selected from C(T$_3$)$_2$, or NT$_3$;
a is an integer selected from 1, 2 or 3;
each R$_5$ is independently selected from —(C$_1$-C$_3$)alkyl, —(C$_2$-C$_3$)alkenyl, —(C$_2$-C$_3$)alkynyl, —(C$_1$-C$_3$)alkyl-COOR$_7$, —OR$_7$, —SR$_7$, —C(halo)$_3$, —CH(halo)$_2$, —CH$_2$(halo), —CN, =O, =S, -halo, —N$_3$, —NO$_2$, —N(R$_7$)$_2$, —N(R$_7$)OH, —C(=O)R$_7$, —C(=O)OR$_7$, —OC(=O)R$_7$, —S(=O)R$_7$, or —S(=O)$_2$R$_7$;
each R$_6$ is independently selected from —(C$_1$-C$_3$)alkyl, —(C$_2$-C$_3$)alkenyl, —(C$_2$-C$_3$)alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)OR$_7$, —OC(=O)R$_7$, —S(=O)R$_7$, or —S(=O)$_2$R$_7$;
each R$_7$ is independently selected from —H, —CH$_3$, or —CH$_2$CH$_3$;
each T$_1$, T$_2$, and T$_3$ is independently —H or —(C$_1$-C$_5$)alkyl which is unsubstituted or substituted with 1 or 2 independently selected R$_5$ groups; and
each halo is independently selected from —F, —Cl, —Br, or —I.

In one embodiment, the present invention relates to a compound having the following general formula (IV.2):

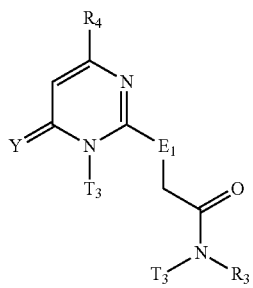

(IV.2)

or a pharmaceutically acceptable derivative thereof wherein:
R$_3$ is selected from: -phenyl, or -heteroaryl selected from the group consisting of pyridine, pyrazine, pyridazine and pyrimidine, each of which is unsubstituted or substituted with 1 or 2 independently selected R$_6$ groups;
R$_4$ is selected from: —(C$_1$-C$_4$)alkyl, —(C$_2$-C$_4$)alkenyl, —(C$_2$-C$_4$)alkynyl, —(C$_1$-C$_4$)alkoxy;
E$_1$ is selected from O or S;
Y is selected from O or S;
each R$_6$ is independently selected from —H, —(C$_1$-C$_2$)alkyl, —(C$_2$)alkenyl, —(C$_2$)alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —S(=O)R$_7$, or —S(=O)$_2$R$_7$;
each R$_7$ is independently selected from —H, or —CH$_3$;
each T$_3$ is independently selected from —H or —CH$_3$; and
each halo is independently selected from —F, —Br, or —I.

In an optional embodiment, the present invention relates to a compound having the general formula (IV.2) or a pharmaceutically acceptable derivative thereof, wherein R$_3$ is:

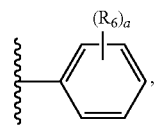

wherein R$_6$ is defined as above and a is an integer selected from 1 or 2.

In an optional embodiment, the present invention relates to a compound having the general formula (IV.2) or a pharmaceutically acceptable derivative thereof, wherein R$_3$ is:

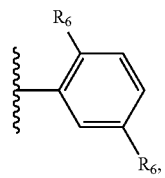

wherein R$_6$ is defined as above.

In an optional embodiment, the present invention relates to a compound having the general formula (IV.2) or a pharmaceutically acceptable derivative thereof, wherein R$_3$ is:

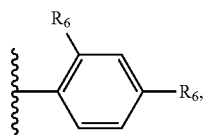

wherein R$_6$ is defined as above.

In an optional embodiment, the present invention relates to a compound having the general formula (IV.2) or a pharmaceutically acceptable derivative thereof, wherein R$_3$ is:

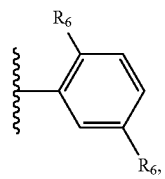

wherein R$_6$ is selected from —C(Cl)$_3$, —CH(Cl)$_2$, —CH$_2$(Cl), —Cl.

In an optional embodiment, the present invention relates to a compound having the general formula (IV.2) or a pharmaceutically acceptable derivative thereof, wherein R$_4$ is —(C$_1$-C$_4$)alkyl.

In an optional embodiment, the present invention relates to a compound having the general formula (IV.2) or a pharmaceutically acceptable derivative thereof, wherein E$_1$ is S.

In an optional embodiment, the present invention relates to a compound having the general formula (IV.2) or a pharmaceutically acceptable derivative thereof, wherein Y is O.

In an optional embodiment, the present invention relates to a compound having the general formula (IV.2) or a pharmaceutically acceptable derivative thereof, wherein R$_6$ is -halo.

In an optional embodiment, the present invention relates to a compound having the general formula (IV.2) or a pharmaceutically acceptable derivative thereof, wherein halo is Cl.

In one embodiment, the present invention relates to a compound having the following general formula (V):

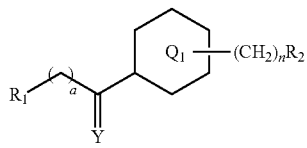

or a pharmaceutically acceptable derivative thereof wherein:
$R_1$ is selected from:
- (a) —$(C_3-C_7)$cycloalkyl, —$(C_6-C_{14})$bicycloalkyl, —$(C_8-C_{20})$tricycloalkyl, —$(C_5-C_{10})$cycloalkenyl, —$(C_7-C_{14})$bicycloalkenyl, —$(C_8-C_{20})$tricycloalkenyl, -(5- or 6-membered)heterocycle, or -(7- to 10-membered)bicycloheterocycle, each of which is unsubstituted or substituted with 1, 2 or 3 independently selected $R_3$ groups; or
- (b) -phenyl, -naphthalenyl, —$(C_{14})$aryl, -(5- or 6-membered)heteroaryl or -(7- or 10-membered)heteroaryl, each of which is unsubstituted or substituted with 1, 2 or 3 independently selected $R_3$ groups;

$R_2$ is selected from:
- (a) —$(C_3-C_7)$cycloalkyl, —$(C_6-C_{14})$bicycloalkyl, —$(C_8-C_{20})$tricycloalkyl, —$(C_5-C_{10})$cycloalkenyl, —$(C_7-C_{14})$bicycloalkenyl, —$(C_8-C_{20})$tricycloalkenyl, -(5- or 6-membered)heterocycle, or -(7- to 10-membered)bicycloheterocycle, each of which is unsubstituted or substituted with 1, 2 or 3 independently selected $R_5$ groups; or
- (b) -phenyl, -naphthalenyl, —$(C_{14})$aryl, -(5- or 6-membered)heteroaryl or -(7- or 10-membered)heteroaryl, each of which is unsubstituted or substituted with 1, 2 or 3 independently selected $R_6$ groups;

each $R_3$ is independently selected from:
- (a) -halo, —CN, —$NO_2$; or
- (b) —$OT_3$, —OC(=O)$T_3$, —OC(=O)N($T_1$)($T_2$), —OC(=O)$OT_3$; or
- (c) —C(=O)$T_3$, —C(=O)$OT_3$, —C(=O)N($T_1$)($T_2$); or
- (d) —$ST_3$, —S(=O)$T_3$, —S(=O)$_2T_3$, —S(=O)$_2OT_3$, —S(=O)$_2$N($T_1$)($T_2$), —S(=O)$OT_3$, —S(=O)N($T_1$)($T_2$); or
- (e) —N($T_1$)($T_2$), —N($T_3$)N($T_1$)($T_2$), —N($T_3$)C(=O)$T_3$, —N($T_3$)C(=O)$OT_3$, —N($T_3$)C(=O)N($T_1$)($T_2$), —N($T_3$)S(=O)$_2T_3$, —N($T_3$)S(=O)$_2$N($T_1$)($T_2$), —N($T_3$)S(=O)$T_3$, —N($T_3$)S(=O)N($T_1$)($T_2$); or
- (f) —$(C_1-C_6)$alkyl, —$(C_2-C_6)$alkenyl, —$(C_2-C_6)$alkynyl, —$(C_1-C_6)$alkoxy, —$(C_3-C_7)$cycloalkyl, —$(C_6-C_{14})$bicycloalkyl, each of which is unsubstituted or substituted with 1, 2 or 3 independently selected $R_5$ groups; or
- (g) -phenyl or -(5- or 6-membered)heteroaryl, each of which is unsubstituted or substituted with 1, 2 or 3 independently selected $R_6$ groups;

a is an integer selected from 1, 2 or 3;
Y is selected from O, S, or $NT_3$;
the 6-membered ring denoted as $Q_1$ is selected from —$(C_6)$cycloalkyl, —$(C_6)$cycloalkenyl, -(6-membered)heterocycle, -phenyl, or -(6-membered)heteroaryl;
n is an integer selected from 0, 1, 2 or 3;
each $R_5$ is independently selected from —$(C_1-C_4)$alkyl, —$(C_2-C_6)$alkenyl, —$(C_2-C_6)$alkynyl, -(5- or 6-membered)heteroaryl, -phenyl, —$(C_1-C_6)$alkylCOO$R_7$, —$OR_7$, —$SR_7$, —C(halo)$_3$, —CH(halo)$_2$, —$CH_2$(halo), —CN, =O, =S, -halo, —$N_3$, —$NO_2$, —CH=N($R_7$), —$NR_7(C_1-C_6)$alkylCOO$R_7$, —N($R_7$)$_2$, —N($R_7$)OH, —N($R_7$)S(=O)$R_8$, —N($R_7$)S(=O)$_2R_8$, —N($R_7$)C(=O)$R_8$, —N($R_7$)C(=O)N($R_7$)$_2$, —N($R_7$)C(=O)$OR_8$, —C(=O)$R_7$, —C(=O)—C(=O)$OR_7$, —C(=O)N($R_7$)$_2$, —C(=O)$OR_7$, —OC(=O)$R_7$, —OC(=O)N($R_7$)$_2$, —OC(=O)$OR_7$, —S(=O)$R_7$, or —S(=O)$_2R_7$;

each $R_6$ is independently selected from —$(C_1-C_4)$alkyl, —$(C_2-C_6)$alkenyl, —$(C_2-C_6)$alkynyl, —$OR_7$, —$SR_7$, —C(halo)$_3$, —CH(halo)$_2$, —$CH_2$(halo), —CN, -halo, —$N_3$, —$NO_2$, —CH=N($R_7$), —N($R_7$)$_2$, —N($R_7$)OH, —N($R_7$)S(=O)$R_8$, —N($R_7$)S(=O)$_2R_8$, —N($R_7$)C(=O)$R_8$, —N($R_7$)C(=O)N($R_7$)$_2$, —N($R_7$)C(=O)$OR_8$, —C(=O)$R_7$, —C(=O)N($R_7$)$_2$, —C(=O)$OR_7$, —OC(=O)$R_7$, —OC(=O)N($R_7$)$_2$, —OC(=O)$OR_7$, —S(=O)$R_7$, or —S(=O)$_2R_7$;

each $R_7$ is independently selected from —H, —$(C_1-C_6)$alkyl, —$(C_2-C_6)$alkenyl, —$(C_2-C_6)$alkynyl, —$(C_1-C_6)$alkoxy, —$(C_3-C_8)$cycloalkyl, —$(C_5-C_8)$cycloalkenyl, -phenyl, -benzyl, -(3- to 6-membered)heterocycle, -(5- to 10-membered)heteroaryl, —C(halo)$_3$, —CH(halo)$_2$, or —$CH_2$(halo);

each $R_8$ is independently selected from —H or —$(C_1-C_4)$alkyl;

each $T_1$, $T_2$, and $T_3$ is independently —H or —$(C_1-C_{10})$alkyl which is unsubstituted or substituted with 1, 2 or 3 independently selected $R_5$ groups; and each halo is independently selected from —F, —Cl, —Br, or —I.

In one embodiment, the present invention relates to a compound having the following general formula (V.1):

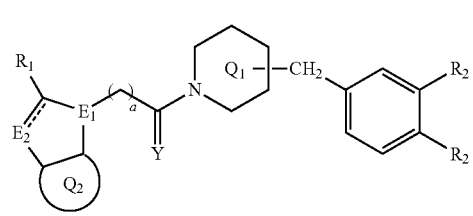

or a pharmaceutically acceptable derivative thereof wherein:
$R_1$ is selected from:
- (a) —H; or
- (b) -halo, —CN, —$NO_2$; or
- (c) —$OT_3$, —OC(=O)$T_3$; or
- (d) —C(=O)$T_3$; or
- (e) —N($T_1$)($T_2$), —N($T_3$)N($T_1$)($T_2$), —N($T_3$)C(=O)$T_3$, —N($T_3$)C(=O)$OT_3$; or
- (f) —$ST_3$, —S(=O)$T_3$, —S(=O)$_2T_3$, —S(=O)$_2OT_3$; or
- (g) —$(C_1-C_4)$alkyl, —$(C_2-C_4)$alkenyl, —$(C_2-C_4)$alkynyl, —$(C_1-C_4)$alkoxy, each of which is unsubstituted or substituted with 1 or 2 independently selected $R_5$ groups;

each $R_2$ is independently selected from:
- (a) —H; or
- (b) -halo, —CN, —$NO_2$; or
- (c) —$OT_3$, —OC(=O)$T_3$; or
- (d) —C(=O)$T_3$; or
- (e) —N($T_1$)($T_2$), —N($T_3$)N($T_1$)($T_2$), —N($T_3$)C(=O)$T_3$, —N($T_3$)C(=O)$OT_3$; or
- (f) —$ST_3$, —S(=O)$T_3$, —S(=O)$_2T_3$, —S(=O)$_2OT_3$; or
- (g) —$(C_1-C_5)$alkyl, —$(C_2-C_5)$alkenyl, —$(C_2-C_5)$alkynyl, —$(C_1-C_5)$alkoxy, —$(C_3-C_7)$cycloalkyl, —$(C_5-C_{10})$cycloalkenyl, or -(5- or 6-membered)heterocycle, each of which is unsubstituted or substituted with 1 or 2 independently selected $R_5$ groups;

wherein both $R_2$ can together form a (2- to 6-membered) bridge, which is unsubstituted or substituted with 1 or 2 independently selected $R_5$ groups;

the 6-membered ring denoted as $Q_1$ is selected from -(6-membered)heterocycle, or -(6-membered)heteroaryl, each of each at least containing one nitrogen atom at the position as depicted in formula (V.1);

$Q_2$ is selected from fused benzo or 6-membered heteroaryl, each of which is unsubstituted or substituted with 1 or 2 independently selected $R_6$ groups;

$E_1$ is selected from $C(T_3)_2$, or $NT_3$;

the dashed line in the 5-membered ring denotes the presence or absence of a bond, wherein $E_2$ is selected from $C(T_3)_2$, $NT_3$ if the bond is absent, and $E_2$ is selected from $CT_3$, or N if the bond is present;

Y is selected from O, S, or $NT_3$;

a is an integer selected from 1, 2 or 3;

each $R_5$ is independently selected from —$(C_1$-$C_3)$alkyl, —$(C_2$-$C_3)$alkenyl, —$(C_2$-$C_3)$alkynyl, —$(C_1$-$C_3)$alkyl-$COOR_7$, —$OR_7$, —$SR_7$, —$C(halo)_3$, —$CH(halo)_2$, —$CH_2(halo)$, —CN, =O, =S, -halo, —$N_3$, —$NO_2$, —$N(R_7)_2$, —$N(R_7)OH$, —$C(=O)R_7$, —$C(=O)OR_7$, —$OC(=O)R_7$, —$S(=O)R_7$, or —$S(=O)_2R_7$;

each $R_6$ is independently selected from —$(C_1$-$C_3)$alkyl, —$(C_2$-$C_3)$alkenyl, —$(C_2$-$C_3)$alkynyl, —$OR_7$, —$SR_7$, —$C(halo)_3$, —$CH(halo)_2$, —$CH_2(halo)$, —CN, -halo, —$N_3$, —$NO_2$, —$N(R_7)_2$, —$N(R_7)OH$, —$C(=O)R_7$, —$C(=O)OR_7$, —$OC(=O)R_7$, —$S(=O)R_7$, or —$S(=O)_2R_7$;

each $R_7$ is independently selected from —H, —$CH_3$, or —$CH_2CH_3$;

each $T_1$, $T_2$, and $T_3$ is independently is independently —H or —$(C_1$-$C_5)$alkyl which is unsubstituted or substituted with 1 or 2 independently selected $R_5$ groups; and each halo is independently selected from —F, —Cl, —Br, or —I.

In one embodiment, the present invention relates to a compound having the following general formula (V.2):

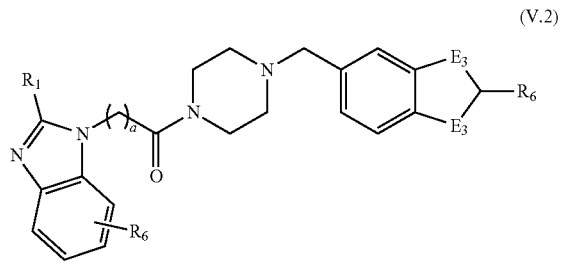

or a pharmaceutically acceptable derivative thereof wherein:
$R_1$ is selected from —H; —$OT_3$, —$N(T_3)_2$, —$ST_3$, —$(C_1$-$C_3)$alkoxy or —$(C_1$-$C_3)$alkyl, wherein $T_3$ is selected from —H or —$(C_1$-$C_2)$alkyl;

a is an integer selected from 1, 2 or 3;

each $E_3$ is independently selected from O or S;

each $R_6$ is independently selected from —H, —$(C_1$-$C_2)$alkyl, —$(C_2)$alkenyl, —$(C_2)$alkynyl, —$OR_7$, —$SR_7$, —$C(halo)_3$, —$CH(halo)_2$, —$CH_2(halo)$, —CN, -halo, —$N_3$, —$NO_2$, —$N(R_7)_2$, —$N(R_7)OH$, —$C(=O)R_7$, —$C(=O)OR_7$, —$S(=O)R_7$, or —$S(=O)_2R_7$;

each $R_7$ is independently selected from —H, or —$CH_3$; and each halo is independently selected from —F, —Cl, —Br, or —I.

In an optional embodiment, the present invention relates to a compound having the general formula (V.2) or a pharmaceutically acceptable derivative thereof, wherein $R_1$ is —$(C_1$-$C_3)$alkyl.

In an optional embodiment, the present invention relates to a compound having the general formula (V.2) or a pharmaceutically acceptable derivative thereof, wherein a=2.

In an optional embodiment, the present invention relates to a compound having the general formula (V.2) or a pharmaceutically acceptable derivative thereof, wherein $E_3$ is O.

In an optional embodiment, the present invention relates to a compound having the general formula (V.2) or a pharmaceutically acceptable derivative thereof, wherein $R_6$ is —H; —OH, —Cl, —$OCH_3$, —SH, —$SCH_3$ or —$CH_3$.

In one embodiment, the present invention relates to a compound having the following general formula (VI):

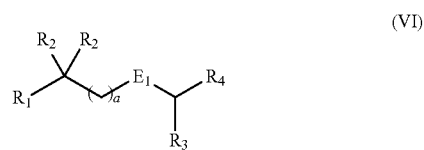

or a pharmaceutically acceptable derivative thereof wherein:
$R_1$ is selected from:
(a) —$(C_3$-$C_7)$cycloalkyl, —$(C_6$-$C_{14})$bicycloalkyl, —$(C_8$-$C_{20})$tricycloalkyl, —$(C_5$-$C_{10})$cycloalkenyl, —$(C_7$-$C_{14})$bicycloalkenyl, —$(C_8$-$C_{20})$tricycloalkenyl, -(5- or 6-membered)heterocycle, or -(7- to 10-membered)bicycloheterocycle, each of which is unsubstituted or substituted with 1, 2 or 3 independently selected $R_5$ groups; or
(b) -phenyl, -naphthalenyl, —$(C_{14})$aryl, -(5- or 6-membered)heteroaryl or -(7- or 10-membered)heteroaryl, each of which is unsubstituted or substituted with 1, 2 or 3 independently selected $R_6$ groups;

each $R_2$ is independently selected from:
(a) —H; or
(b) -halo, —CN, —$NO_2$; or
(c) —$OT_3$, —$OC(=O)T_3$, —$OC(=O)N(T_1)(T_2)$, —$OC(=O)OT_3$; or
(d) —$C(=O)T_3$, —$C(=O)OT_3$, —$C(=O)N(T_1)(T_2)$; or
(e) —$ST_3$, —$S(=O)T_3$, —$S(=O)_2T_3$, —$S(=O)_2OT_3$, —$S(=O)_2N(T_1)(T_2)$, —$S(=O)OT_3$, —$S(=O)N(T_1)(T_2)$; or
(f) —$N(T_1)(T_2)$, —$N(T_3)N(T_1)(T_2)$, —$N(T_3)C(=O)T_3$, —$N(T_3)C(=O)OT_3$, —$N(T_3)C(=O)N(T_1)(T_2)$, —$N(T_3)S(=O)_2T_3$, —$N(T_3)S(=O)_2N(T_1)(T_2)$, —$N(T_3)S(=O)T_3$, —$N(T_3)S(=O)N(T_1)(T_2)$; or
(g) —$(C_1$-$C_6)$alkyl, —$(C_2$-$C_6)$alkenyl, —$(C_2$-$C_6)$alkynyl, —$(C_1$-$C_6)$alkoxy, —$(C_3$-$C_7)$cycloalkyl, —$(C_6$-$C_{14})$bicycloalkyl, —$(C_8$-$C_{20})$tricycloalkyl, —$(C_5$-$C_{10})$cycloalkenyl, —$(C_7$-$C_{14})$bicycloalkenyl, —$(C_8$-$C_{20})$tricycloalkenyl, -(5- or 6-membered)heterocycle, or -(7- to 10-membered)bicycloheterocycle, each of which is unsubstituted or substituted with 1, 2 or 3 independently selected $R_5$ groups; or
(h) -phenyl or -(5- or 6-membered)heteroaryl, each of which is unsubstituted or substituted with 1, 2 or 3 independently selected $R_6$ groups;

wherein both $R_2$ can together form a (2- to 6-membered) bridge, which is unsubstituted or substituted with 1 or 2 independently selected $R_5$ groups;

$R_3$ is selected from =O, =NT$_3$, =S, —OT$_3$, —OC(=O)T$_3$, —OC(=O)N(T$_1$)(T$_2$), —OC(=O)OT$_3$, —ST$_3$, —S(=O)T$_3$, —S(=O)$_2$T$_3$, —S(=O)$_2$OT$_3$, —S(=O)$_2$N(T$_1$)(T$_2$), —S(=O)OT$_3$, —S(=O)N(T$_1$)(T$_2$), —N(T$_1$)(T$_2$), —N(T$_3$)N(T$_1$)(T$_2$), —N(T$_3$)C(=O)T$_3$, —N(T$_3$)C(=O)OT$_3$, —N(T$_3$)C(=O)N(T$_1$)(T$_2$), —N(T$_3$)S(=O)$_2$T$_3$, —N(T$_3$)S(=O)$_2$N(T$_1$)(T$_2$), —N(T$_3$)S(=O)T$_3$, or —N(T$_3$)S(=O)N(T$_1$)(T$_2$);

$R_4$ is selected from:
(a) —(C$_3$-C$_7$)cycloalkyl, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(5- or 6-membered)heterocycle, or -(7- to 10-membered)bicycloheterocycle, each of which is unsubstituted or substituted with 1, 2 or 3 independently selected R$_5$ groups; or
(b) -phenyl, -naphthalenyl, —(C$_{14}$)aryl, -(5- or 6-membered)heteroaryl or -(7- or 10-membered)heteroaryl, each of which is unsubstituted or substituted with 1, 2 or 3 independently selected R$_6$ groups;

$E_1$ is selected from C(T$_3$)$_2$, O, S or NT$_3$;
a is an integer selected from 0, 1, 2, or 3;
each $R_5$ is independently selected from —(C$_1$-C$_4$)alkyl, —(C$_2$-C$_6$)alkenyl, —(C$_2$-C$_6$)alkynyl, -(5- or 6-membered)heteroaryl, -phenyl, —(C$_1$-C$_6$)alkylCOOR$_7$, —OR$_7$, —SR$_7$, —C(halo)$_3$, —CH(halo)$_2$, —CH$_2$(halo), —CN, =O, =S, -halo, —N$_3$, —NO$_2$, —CH=N(R$_7$), —NR$_7$(C$_1$-C$_6$)alkylCOOR$_7$, —N(R$_7$)$_2$, —N(R$_7$)OH, —N(R$_7$)S(=O)R$_8$, —N(R$_7$)S(=O)$_2$R$_8$, —N(R$_7$)C(=O)R$_8$, —N(R$_7$)C(=O)N(R$_7$)$_2$, —N(R$_7$)C(=O)OR$_8$, —C(=O)R$_7$, —C(=O)—C(=O)OR$_7$, —C(=O)N(R$_7$)$_2$, —C(=O)OR$_7$, —OC(=O)R$_7$, —OC(=O)N(R$_7$)$_2$, —OC(=O)OR$_7$, —S(=O)R$_7$, or —S(=O)$_2$R$_7$;

each $R_6$ is independently selected from —(C$_1$-C$_4$)alkyl, —(C$_2$-C$_6$)alkenyl, —(C$_2$-C$_6$)alkynyl, —OR$_7$, —SR$_7$, —C(halo)$_3$, —CH(halo)$_2$, —CH$_2$(halo), —CN, -halo, —N$_3$, —NO$_2$, —CH=N(R$_7$), —N(R$_7$)$_2$, —N(R$_7$)OH, —N(R$_7$)S(=O)R$_8$, —N(R$_7$)S(=O)$_2$R$_8$, —N(R$_7$)C(=O)R$_8$, —N(R$_7$)C(=O)N(R$_7$)$_2$, —N(R$_7$)C(=O)OR$_8$, —C(=O)R$_7$, —C(=O)N(R$_7$)$_2$, —C(=O)OR$_7$, —OC(=O)R$_7$, —OC(=O)N(R$_7$)$_2$, —OC(=O)OR$_7$, —S(=O)R$_7$, or —S(=O)$_2$R$_7$;

each $R_7$ is independently selected from —H, —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_8$)cycloalkyl, —(C$_5$-C$_8$)cycloalkenyl, -phenyl, -benzyl, -(3- to 6-membered)heterocycle, -(5- to 10-membered)heteroaryl, —C(halo)$_3$, —CH(halo)$_2$, or —CH$_2$(halo);

each $R_8$ is independently selected from —H or —(C$_1$-C$_4$)alkyl;

each $T_1$, $T_2$, and $T_3$ is independently —H or —(C$_1$-C$_{10}$)alkyl which is unsubstituted or substituted with 1, 2 or 3 independently selected R$_5$ groups; and each halo is independently selected from —F, —Cl, —Br, or —I.

In a further embodiment, the present invention relates to a compound having the following general formula (VI.1):

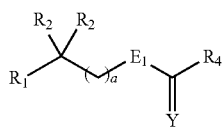

(VI.1)

or a pharmaceutically acceptable derivative thereof wherein:
$R_1$ is selected from -phenyl, or -(6-membered)heteroaryl, each of which is unsubstituted or substituted with 1 or 2 independently selected R$_6$ groups;

Y is selected from O or S;

each $R_2$ is independently selected from:
(a) —H; or
(b) -halo, —CN, —NO$_2$; or
(c) —OT$_3$, —OC(=O)T$_3$; or
(d) —C(=O)T$_3$; or
(e) —ST$_3$, —S(=O)T$_3$, —S(=O)$_2$T$_3$, —S(=O)$_2$OT$_3$; or
(f) —(C$_1$-C$_5$)alkyl, —(C$_2$-C$_5$)alkenyl, —(C$_2$-C$_5$)alkynyl, —(C$_1$-C$_5$)alkoxy, —(C$_3$-C$_7$)cycloalkyl, —(C$_5$-C$_{10}$)cycloalkenyl, or -(5- or 6-membered)heterocycle, each of which is unsubstituted or substituted with 1 or 2 independently selected R$_5$ groups;

wherein both R$_2$ can together form a (2- to 6-membered) bridge, which is unsubstituted or substituted with 1 or 2 independently selected R$_5$ groups;

$R_4$ is selected from -phenyl, or -(6-membered)heteroaryl, each of which is unsubstituted or substituted with 1 or 2 independently selected R$_6$ groups;

$E_1$ is selected from CT$_3$, or N;

each $R_5$ is independently selected from —(C$_1$-C$_3$)alkyl, —(C$_2$-C$_3$)alkenyl, —(C$_2$-C$_3$)alkynyl, —(C$_1$-C$_3$)alkyl-COOR$_7$, —OR$_7$, —SR$_7$, —C(halo)$_3$, —CH(halo)$_2$, —CH$_2$(halo), —CN, =O, =S, -halo, —N$_3$, —NO$_2$, —N(R$_7$)$_2$, —N(R$_7$)OH, —C(=O)R$_7$, —C(=O)OR$_7$, —OC(=O)R$_7$, —S(=O)R$_7$, or —S(=O)$_2$R$_7$;

each $R_6$ is independently selected from —(C$_1$-C$_3$)alkyl, —(C$_2$-C$_3$)alkenyl, —(C$_2$-C$_3$)alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)OR$_7$, —OC(=O)R$_7$, —S(=O)R$_7$, or —S(=O)$_2$R$_7$;

each $R_7$ is independently selected from —H, —CH$_3$, or —CH$_2$CH$_3$;

each $T_3$ is independently —H or —(C$_1$-C$_5$)alkyl which is unsubstituted or substituted with 1 or 2 independently selected R$_5$ groups; and each halo is independently selected from —F, —Cl, —Br, or —I.

In a further embodiment, the present invention relates to a compound having the following general formula (VI.2):

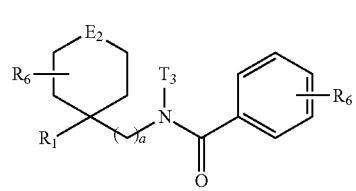

(VI.2)

or a pharmaceutically acceptable derivative thereof wherein:
$R_1$ is selected from -phenyl or -heteroaryl selected from the group consisting of pyridine, pyrazine, pyridazine and pyrimidine, each of which is unsubstituted or substituted with 1 or 2 independently selected R$_6$ groups;

a is an integer selected from 0, 1 or 2;

$E_2$ is O or S;

$T_3$ is selected from —H or —CH$_3$;

each $R_6$ is independently selected from —H, —(C$_1$-C$_2$)alkyl, —(C$_2$)alkenyl, —(C$_2$)alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)OR$_7$, —S(=O)R$_7$, or —S(=O)$_2$R$_7$;

each $R_7$ is independently selected from —H, or —$CH_3$; and each halo is independently selected from —F, —Cl, —Br, or —I.

In an optional embodiment, the present invention relates to a compound having the general formula (VI.2) or a pharmaceutically acceptable derivative thereof, wherein $R_1$ is:

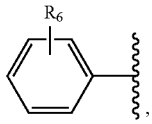

wherein $R_6$ is selected from —H; —OH, —$OCH_3$, —SH, —$SCH_3$, —Cl or —$CH_3$.

In an optional embodiment, the present invention relates to a compound having the general formula (VI.2) or a pharmaceutically acceptable derivative thereof, wherein $R_1$ is:

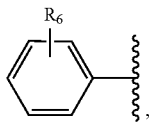

wherein $R_6$ is defined as above.

In an optional embodiment, the present invention relates to a compound having the general formula (VI.2) or a pharmaceutically acceptable derivative thereof, wherein a=1.

In an optional embodiment, the present invention relates to a compound having the general formula (VI.2) or a pharmaceutically acceptable derivative thereof, wherein $E_2$ is O.

In an optional embodiment, the present invention relates to a compound having the general formula (VI.2) or a pharmaceutically acceptable derivative thereof, wherein $R_6$ is selected from —H; —OH, —$OCH_3$, —SH, —$SCH_3$, —Cl or —$CH_3$.

In one embodiment, the present invention relates to a compound having the following general formula (VII):

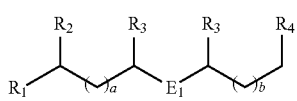

(VII)

or a pharmaceutically acceptable derivative thereof wherein:
$R_1$ is selected from:
 (a) —($C_3$-$C_7$)cycloalkyl, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(5- or 6-membered)heterocycle, or -(7- to 10-membered)bicycloheterocycle, each of which is unsubstituted or substituted with 1, 2 or 3 independently selected $R_5$ groups; or
 (b) -phenyl, -naphthalenyl, —($C_{14}$)aryl, -(5- or 6-membered)heteroaryl or -(7- or 10-membered)heteroaryl, each of which is unsubstituted or substituted with 1, 2 or 3 independently selected $R_6$ groups;

$R_2$ is selected from:
 (a) —H; or
 (b) -halo, —CN, —$NO_2$; or
 (c) —$OT_3$, —OC(=O)$T_3$, —OC(=O)N($T_1$)($T_2$), —OC(=O)$OT_3$; or
 (d) —C(=O)$OT_3$, —C(=O)N($T_1$)($T_2$); or
 (e) —$ST_3$, —S(=O)$T_3$, —S(=O)$_2T_3$, —S(=O)$_2OT_3$, —S(=O)$_2$N($T_1$)($T_2$), —S(=O)$OT_3$, —S(=O)N($T_1$)($T_2$); or
 (f) —N($T_1$)($T_2$), —N($T_3$)N($T_1$)($T_2$), —N($T_3$)C(=O)$T_3$, —N($T_3$)C(=O)$OT_3$, —N($T_3$)C(=O)N($T_1$)($T_2$), —N($T_3$)S(=O)$_2T_3$, —N($T_3$)S(=O)$_2$N($T_1$)($T_2$), —N($T_3$)S(=O)$T_3$, —N($T_3$)S(=O)N($T_1$)($T_2$); or
 (g) —($C_1$-$C_6$)alkyl, —($C_2$-$C_6$)alkenyl, —($C_2$-$C_6$)alkynyl, —($C_1$-$C_6$)alkoxy, —($C_3$-$C_7$)cycloalkyl, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(5- or 6-membered)heterocycle, or -(7- to 10-membered)bicycloheterocycle, each of which is unsubstituted or substituted with 1, 2 or 3 independently selected $R_5$ groups; or
 (h) -phenyl or -(5- or 6-membered)heteroaryl, each of which is unsubstituted or substituted with 1, 2 or 3 independently selected $R_6$ groups;

each $R_3$ is independently selected from —H, =O, =$NT_3$, =S, —$OT_3$, —OC(=O)$T_3$, —OC(=O)N($T_1$)($T_2$), —OC(=O)$OT_3$, —$ST_3$, —S(=O)$T_3$, —S(=O)$_2T_3$, —S(=O)$_2OT_3$, —S(=O)$_2$N($T_1$)($T_2$), —S(=O)$OT_3$, —S(=O)N($T_1$)($T_2$), —N($T_1$)($T_2$), —N($T_3$)N($T_1$)($T_2$), —N($T_3$)C(=O)$T_3$, —N($T_3$)C(=O)$OT_3$, —N($T_3$)C(=O)N($T_1$)($T_2$), —N($T_3$)S(=O)$_2T_3$, —N($T_3$)S(=O)$_2$N($T_1$)($T_2$), —N($T_3$)S(=O)$T_3$, or —N($T_3$)S(=O)N($T_1$)($T_2$);

$R_4$ is selected from:
 (a) —H; or
 (b) -halo, —CN, —$NO_2$; or
 (c) —$OT_3$, —OC(=O)$T_3$, —OC(=O)N($T_1$)($T_2$), —OC(=O)$OT_3$; or
 (d) —C(=O)$T_3$, —C(=O)$OT_3$, —C(=O)N($T_1$)($T_2$); or
 (e) —$ST_3$, —S(=O)$T_3$, —S(=O)$_2T_3$, —S(=O)$_2OT_3$, —S(=O)$_2$N($T_1$)($T_2$), —S(=O)$OT_3$, —S(=O)N($T_1$)($T_2$); or
 (f) —N($T_1$)($T_2$), —N($T_3$)N($T_1$)($T_2$), —N($T_3$)C(=O)$T_3$, —N($T_3$)C(=O)$OT_3$, —N($T_3$)C(=O)N($T_1$)($T_2$), —N($T_3$)S(=O)$_2T_3$, —N($T_3$)S(=O)$_2$N($T_1$)($T_2$), —N($T_3$)S(=O)$T_3$, —N($T_3$)S(=O)N($T_1$)($T_2$); or
 (g) —($C_1$-$C_6$)alkyl, —($C_2$-$C_6$)alkenyl, —($C_2$-$C_6$)alkynyl, —($C_1$-$C_6$)alkoxy, —($C_3$-$C_7$)cycloalkyl, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(5- or 6-membered)heterocycle, or -(7- to 10-membered)bicycloheterocycle, each of which is unsubstituted or substituted with 1, 2 or 3 independently selected $R_5$ groups; or
 (h) -phenyl or -(5- or 6-membered)heteroaryl, each of which is unsubstituted or substituted with 1, 2 or 3 independently selected $R_6$ groups;

$E_1$ is selected from C($T_3$)$_2$, O, S or $NT_3$;
a is an integer selected from 0, 1, 2, or 3;
b is an integer selected from 0, 1, 2, or 3;
each $R_5$ is independently selected from —($C_1$-$C_4$)alkyl, —($C_2$-$C_6$)alkenyl, —($C_2$-$C_6$)alkynyl, -(5- or 6-membered)heteroaryl, -phenyl, —($C_1$-$C_6$)alkylCOO$R_7$, —$OR_7$, —$SR_7$, —C(halo)$_3$, —CH(halo)$_2$, —$CH_2$(halo), —CN, =O, =S, -halo, —$N_3$, —$NO_2$, —CH=N($R_7$), —N$R_7$($C_1$-$C_6$)alkylCOO$R_7$, —N($R_7$)$_2$, —N($R_7$)OH, —N($R_7$)S(=O)$R_8$, —N($R_7$)S(=O)$_2R_8$, —N($R_7$)C(=O)$R_8$, —N($R_7$)C(=O)N($R_7$)$_2$, —N($R_7$)C(=O)O$R_8$, —C(=O)$R_7$, —C(=O)—C —C(=O)OR₇, —C(=O)N(R₇)₂, —C(=O)OR₇, —OC(=O)R₇, —OC(=O)N(R₇)₂, —OC(=O)OR₇, —S(=O)R₇, or —S(=O)₂R₇;

each R₆ is independently selected from —(C₁-C₄)alkyl, —(C₂-C₆)alkenyl, —(C₂-C₆)alkynyl, —OR₇, —SR₇, —C(halo)₃, —CH(halo)₂, —CH₂(halo), —CN, -halo, —N₃, —NO₂, —CH=N(R₇), —N(R₇)₂, —N(R₇)OH, —N(R₇)S(=O)R₈, —N(R₇)S(=O)₂R₈, —N(R₇)C(=O)R₈, —N(R₇)C(=O)N(R₇)₂, —N(R₇)C(=O)OR₈, —C(=O)R₇, —C(=O)N(R₇)₂, —C(=O)OR₇, —OC(=O)R₇, —OC(=O)N(R₇)₂, —OC(=O)OR₇, —S(=O)R₇, or —S(=O)₂R₇;

each R₇ is independently selected from —H, —(C₁-C₆)alkyl, —(C₂-C₆)alkenyl, —(C₂-C₆)alkynyl, —(C₁-C₆)alkoxy, —(C₃-C₈)cycloalkyl, —(C₅-C₈)cycloalkenyl, -phenyl, -benzyl, -(3- to 6-membered)heterocycle, -(5- to 10-membered)heteroaryl, —C(halo)₃, —CH(halo)₂, or —CH₂(halo);

each R₈ is independently selected from —H or —(C₁-C₄) alkyl;

each T₁, T₂, and T₃ is independently —H or —(C₁-C₁₀)alkyl which is unsubstituted or substituted with 1, 2 or 3 independently selected R₅ groups; and each halo is independently selected from —F, —Cl, —Br, or —I.

In a further embodiment, the present invention relates to a compound having the following general formula (VII.1):

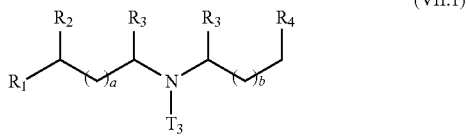

(VII.1)

or a pharmaceutically acceptable derivative thereof wherein:
R₁ is selected from -phenyl, or -(6-membered)heteroaryl, each of which is unsubstituted or substituted with 1 or 2 independently selected R₆ groups;

R₂ is selected from:
(a) —H; or
(b) —(C₁-C₅)alkyl, —(C₂-C₅)alkenyl, —(C₂-C₅)alkynyl, —(C₁-C₅)alkoxy, —(C₃-C₇)cycloalkyl, —(C₅-C₁₀)cycloalkenyl, or -(5- or 6-membered)heterocycle, each of which is unsubstituted or substituted with 1 or 2 independently selected R₅ groups;

each R₃ is independently selected from —H, =O, =NT₃, or =S;

R₄ is selected from:
(a) —H; or
(b) —N(T₁)(T₂), —N(T₃)N(T₁)(T₂), —N(T₃)C(=O)T₃, —N(T₃)C(=O)OT₃, —N(T₃)C(=O)N(T₁)(T₂); or
(c) —OT₃, —OC(=O)T₃; or
(d) —C(=O)T₃; or
(e) —(C₁-C₅)alkyl, —(C₂-C₅)alkenyl, —(C₂-C₅)alkynyl, —(C₁-C₅)alkoxy, —(C₃-C₇)cycloalkyl, —(C₅-C₁₀)cycloalkenyl, or -(5- or 6-membered)heterocycle, each of which is unsubstituted or substituted with 1 or 2 independently selected R₅ groups;

a is an integer selected from 1, 2, or 3;
b is an integer selected from 1, 2, or 3;
each R₅ is independently selected from —(C₁-C₃)alkyl, —(C₂-C₃)alkenyl, —(C₂-C₃)alkynyl, —(C₁-C₃)alkyl-COOR₇, —OR₇, —SR₇, —C(halo)₃, —CH(halo)₂, —CH₂(halo), —CN, =O, =S, -halo, —N₃, —NO₂, —N(R₇)₂, —N(R₇)OH, —C(=O)R₇, —C(=O)OR₇, —OC(=O)R₇, —S(=O)R₇, or —S(=O)₂R₇;

each R₆ is independently selected from —(C₁-C₃)alkyl, —(C₂-C₃)alkenyl, —(C₂-C₃)alkynyl, —OR₇, —SR₇, —C(halo)₃, —CH(halo)₂, —CH₂(halo), —CN, -halo, —N₃, —NO₂, —N(R₇)₂, —N(R₇)OH, —C(=O)R₇, —C(=O)OR₇, —OC(=O)R₇, —S(=O)R₇, or —S(=O)₂R₇;

each R₇ is independently selected from —H, —CH₃, or —CH₂CH₃, each T₁, T₂, and T₃ is independently —H or —(C₁-C₅)alkyl which is unsubstituted or substituted with 1 or 2 independently selected R₅ groups; and each halo is independently selected from —F, —Cl, —Br, or —I.

In a further embodiment, the present invention relates to a compound having the following general formula (VII.2):

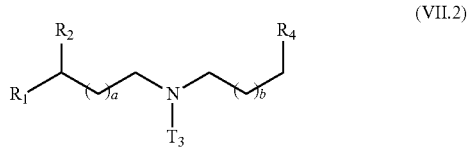

(VII.2)

or a pharmaceutically acceptable derivative thereof wherein:
R₁ is selected from -phenyl or -heteroaryl selected from the group consisting of pyridine, pyrazine, pyridazine and pyrimidine, each of which is unsubstituted or substituted with 1 or 2 independently selected R₆ groups;

R₂ is selected from —(C₁-C₄)alkyl, —(C₂-C₄)alkenyl, —(C₂-C₄)alkynyl, —(C₁-C₄)alkoxy, each of which is unsubstituted or substituted with 1 or 2 independently selected R₅ groups;

R₄ is selected from —N(T₁)(T₂), —N(T₃)N(T₁)(T₂), —N(T₃)C(=O)T₃, or —N(T₃)C(=O)OT₃;

a is an integer selected from 1 or 2;
b is an integer selected from 1 or 2;
each R₅ is independently selected from —H, —(C₁-C₂)alkyl, —(C₂)alkenyl, —(C₂)alkynyl, —OR₇, —SR₇, —C(halo)₃, —CH(halo)₂, —CH₂(halo), —CN, -halo, —N₃, —NO₂, —N(R₇)₂, —N(R₇)OH, —C(=O)R₇, —C(=O)OR₇, —S(=O)R₇, or —S(=O)₂R₇;

each R₆ is independently selected from —C(halo)₃, —CH(halo)₂, —CH₂(halo), or -halo;

each R₇ is independently selected from —H, or —CH₃; and each T₁, T₂, and T₃ is independently selected from —H or —CH₃; and each halo is independently selected from —F, —Cl, —Br, or —I.

In an optional embodiment, the present invention relates to a compound having the general formula (VII.2) or a pharmaceutically acceptable derivative thereof, wherein R₁ is -phenyl, which is unsubstituted or substituted with 1 or 2 independently selected R₆ groups.

In an optional embodiment, the present invention relates to a compound having the general formula (VII.2) or a pharmaceutically acceptable derivative thereof, wherein R₁ is -phenyl, which is unsubstituted or substituted with 1 or 2 independently selected groups selected from —C(Cl)₃, —CH(Cl)₂, —CH₂(Cl), or —Cl.

In an optional embodiment, the present invention relates to a compound having the general formula (VII.2) or a pharmaceutically acceptable derivative thereof, wherein

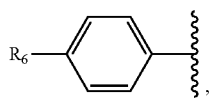

wherein $R_6$ is selected from —H, —C(Cl)$_3$, —CH(Cl)$_2$, —CH$_2$(Cl), or —Cl.

In an optional embodiment, the present invention relates to a compound having the general formula (VII.2) or a pharmaceutically acceptable derivative thereof, wherein $R_2$ is —(C$_1$-C$_4$)alkyl.

In an optional embodiment, the present invention relates to a compound having the general formula (VII.2) or a pharmaceutically acceptable derivative thereof, wherein $R_4$ is —N(T$_1$)(T$_2$), wherein each T$_1$, and T$_2$ is independently selected from —H or —CH$_3$.

In an optional embodiment, the present invention relates to a compound having the general formula (VII.2) or a pharmaceutically acceptable derivative thereof, wherein a=1 and b=1.

In an optional embodiment, the present invention relates to a compound having the general formula (VII.2) or a pharmaceutically acceptable derivative thereof, wherein halo is Cl.

Exemplified Compounds

In an optional embodiment, the present invention relates to the compounds depicted in Table 1 or a pharmaceutically acceptable derivative thereof.

TABLE 1

| Compound | Chemical structure |
|---|---|
| I.3 | 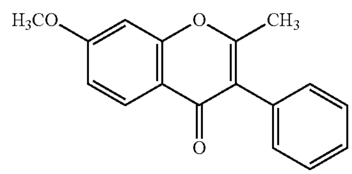 [SMILES: COc1ccc2c(=O)c(-c3ccccc3)c(C)oc2c1] |
| II.3 | 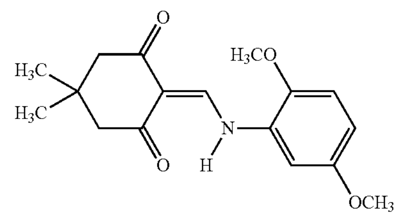 [SMILES: COc1ccc(OC)c(NC=C2C(=O)CC(C)(C)CC2=O)c1] |
| III.3 | 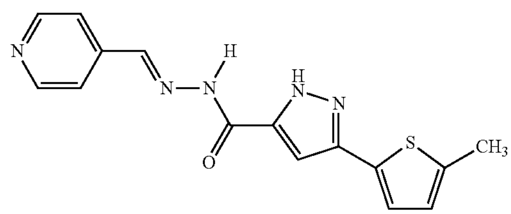 [SMILES: Cc1ccc(-c2cc(C(=O)N/N=C/c3ccncc3)[nH]n2)s1] |
| IV.3 | 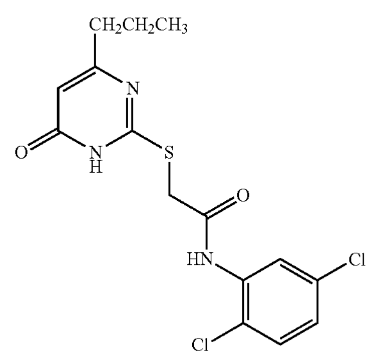 |
| V.3 | 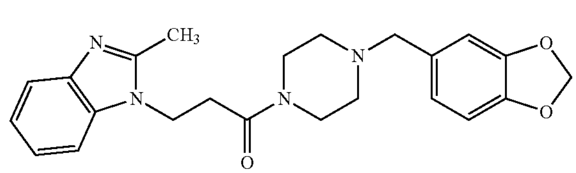 [SMILES: Cc1nc2ccccc2n1CCC(=O)N1CCN(Cc2ccc3c(c2)OCO3)CC1] |

TABLE 1-continued

| Compound | Chemical structure |
|---|---|
| VI.3 | 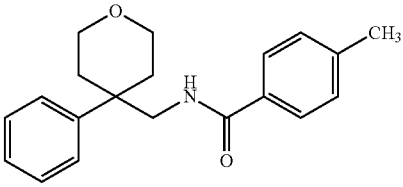 [SMILES: Cc1ccc(C(=O)NCC2(c3ccccc3)CCOCC2)cc1] |
| VII.3 | 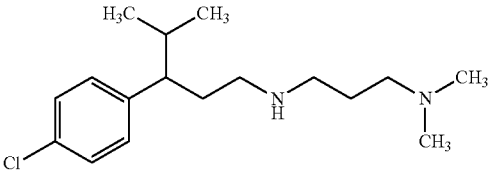 [SMILES: CC(C)C(CCNCCCN(C)C)c1ccc(Cl)cc1] |

In an optional embodiment, the present invention relates to a compound having the general formula (I.2) or a pharmaceutically acceptable derivative thereof, where Compound (I.3) is excluded.

In an optional embodiment, the present invention relates to a compound having the general formula (II.2) or a pharmaceutically acceptable derivative thereof, where Compound (II.3) is excluded.

In an optional embodiment, the present invention relates to a compound having the general formula (III.2) or a pharmaceutically acceptable derivative thereof, where Compound (III.3) is excluded.

In an optional embodiment, the present invention relates to a compound having the general formula (IV.2) or a pharmaceutically acceptable derivative thereof, where Compound (IV.3) is excluded.

In an optional embodiment, the present invention relates to a compound having the general formula (V.2) or a pharmaceutically acceptable derivative thereof, where Compound (V.3) is excluded.

In an optional embodiment, the present invention relates to a compound having the general formula (VI.2) or a pharmaceutically acceptable derivative thereof, where Compound (VI.3) is excluded.

In an optional embodiment, the present invention relates to a compound having the general formula (VII.2) or a pharmaceutically acceptable derivative thereof, where Compound (VII.3) is excluded.

DEFINITIONS

As used in connection with the Compounds herein, the terms used herein having following meaning:

When a first group is "substituted with one or more" second groups, one or more hydrogen atoms of the first group is replaced with a corresponding number of second groups. When the number of second groups is two or greater, each second group can be the same or different. In one embodiment, a first group is substituted with up to three second groups. In another embodiment, a first group is substituted with one or two second groups. In another embodiment, a first group is substituted with only one second group.

"—$(C_1-C_{10})$alkyl" means a straight chain or branched non-cyclic hydrocarbon having from 1 to 10 carbon atoms. Representative straight chain —$(C_1-C_{10})$alkyls include -methyl, -ethyl, -n-propyl, -n-butyl, -n-pentyl, -n-hexyl, -n-heptyl, -n-octyl, -n-nonyl, and -n-decyl. A branched alkyl means that one or more straight chain —$(C_1-C_8)$alkyl groups, such as methyl, ethyl or propyl, replace one or both hydrogens in a —$CH_2$— group of a straight chain alkyl. A branched non-cyclic hydrocarbon means that one or more straight chain —$(C_1-C_{10})$alkyl groups, such as methyl, ethyl or propyl, replace one or both hydrogens in a —$CH_2$— group of a straight chain non-cyclic hydrocarbon. Representative branched —$(C_1-C_{10})$alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

"—$(C_1-C_6)$alkyl" means a straight chain or branched non-cyclic hydrocarbon having from 1 to 6 carbon atoms. Representative straight chain —$(C_1-C_6)$alkyls include -methyl, -ethyl, -n-propyl, -n-butyl, -n-pentyl, and -n-hexyl. Representative branched —$(C_1-C_6)$alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl.

"—$(C_1-C_4)$alkyl" means a straight chain or branched non-cyclic hydrocarbon having from 1 to 4 carbon atoms. Representative straight chain —$(C_1-C_4)$alkyls include -methyl, -ethyl, -n-propyl, and -n-butyl. Representative branched —$(C_1-C_4)$alkyls include -iso-propyl, -sec-butyl, -iso-butyl, and -tert-butyl.

"—$(C_1-C_3)$alkyl" means a straight chain or branched non-cyclic hydrocarbon having from 1 to 3 carbon atoms. Representative straight chain —$(C_1-C_3)$alkyls include -methyl, -ethyl, and -n-propyl. Representative branched —$(C_1-C_3)$alkyls include -iso-propyl.

"—$(C_1-C_2)$alkyl" means a straight chain non-cyclic hydrocarbon having 1 or 2 carbon atoms. Representative straight chain —$(C_1-C_2)$alkyls include -methyl and -ethyl.

"—($C_2$-$C_{10}$)alkenyl" means a straight chain or branched non-cyclic hydrocarbon having from 2 to 10 carbon atoms and including at least one carbon-carbon double bond. A branched alkenyl means that one or more straight chain —($C_1$-$C_8$)alkyl groups, such as methyl, ethyl or propyl, replace one or both hydrogens in a —$CH_2$— or —CH= group of a straight chain alkenyl. Representative straight chain and branched ($C_2$-$C_{10}$)alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl, and the like.

"—($C_2$-$C_6$)alkenyl" means a straight chain or branched non-cyclic hydrocarbon having from 2 to 6 carbon atoms and including at least one carbon-carbon double bond. Representative straight chain and branched ($C_2$-$C_6$)alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, 2-hexenyl, 3-hexenyl, and the like.

"—($C_2$-$C_4$)alkenyl" means a straight chain or branched non-cyclic hydrocarbon having from 2 to 4 carbon atoms and including at least one carbon-carbon double bond. Representative ($C_2$-$C_4$)alkenyls include -vinyl, -allyl, -1-butenyl, -2-butenyl, -iso-butylenyl, and the like.

"—($C_2$-$C_3$)alkenyl" means a straight chain or branched non-cyclic hydrocarbon having from 2 to 3 carbon atoms and including at least one carbon-carbon double bond. Representative ($C_2$-$C_3$)alkenyls include -vinyl, -allyl, and the like.

"—($C_2$)alkenyl" means a straight chain non-cyclic hydrocarbon having 2 carbon atoms and including one carbon-carbon double bond.

"—($C_2$-$C_{10}$)alkynyl" means a straight chain or branched non-cyclic hydrocarbon having from 2 to 10 carbon atoms and including at least one carbon-carbon triple bond. A branched alkynyl means that one or more straight chain —($C_1$-$C_8$)alkyl groups, such as methyl, ethyl or propyl, replace one or both hydrogens in a —$CH_2$— group of a straight chain alkynyl. Representative straight chain and branched —($C_2$-$C_{10}$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like.

"—($C_2$-$C_6$)alkynyl" means a straight chain or branched non-cyclic hydrocarbon having from 2 to 6 carbon atoms and including at least one carbon-carbon triple bond. Representative straight chain and branched ($C_2$-$C_6$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, and the like.

"—($C_2$-$C_4$)alkynyl" means a straight chain or branched non-cyclic hydrocarbon having from 2 to 4 carbon atoms and including at least one carbon-carbon triple bond. Representative ($C_2$-$C_4$)alkynyls include -acetylenyl, -propynyl, -1-butynyl, -2-butynyl, and the like.

"—($C_2$-$C_3$)alkynyl" means a straight chain or branched non-cyclic hydrocarbon having from 2 to 3 carbon atoms and including at least one carbon-carbon triple bond. Representative ($C_2$-$C_3$)alkynyls include -acetylenyl, -propynyl, and the like.

"—($C_2$)alkynyl" means a straight chain non-cyclic hydrocarbon having 2 carbon atoms and including one carbon-carbon triple bond.

"—($C_1$-$C_6$)alkoxy" means a straight chain or branched non-cyclic hydrocarbon having one or more ether groups and from 1 to 6 carbon atoms. Representative straight chain and branched ($C_1$-$C_6$)alkoxys include -methoxy, -ethoxy, methoxymethyl, 2-methoxyethyl, -5-methoxypentyl, 3-ethoxybutyl and the like.

"—($C_1$-$C_4$)alkoxy" means a straight chain or branched non-cyclic hydrocarbon having one or more ether groups and from 1 to 4 carbon atoms. Representative ($C_1$-$C_4$) alkoxys include -methoxy, -ethoxy, methoxymethyl, 2-methoxyethyl, and the like.

"—($C_1$-$C_3$)alkoxy" means a straight chain or branched non-cyclic hydrocarbon having one or more ether groups and from 1 to 3 carbon atoms. Representative ($C_1$-$C_3$) alkoxys include -methoxy, -ethoxy, methoxymethyl, 2-methoxyethyl, and the like.

"—($C_3$-$C_{14}$)cycloalkyl" means a saturated monocyclic hydrocarbon having from 3 to 14 carbon atoms. Representative ($C_3$-$C_{14}$)cycloalkyls are -cyclopropyl, -cyclobutyl, -cyclopentyl, -cyclohexyl, -cycloheptyl, -cyclooctyl, -cyclononyl, -cyclodecyl, cycloundecyl, and -cyclododecyl, and -cyclotetradecyl.

"—($C_3$-$C_{12}$)cycloalkyl" means a saturated monocyclic hydrocarbon having from 3 to 12 carbon atoms. Representative ($C_3$-$C_{12}$)cycloalkyls are -cyclopropyl, -cyclobutyl, -cyclopentyl, -cyclohexyl, -cycloheptyl, -cyclooctyl, -cyclononyl, -cyclodecyl, cycloundecyl, and -cyclododecyl.

"—($C_6$-$C_{12}$)cycloalkyl" means a saturated monocyclic hydrocarbon having from 6 to 12 carbon atoms. Representative ($C_6$-$C_{12}$)cycloalkyls are -cyclohexyl, -cycloheptyl, -cyclooctyl, -cyclononyl, -cyclodecyl, cycloundecyl, and -cyclododecyl.

"—($C_4$-$C_8$)cycloalkyl" or "4- to 8-member cycloalkyl ring" means a saturated monocyclic hydrocarbon having from 4 to 8 carbon atoms. Representative —($C_4$-$C_8$)cycloalkyls are -cyclobutyl, -cyclopentyl, -cyclohexyl, -cycloheptyl, and -cyclooctyl.

"—($C_3$-$C_8$)cycloalkyl" means a saturated monocyclic hydrocarbon having from 3 to 8 carbon atoms. Representative ($C_3$-$C_8$)cycloalkyls include -cyclopropyl, -cyclobutyl, -cyclopentyl, -cyclohexyl, -cycloheptyl, and -cyclooctyl.

"—($C_3$-$C_7$)cycloalkyl" means a saturated monocyclic hydrocarbon having from 3 to 7 carbon atoms. Representative ($C_3$-$C_7$)cycloalkyls include cyclopropyl, -cyclobutyl, -cyclopentyl, -cyclohexyl, -cycloheptyl, and -cycloheptyl.

"—($C_6$-$C_{14}$)bicycloalkyl" means a bi-cyclic hydrocarbon ring system having from 6 to 14 carbon atoms and at least one saturated cyclic alkyl ring. Representative —($C_6$-$C_{14}$) bicycloalkyls include -indanyl, -norbornyl, -1,2,3,4-tetrahydronaphthalenyl, -5,6,7,8-tetrahydronaphthalenyl, -perhydronaphthalenyl, bicyclo[2.2.1]hexyl, bicyclo[2.2.1]heptyl, bicyclo[2.2.2]octyl, bicyclo[3.3.1]heptyl, bicyclo[3.2.1]octyl, bicyclo[3.3.1]nonyl, bicyclo[3.3.2]decyl, bicyclo[3.3.3]undecyl, bicyclo[4.2.2]decyl, bicyclo[4.3.2]undecyl, bicyclo[4.3.1]decyl, and the like.

"—($C_8$-$C_{20}$)tricycloalkyl" means a tri-cyclic hydrocarbon ring system having from 8 to 20 carbon atoms and at least one saturated cyclic alkyl ring. Representative —($C_8$-$C_{20}$) tricycloalkyls include -pyrenyl, -adamantyl, noradamantyl, -1,2,3,4-tetrahydroanthracenyl, -perhydroanthracenyl -aceanthrenyl, -1,2,3,4-tetrahydrophenanthrenyl, -5,6,7,8-tetrahydrophenanthrenyl, -perhydrophenanthrenyl, tetradecahydro-1H-cyclohepta[a]naphthalenyl, tetradecahydro-1H-cycloocta[e]indenyl, tetradecahydro-1H-cyclohepta[e]

azulenyl, hexadecahydrocycloocta[b]naphthalenyl, hexadecahydrocyclohepta[a]heptalenyl, tricyclo-pentadecanyl, tricyclo-octadecanyl, tricyclo-nonadecanyl, tricyclo-icosanyl, and the like.

"—$(C_3-C_{14})$cycloalkenyl" means a cyclic non-aromatic hydrocarbon having at least one carbon-carbon double bond in the cyclic system and from 3 to 14 carbon atoms. Representative $(C_3-C_{14})$cycloalkenyls include -cyclopropenyl, -cyclobutenyl, -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -cyclotetradecenyl, -cyclododecadienyl, and the like.

"—$(C_5-C_{14})$cycloalkenyl" means a cyclic non-aromatic hydrocarbon having at least one carbon-carbon double bond in the cyclic system and from 5 to 14 carbon atoms. Representative $(C_5-C_{14})$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -cyclotetradecenyl, -cyclododecadienyl, and the like.

"—$(C_6-C_{12})$cycloalkenyl" means a cyclic non-aromatic hydrocarbon having at least one carbon-carbon double bond in the cyclic system and from 6 to 12 carbon atoms. Representative $(C_6-C_{12})$cycloalkenyls include -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -cyclododecadienyl, and the like.

"—$(C_5-C_{10})$cycloalkenyl" means a cyclic non-aromatic hydrocarbon having at least one carbon-carbon double bond in the cyclic system and from 5 to 10 carbon atoms. Representative $(C_5-C_{10})$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyelooetatrienyl, cyclooctatetraenyl, -cyclononenyl, -cyclononadienyl, -cyclodecenyl, -cyclodecadienyl, and the like.

"—$(C_5-C_8)$cycloalkenyl" means a cyclic non-aromatic hydrocarbon having at least one carbon-carbon double bond in the cyclic system and from 5 to 8 carbon atoms. Representative $(C_5-C_8)$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, and the like.

"—$(C_7-C_{14})$bicycloalkenyl" means a bi-cyclic hydrocarbon ring system having at least one carbon-carbon double bond in each ring and from 7 to 14 carbon atoms. Representative —$(C_7-C_{14})$bicycloalkenyls include -bicyclo[3.2.0]hept-2-enyl, -indenyl, -pentalenyl, -naphthalenyl, -azulenyl, -heptalenyl, -1,2,7,8-tetrahydronaphthalenyl, norbornenyl, and the like.

"—$(C_8-C_{20})$tricycloalkenyl" means a tri-cyclic hydrocarbon ring system having at least one carbon-carbon double bond in each ring and from 8 to 20 carbon atoms. Representative —$(C_8-C_{20})$tricycloalkenyls include -anthracenyl, -phenanthrenyl, -phenalenyl, -acenaphthalenyl, as-indacenyl, s-indacenyl, 2,3,6,7,8,9,10,11-octahydro-1H-cycloocta[e]indenyl, 2,3,4,7,8,9,10,11-octahydro-1H-cyclohepta[a]naphthalenyl, 8,9,10,11-tetrahydro-7H-cyclohepta[a]naphthalenyl, 2,3,4,5,6,7,8,9,10,11,12,13-dodecahydro-1H-cyclohepta[a]heptalenyl, 1,2,3,4,5,6,7,8,9,10,11,12,13,14-tetradecahydro-dicyclohepta[a, c]cyclooctenyl, 2,3,4,5,6,7,8,9,10,11,12,13-dodecahydro-1H-dibenzo[a,c]cyclononenyl, and the like.

"-(3- to 7-membered)heterocycle" or "-(3- to 7-membered)heterocyclo" means a 3- to 7-membered monocyclic heterocyclic ring which is either saturated, unsaturated non-aromatic, or aromatic. A 3-membered heterocycle can contain up to 1 heteroatom, a 4-membered heterocycle can contain up to 2 heteroatoms, a 5-membered heterocycle can contain up to 4 heteroatoms, a 6-membered heterocycle can contain up to 4 heteroatoms, and a 7-membered heterocycle can contain up to 5 heteroatoms. Each heteroatom is independently selected from nitrogen, which can be quaternized; oxygen; and sulfur, including sulfoxide and sulfone. The -(3- to 7-membered)heterocycle can be attached via a nitrogen or carbon atom. Representative -(3- to 7-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

"-(5- or 6-membered)heterocycle" or "-(5- or 6-membered)heterocyclo" means a 5- or 6-membered monocyclic heterocyclic ring which is either saturated, unsaturated non-aromatic, or aromatic. A 5-membered heterocycle can contain up to 4 heteroatoms and a 6-membered heterocycle can contain up to 4 heteroatoms. Each heteroatom is independently selected from nitrogen, which can be quaternized; oxygen; and sulfur, including sulfoxide and sulfone. The -(5- or 6-membered)heterocycle can be attached via a nitrogen or carbon atom. Representative -(5- or 6-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, tetrahydrofuranyl, tetrahydropyranyl, dihydropyridinyl, tetrahydropyridinyl, tetrahydropyrimidinyl, tetrahydrothiophenyl, tetrahydrothiopyranyl, tetrazolyl, and the like.

"-(3- to 5-membered)heterocycle" or "-(3- to 5-membered)heterocyclo" means a 3- to 5-membered monocyclic heterocyclic ring which is either saturated, unsaturated non-aromatic, or aromatic. A 3-membered heterocycle can contain up to 1 heteroatom, a 4-membered heterocycle can contain up to 2 heteroatoms, and a 5-membered heterocycle can contain up to 4 heteroatoms. Each heteroatom is independently selected from nitrogen, which can be quaternized; oxygen; and sulfur, including sulfoxide and sulfone. The -(3- to 5-membered)heterocycle can be attached via a nitrogen or carbon atom. Representative -(3- to 5-membered)heterocycles include furyl, thiophenyl, pyrrolyl, oxazolyl, imidazolyl, thiazolidinyl, thiadiazolyl, thiazolyl, isoxazolyl, pyrazolyl, isothiazolyl, triazinyl, pyrrolidinonyl, pyrrolidinyl, 2,3-dihydrofuranyl, hydantoinyl, oxiranyl, oxetanyl, tetrahydrofuranyl, tetrahydrothiophenyl, pyrazolidinyl and the like.

"-(7- to 10-membered)bicycloheterocycle" or "-(7- to 10-membered)bicycloheterocyclo" means a 7- to 10-membered bicyclic, heterocyclic ring which is either saturated, unsaturated non-aromatic, or aromatic. A -(7- to 10-membered)bicycloheterocycle contains from 1 to 4 heteroatoms independently selected from nitrogen, which can be quaternized; oxygen; and sulfur, including sulfoxide and sulfone. The -(7- to 10-membered)bicycloheterocycle can be attached via a nitrogen or carbon atom. Representative -(7- to 10-membered)bicycloheterocycles include -quinolinyl, -isoquinolinyl, -chromonyl, -coumarinyl, -indolyl, -indolizinyl, -benzo[b]furanyl, -benzo[b]thiophenyl, -indazolyl, -purinyl, -4H-quinolizinyl, -isoquinolyl, -quinolyl, -phthalazinyl, -naphthyridinyl, -carbazolyl, -β-carbolinyl, -indolinyl, -isoindolinyl, -1,2,3,4-tetrahydroquinolinyl, -1,2,3,4-tetrahydroisoquinolinyl, pyrrolopyrrolyl and the like.

"—($C_3$-$C_{12}$)cycloalkoxy" means a saturated monocyclic hydrocarbon having from 3 to 12 carbon atoms where at least one of the carbon atoms is replaced by an oxygen atom. Representative ($C_3$-$C_{12}$)cycloalkoxy are -oxiranyl, -oxetanyl, -tetrahydrofuranyl, -tetrahydro-2H-pyranyl, -1,4-dioxanyl, -oxepanyl, -1,4-dioxepanyl, -oxocanyl, -1,5-dioxocanyl, -1,3,5-trioxocanyl, -oxonanyl, -1,5-dioxonanyl, -1,4,7-trioxonanyl, -oxacyclododecanyl, -1,7-dioxacyclododecanyl, and -1,5,9-trioxacyclododecanyl.

"—($C_3$-$C_7$)cycloalkoxy" means a saturated monocyclic hydrocarbon having from 3 to 7 carbon atoms where at least one of the carbon atoms is replaced by an oxygen atom. Representative ($C_3$-$C_7$)cycloalkoxy are -oxiranyl, -oxetanyl, -tetrahydrofuranyl, -tetrahydro-2H-pyranyl, -1,4-dioxanyl, -oxepanyl, and -1,4-dioxepanyl.

"—($C_{14}$)aryl" means a 14-membered aromatic carbocyclic moiety such as -anthryl or -phenanthryl.

"-(5- to 10-membered)heteroaryl" means an aromatic heterocycle ring of 5 to 10 members, including both mono- and bicyclic ring systems, where at least one carbon atom of one or both of the rings is replaced with a heteroatom independently selected from nitrogen, oxygen, and sulfur, or at least two carbon atoms of one or both of the rings are replaced with a heteroatom independently selected from nitrogen, oxygen, and sulfur. In one embodiment, one of the -(5- to 10-membered)heteroaryl's rings contain at least one carbon atom. In another embodiment, both of the -(5- to 10-membered)heteroaryl's rings contain at least one carbon atom. Representative -(5- to 10-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, cinnolinyl, phthalazinyl, and quinazolinyl.

"-(5- or 6-membered)heteroaryl" means a monocyclic aromatic heterocycle ring of 5 or 6 members where at least one carbon atom is replaced with a heteroatom independently selected from nitrogen, oxygen, and sulfur. In one embodiment, one of the -(5- or 6-membered)heteroaryl's ring contains at least one carbon atom. Representative -(5- or 6-membered)heteroaryls include pyridyl, furyl, pyrrolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, and thiophenyl.

"—$CH_2$(halo)" means a methyl group where one of the hydrogens of the methyl group has been replaced with a halogen. Representative —$CH_2$(halo) groups include —$CH_2$F, —$CH_2$Cl, —$CH_2$Br, and —$CH_2$I.

"—CH(halo)$_2$" means a methyl group where two of the hydrogens of the methyl group have been replaced with a halogen. Representative —CH(halo)$_2$ groups include —$CHF_2$, —$CHCl_2$, —$CHBr_2$, —CHBrCl, —CHClI, and —$CHI_2$.

"—C(halo)$_3$" means a methyl group where each of the hydrogens of the methyl group has been replaced with a halogen. Representative —C(halo)$_3$ groups include —$CF_3$, —$CCl_3$, —$CBr_3$, and —$CI_3$.

"-Halogen" or "-halo" means —F, —Cl, —Br, or —I.

"Oxo", "=O", and the like as used herein mean an oxygen atom doubly bonded to carbon or another element.

"Thiooxo", "thioxo", "=S", and the like as used herein mean a sulfur atom doubly bonded to carbon or another element.

"Imino", "=$NT_3$", and the like as used herein mean a nitrogen atom doubly bonded to carbon or another element.

As used herein in connection with Formula (I), when the dashed line in the 6-membered ring that is fused to the Q group is absent, then Formula (I) is understood to appear as follows

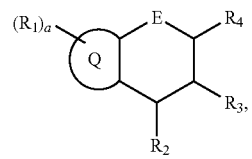

i.e., the 6-membered ring that is fused to the Q group contains no double bond between the ring-carbon to which the $R_3$ group is attached and the adjacent carbon atom to which the $R_4$ is attached.

As used herein in connection with Formula (I), when the dashed line in the 6-membered, nitrogen-containing ring that is fused to the Q group indicates the presence of a bond, then Formula (I) is understood to appear as follows

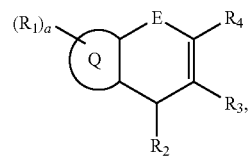

i.e., the 6-membered ring that is fused to the Q group contains a double bond between the ring-carbon to which the $R_3$ group is attached and the adjacent carbon atom to which the $R_4$ is attached.

As used herein in connection with Formula (I.1), when the dashed line in the 6-membered ring that is fused to the Q group is absent, then Formula (I.1) is understood to appear as follows

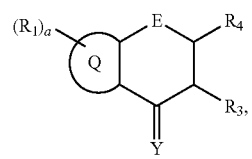

i.e., the 6-membered ring that is fused to the Q group contains no double bond between the ring-carbon to which the $R_3$ group is attached and the adjacent carbon atom to which the $R_4$ is attached.

As used herein in connection with Formula (I.1), when the dashed line in the 6-membered, nitrogen-containing ring that is fused to the Q group indicates the presence of a bond, then Formula (I.1) is understood to appear as follows

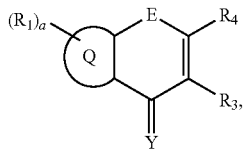

i.e., the 6-membered ring that is fused to the Q group contains a double bond between the ring-carbon to which the $R_3$ group is attached and the adjacent carbon atom to which the $R_4$ is attached.

As used herein in connection with Formula (II), when the dashed line is absent, then Formula (II) is understood to appear as follows

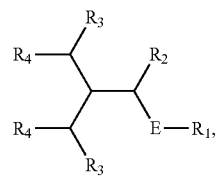

i.e., the Formula contains no double bond between the carbon atom to which the $R_2$ group and E are attached and the adjacent carbon atom.

As used herein in connection with Formula (II), when the dashed line is absent, then Formula (II) is understood to appear as follows

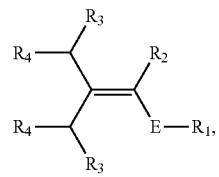

i.e., the Formula contains a double bond between the carbon atom to which the $R_2$ group and E are attached and the adjacent carbon atom.

"$(C_2-C_6)$bridge" as used in connection with Formulas (II) and (II.1) means a hydrocarbon chain containing 2 to 6 carbon atoms joining the two carbon atoms connected to $R_4$ according to Formulas (II) and (II.1) to form a cyclic ring system. Exemplary compounds of the invention include those with a $(C_2)$bridge, —$CH_2$—$CH_2$—, joining the two carbon atoms connected to $R_4$; a $(C_3)$bridge, —$CH_2$—$CH_2$—$CH_2$—, joining the two carbon atoms connected to $R_4$; a $(C_4)$bridge, —$CH_2$—$CH_2$—$CH_2$—$CH_2$—, joining the two carbon atoms connected to $R_4$; a $(C_5)$bridge, —$CH_2$—$CH_2$—$CH_2$—$CH_2$—$CH_2$—, joining the two carbon atoms connected to $R_4$; or a $(C_6)$bridge, —$CH_2$—$CH_2$—$CH_2$—$CH_2$—$CH_2$—$CH_2$—, joining the two carbon atoms connected to $R_4$. Examples of a $(C_2-C_6)$bridge which optionally contains —HC=CH— within the $(C_2-C_6)$bridge include —HC=CH—, —$CH_2$—HC=CH—, —HC=CH—$CH_2$—, —$CH_2$—HC=CH—$CH_2$—, and the like. Examples of a $(C_2-C_6)$bridge which optionally contains —O— within the $(C_2-C_6)$bridge include —$CH_2$—O—$CH_2$— (containing 2 carbon atoms), —$CH_2$—O—$CH_2$—$CH_2$— and —$CH_2$—$CH_2$—O—$CH_2$— (each containing 3 carbon atoms), —$CH_2$—$CH_2$—O—$CH_2$—$CH_2$—, —$CH_2$—O—$CH_2$—$CH_2$—$CH_2$— and —$CH_2$—$CH_2$—$CH_2$—O—$CH_2$— (each containing 4 carbon atoms), and the like.

As used herein in connection with Formula (II.1), when the dashed line is absent, then Formula (II.1) is understood to appear as follows

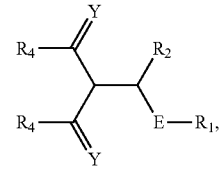

i.e., the Formula contains no double bond between the carbon atom to which the $R_2$ group and E are attached and the adjacent carbon atom.

As used herein in connection with Formula (II.1), when the dashed line is absent, then Formula (II.1) is understood to appear as follows

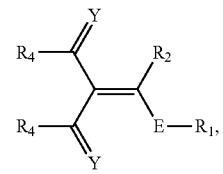

i.e., the Formula contains a double bond between the carbon atom to which the $R_2$ group and E are attached and the adjacent carbon atom.

As used herein in connection with Formula (II.2), when the dashed line is absent, then Formula (II.2) is understood to appear as follows

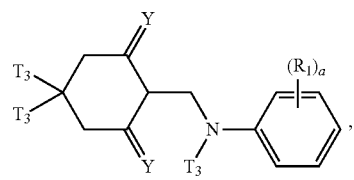

i.e., the Formula contains no double bond between the carbon atom to which the nitrogen is attached and the adjacent carbon atom comprised by the 6-membered ring.

As used herein in connection with Formula (II.2), when the dashed line is absent, then Formula (II.2) is understood to appear as follows

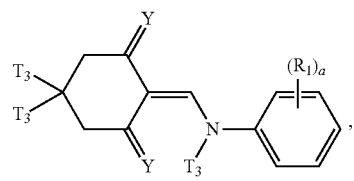

i.e., the Formula contains a double bond between the carbon atom to which the nitrogen is attached and the adjacent carbon atom comprised by the 6-membered ring.

As used herein in connection with Formula (III), when the dashed line is absent, then Formula (III) is understood to appear as follows

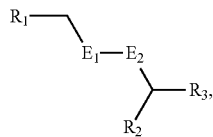

i.e., the Formula contains no double bond between the carbon atom to which $R_1$ is attached and the adjacent $E_1$ group.

As used herein in connection with Formula (III), when the dashed line is absent, then Formula (III) is understood to appear as follows

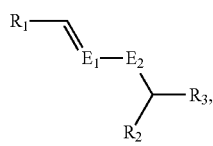

i.e., the Formula contains a double bond between the carbon atom to which $R_1$ is attached and the adjacent $E_1$ group.

As used herein in connection with Formula (IV), when the dashed line is absent, then Formula (IV) is understood to appear as follows

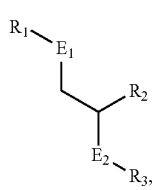

i.e., the Formula contains no double bond between the carbon atom to which $E_1$ is attached and the adjacent carbon atom to which $R_2$ and $E_2$ are attached.

As used herein in connection with Formula (IV), when the dashed line is absent, then Formula (IV) is understood to appear as follows

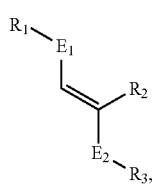

i.e., the Formula contains a double bond between the carbon atom to which $E_1$ is attached and the adjacent carbon atom to which $R_2$ and $E_2$ are attached.

As used herein in connection with Formula (IV.1), when both dashed lines are absent, then Formula (IV.1) is understood to appear as follows

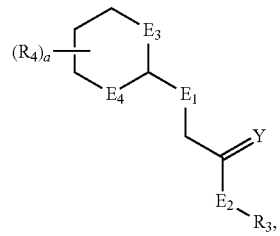

i.e., the Formula contains no double bond in the 6-membered ring containing $E_3$ and $E_4$.

As used herein in connection with Formula (IV.1), when one dashed line is absent, then Formula (IV.1) is understood to appear as follows

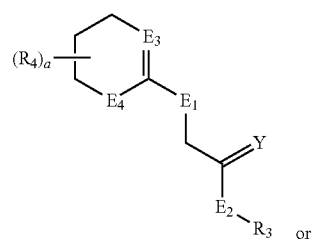

i.e., the Formula contains one double bond in the 6-membered ring containing $E_3$ and $E_4$.

As used herein in connection with Formula (IV.1), when both dashed lines are present, then Formula (IV.1) is understood to appear as follows

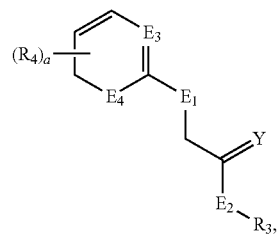

i.e., the Formula contains two double bonds in the 6-membered ring containing $E_3$ and $E_4$.

As used herein in connection with Formula (V.1), when the dashed line is absent, then Formula (V.1) is understood to appear as follows

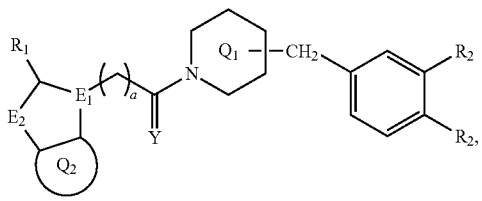

i.e., the Formula contains no double bond in the 5-membered ring containing $E_1$ and $E_2$.

As used herein in connection with Formula (V.1), when the dashed line is present, then Formula (V.1) is understood to appear as follows

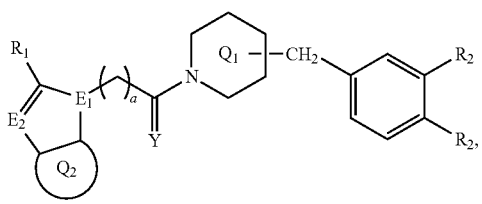

i.e., the Formula contains a double bond in the 5-membered ring containing $E_1$ and $E_2$.

The phrase "benzo", "benzo group" and the like, when used in connection with the optionally-substituted Q group in Formulas (I) and (I.1), means

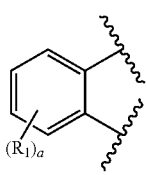

where $R_1$ and a are defined above for the compounds of Formulas (I) and (I.1).

The phrase "(5- or 6-membered)heteroaryl" when used in connection with the optionally-substituted Q group in Formula (I), means

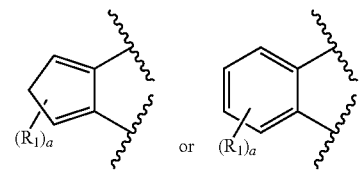

where at least one carbon atom is replaced with a heteroatom independently selected from nitrogen, oxygen, and sulfur and $R_1$ and a are defined above for the compounds of Formula (I). Representative -(5- or 6-membered)heteroaryls include pyridyl, furyl, pyrrolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, and thiophenyl.

The phrase "6-membered heteroaryl" when used in connection with the optionally-substituted Q group in Formula (I.1), means

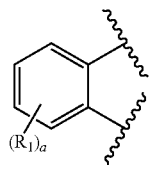

where at least one carbon atom is replaced with a nitrogen, and $R_1$ and a are defined above for the compounds of Formula (I.1). Representative 6-membered heteroaryls include pyridyl, pyridazinyl, pyrimidyl, pyrazinyl, and the like.

The phrase "pyridine", "pyridino group" and the like, when used in connection with the optionally-substituted Q group in Formulas (I) and (I.1), means

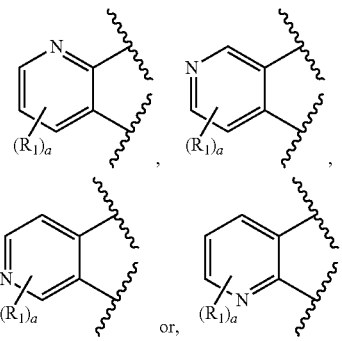

where $R_1$ and a are defined above for the Compounds of Formulas (I) and (I.1).

The phrase "pyrimidino", "pyrimidino group" and the like, when used in connection with the optionally-substituted Q group in Formulas (I) and (I.1), means

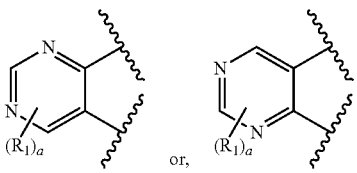

where $R_1$ and a are defined above for the Compounds of Formulas (I) and (I.1).

The phrase "pyrazino", "pyrazino group" and the like, when used in connection with the optionally-substituted Q group in Formulas (I) and (I.1), means

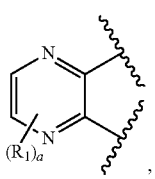

where $R_1$ and a are defined above for the Compounds of Formulas (I) and (I.1).

The phrase "pyridazino", "pyridazino group" and the like, when used in connection with the optionally-substituted Q group in Formulas (I) and (I.1), means

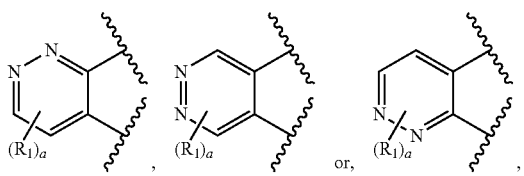

where $R_1$ and a are defined above for the Compounds of Formulas (I) and (I.1).

The phrase "pyridine", "pyridino group" and the like, when used in connection with the optionally-substituted $R_3$ group in Formula (I.2) or with the optionally-substituted $R_1$ group in Formula (III.2) or with the optionally-substituted $R_3$ group in Formula (IV.2) or with the optionally-substituted $R_1$ group in Formula (VI.2) or with the optionally-substituted $R_1$ group in Formula (VII.2), means

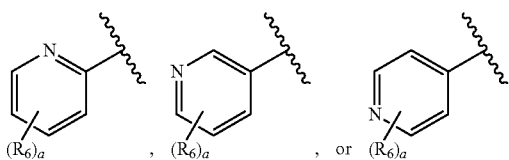

where $R_6$ is defined above for the compounds of Formulas (I.2) or (III.2) or (IV.2) or (VI.2) or (VII.2), respectively, and a is an integer selected from 1 or 2.

The phrase "pyrimidine", "pyrimidino group" and the like, when used in connection with the optionally-substituted $R_3$ group in Formula (I.2) or with the optionally-substituted $R_1$ group in Formula (III.2) or with the optionally-substituted $R_3$ group in Formula (IV.2) or with the optionally-substituted $R_1$ group in Formula (VI.2) or with the optionally-substituted $R_1$ group in Formula (VII.2), means

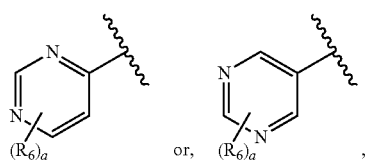

where $R_6$ is defined above for the compounds of Formula (I.2) or (III.2) or (IV.2) or (VI.2) or (VII.2), respectively, and a is an integer selected from 1 or 2.

The phrase "pyrazine", "pyrazino group" and the like, when used in connection with the optionally-substituted $R_3$ group in Formula (I.2) or with the optionally-substituted $R_1$ group in Formula (III.2) or with the optionally-substituted $R_3$ group in Formula (IV.2) or with the optionally-substituted $R_1$ group in Formula (VI.2) or with the optionally-substituted $R_1$ group in Formula (VII.2), means

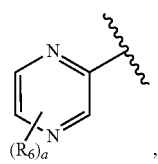

where $R_6$ is defined above for the compounds of Formula (I.2) or (III.2) or (IV.2) or (VI.2) or (VII.2), respectively, and a is an integer selected from 1 or 2.

The phrase "pyridazine", "pyridazino group" and the like, when used in connection with the optionally-substituted $R_3$ group in Formula (I.2) or with the optionally-substituted $R_1$ group in Formula (III.2) or with the optionally-substituted $R_3$ group in Formula (IV.2) or with the optionally-substituted $R_1$ group in Formula (VI.2) or with the optionally-substituted $R_1$ group in Formula (VII.2), means

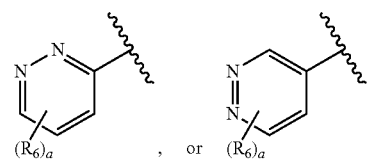

where $R_6$ is defined above for the compounds of Formula (I.2) or (III.2) or (IV.2) or (VI.2) or (VII.2), respectively, and a is an integer selected from 1 or 2.

The phrase "$(C_6)$cycloalkyl" when used in connection with the optionally-substituted $Q_1$ group in Formula (V), means

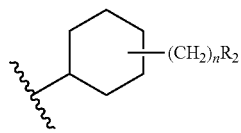

where $R_2$ is defined above for the compounds of Formula (V).

The phrase "$(C_6)$cycloalkenyl" when used in connection with the optionally-substituted $Q_1$ group in Formula (V), means

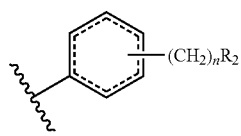

where the cyclic non-aromatic hydrocarbon has at least one carbon-carbon double bond in the cyclic system and where $R_2$ is defined above for the compounds of Formula (V).

The phrase "(6-membered)heterocycle" when used in connection with the optionally-substituted $Q_1$ group in Formula (V), means

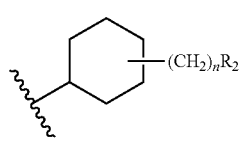

where at least one carbon atom in the ring is replaced with a heteroatom independently selected from nitrogen, oxygen, and sulfur, and where $R_2$ is defined above for the compounds of Formula (V).

The phrase "(6-membered)heteroaryl" when used in connection with the optionally-substituted $Q_1$ group in Formula (V), means

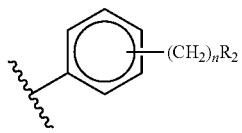

where at least one carbon atom in the ring is replaced with a nitrogen, and where $R_2$ is defined above for the compounds of Formula (V).

The phrase "(6-membered)heterocycle" when used in connection with the optionally-substituted $Q_1$ group in Formula (V.1), means

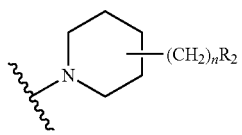

where at least one further carbon atom in the ring can be replaced with a heteroatom independently selected from nitrogen, oxygen, and sulfur, and where $R_2$ is defined above for the compounds of Formula (V.1).

The phrase "(6-membered)heteroaryl" when used in connection with the optionally-substituted $Q_1$ group in Formula (V.1), means

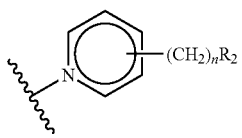

where at least one further carbon atom in the ring can be replaced with a nitrogen, and where $R_2$ is defined above for the compounds of Formula (V.1).

The phrase "benzo", "benzo group" and the like, when used in connection with the optionally-substituted $Q_2$ group in Formula (V.1), means

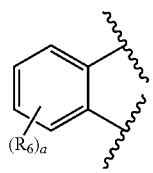

where $R_6$ and a are defined above for the compounds of Formula (V.1).

The phrase "(6-membered)heteroaryl" when used in connection with the optionally-substituted $Q_2$ group in Formula (V.1), means

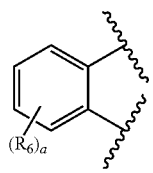

where at least one carbon atom is replaced with a nitrogen, and $R_6$ and a are defined above for the compounds of Formula (V.1). Representative (6-membered)heteroaryls include pyridyl, pyridazinyl, pyrimidyl, and pyrazinyl.

The phrase "pyridine", "pyridino group" and the like, when used in connection with the optionally-substituted $Q_2$ group in Formula (V.1), means

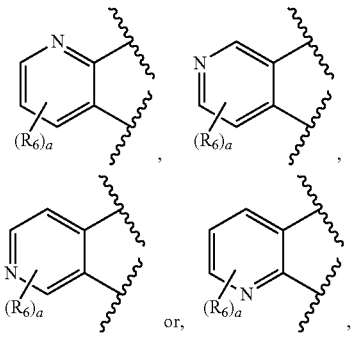

where $R_6$ and a are defined above for the Compounds of Formula (V.1).

The phrase "pyrimidino", "pyrimidino group" and the like, when used in connection with the optionally-substituted $Q_2$ group in Formula (V.1), means

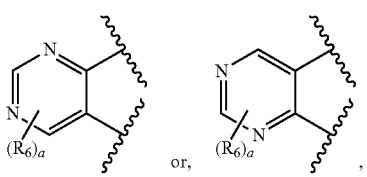

where $R_6$ and a are defined above for the Compounds of Formula (V.1).

The phrase "pyrazino", "pyrazino group" and the like, when used in connection with the optionally-substituted $Q_2$ group in Formula (V.1), means

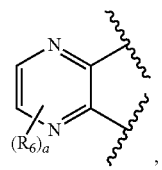

where $R_6$ and a are defined above for the Compounds of Formula (V.1).

The phrase "pyridazino", "pyridazino group" and the like, when used in connection with the optionally-substituted $Q_2$ group in Formula (V.1), means

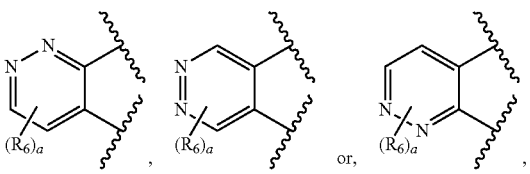

where $R_6$ and a are defined above for the Compounds of Formula (V.1).

"(2- to 6-membered)bridge" as used in connection with Formula (V.1) means a hydrocarbon chain containing 1 to 6 carbon atoms joining the two atoms of the phenyl ring of Formula (V.1) connected to $R_2$ to form a fused bicyclic ring system. For example, compounds of the invention can comprise a $(C_2-C_6)$bridge joining the two positions of the ring. Exemplary compounds of the invention include those with a $(C_2)$bridge, —$CH_2$—$CH_2$—; a $(C_3)$bridge, —$CH_2$—$CH_2$—$CH_2$—; a $(C_4)$bridge, —$CH_2$—$CH_2$—$CH_2$—$CH_2$—; a $(C_5)$bridge, —$CH_2$—$CH_2$—$CH_2$—$CH_2$—$CH_2$—; or a $(C_6)$bridge, —$CH_2$—$CH_2$—$CH_2$—$CH_2$—$CH_2$—$CH_2$—. Examples of a (2- to 6-membered)bridge which optionally contains —O— within the bridge include —O—$CH_2$—O— (containing 1 carbon atom), —$CH_2$—O—$CH_2$— (containing 2 carbon atoms), —$CH_2$—O—$CH_2$—$CH_2$— and —$CH_2$—$CH_2$—O—$CH_2$— (each containing 3 carbon atoms), —$CH_2$—$CH_2$—O—$CH_2$—$CH_2$—, —$CH_2$—O—$CH_2$—$CH_2$—$CH_2$— and —$CH_2$—$CH_2$—$CH_2$—O—$CH_2$— (each containing 4 carbon atoms), and the like.

"(2- to 6-membered)bridge" as used in connection with Formulas (VI) and (VI.1) means a hydrocarbon chain containing 1 to 6 carbon atoms to form a cyclic ring system connected through just one atom, i.e. the carbon atom connected to $R_1$ is comprised by the cyclic ring system. For example, compounds of the invention can comprise a $(C_2-C_6)$bridge joining the two positions of the ring. Exemplary compounds of the invention include those with a $(C_2)$bridge, —$CH_2$—$CH_2$—; a $(C_3)$bridge, —$CH_2$—$CH_2$—$CH_2$—; a $(C_4)$bridge, —$CH_2$—$CH_2$—$CH_2$—$CH_2$—; a $(C_5)$bridge, —$CH_2$—$CH_2$—$CH_2$—$CH_2$—$CH_2$—; or a $(C_6)$bridge, —$CH_2$—$CH_2$—$CH_2$—$CH_2$—$CH_2$—$CH_2$—. Examples of a (2- to 6-membered)bridge which optionally contains a heteroatom selected from nitrogen, oxygen and sulfur within the bridge include —$CH_2$—O—$CH_2$—$CH_2$— and —$CH_2$—S—$CH_2$—$CH_2$— (each containing 3 carbon atoms), —$CH_2$—$CH_2$—O—$CH_2$—$CH_2$—, —$CH_2$—$CH_2$—S—$CH_2$—$CH_2$—, —$CH_2$—O—$CH_2$—$CH_2$—$CH_2$— and —$CH_2$—$CH_2$—$CH_2$—O—$CH_2$— (each containing 4 carbon atoms), and the like.

The term "animal" includes, but is not limited to, a human or a non-human animal, such as a companion animal or livestock, e.g., a cow, monkey, baboon, chimpanzee, horse, sheep, pig, chicken, turkey, quail, cat, dog, mouse, rat, rabbit or guinea pig.

Preferably, the compounds of the present invention selectively modulate vertebrate TRPM8, more preferably they selectively modulate mammalian TRPM8 and most preferably they selectively modulate human TRPM8.

The phrase "pharmaceutically acceptable derivative", as used herein, includes any pharmaceutically acceptable salt, solvate, prodrug, radiolabeled, stereoisomer, enantiomer, diastereomer, other stereoisomeric form, racemic mixture, geometric isomer, and/or tautomer, e.g., of a compound disclosed herein. In one embodiment, the pharmaceutically acceptable derivative is a pharmaceutically acceptable salt, solvate, radiolabeled, stereoisomer, enantiomer, diastereomer, other stereoisomeric form, racemic mixture, geometric isomer, and/or tautomer, e.g., of a compound disclosed herein. In another embodiment, the pharmaceutically acceptable derivative is a pharmaceutically acceptable salt, e.g., of a compound disclosed herein.

The phrase "pharmaceutically acceptable salt", as used herein, is any pharmaceutically acceptable salt that can be prepared from a compound disclosed herein including a salt formed from an acid and a basic functional group, such as a nitrogen group, of a compound disclosed herein. Illustrative salts include, but are not limited, to sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt prepared from a compound disclosed herein having an acidic functional group, such as a carboxylic acid functional group, and a pharmaceutically acceptable inorganic or organic base. Suitable bases include, but are not limited to, hydroxides of alkali metals such as sodium, potassium, cesium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; picoline; N-methyl, N-ethylamine; diethylamine; triethylamine; mono-, bis-, or tris-(2-hydroxy-$(C_1-C_3)$alkyl amines), such as mono-, bis-, or tris-(2-hydroxyethyl)amine, 2-hydroxy-tert-butylamine, or tris-(hydroxymethyl)methylamine, N,N-di-[$(C_1-C_3)$alkyl]-N-(hydroxy-$(C_1-C_3)$alkyl)-amines, such as N,N-dimethyl-N-(2-hydroxyethyl)amine, or tri-(2-hydroxyethyl)amine; N-methyl-D-glucamine; and amino acids such as arginine, lysine, and the like. One skilled in the art will recognize that, e.g., acid addition salts of a compound disclosed herein can be prepared by reaction of the compounds with the appropriate acid via a variety of known methods.

A compound disclosed herein can contain one or more asymmetric centers and can thus give rise to enantiomers, diastereomers, and other stereoisomeric forms. The invention is also meant to encompass all such possible forms as well as their racemic and resolved forms or any mixture thereof. When a compound disclosed herein contains an olefinic double bond or other center of geometric asymmetry, and unless specified otherwise, it is intended to include all "geometric isomers", e.g., both E and Z geometric isomers. All "tautomers", e.g., ketone-enol, amide-imidic acid, lactam-lactim, enamine-imine, amine-imine, and enamine-enimine tautomers, are intended to be encompassed by the invention as well.

As used herein, the terms "stereoisomer", "stereoisomeric form", and the like are general terms for all isomers of individual molecules that differ only in the orientation of their atoms in space. It includes enantiomers and isomers of compounds with more than one chiral center that are not mirror images of one another ("diastereomers").

The term "chiral center" refers to a carbon atom to which four different groups are attached.

The term "enantiomer" or "enantiomeric" refers to a molecule that is nonsuperimposeable on its mirror image and hence optically active where the enantiomer rotates the plane of polarized light in one direction and its mirror image rotates the plane of polarized light in the opposite direction.

The term "racemic" refers to a mixture of equal parts of enantiomers which is optically inactive.

The term "resolution" refers to the separation or concentration or depletion of one of the two enantiomeric forms of a molecule.

Optical isomers of a compound disclosed herein can be obtained by known techniques such as chiral chromatography or formation of diastereomeric salts from an optically active acid or base.

The phrases "treatment of", "treating", and the like include the amelioration or cessation of a condition or a symptom thereof. In one embodiment, treating includes inhibiting, for example, decreasing the overall frequency of episodes of a condition or a symptom thereof. The phrases "prevention of", "preventing", and the like include the avoidance of the onset of a condition or a symptom thereof. A "disorder" includes, but is not limited to, the conditions defined above.

The term "half maximal effective concentration" or "$EC_{50}$" refers to the concentration of a compound disclosed herein which induces a response on a channel halfway between the baseline and maximum after some specified exposure time. The $EC_{50}$ of a graded dose response curve therefore represents the concentration of a compound where 50% of its maximal effect (which may be either agonistic or antagonistic) on the respective channel is observed.

Preparation of the Compounds

The compounds disclosed herein are either commercially available or can be made using conventional organic synthesis which are known to the person skilled in the art.

Screening Method

As part of the invention, compound libraries can be employed comprising compounds to be tested for having modulating activity for one or more members of the transient receptor potential cation channel families. The methods of the invention can employ such compound libraries e.g. for identifying suitable modulators of TRPM8 and/or any further member of the transient receptor potential cation channel families.

In the context of the present invention, the term "chemical library" means a collection of chemical compounds. A "chemical library" employed in the present invention will comprise at least 2 different compounds, rarely less than about 5 compounds, usually at least about 10 compounds, frequently will have about 50 compounds or more, usually more than about 500 compounds such as about 15,000 compounds or more.

The activity of the compounds comprised by such compound libraries on TRPM8 or TRPA1 (or any further member of the transient receptor potential cation channel families) can be evaluated in a functional cell based assay. In such "functional cell based assays" a compound-channel interaction can lead to a functional response of the cell. The physiological response of the cell, initiated by a screening compound can be quantified by using recombinant reporter technology. It is known in the art that the TRP channels are a family of ion channel proteins that mediate ion influx of $Na^+$ and $Ca^{2+}$ and, in several cases, $Mg^{2+}$. In the case of TRPM8, assembly of the channel subunits as tetramers results in the formation of cation-selective channels that permeate calcium ions. Upon activation, a signal transduction cascade is mediated by TRPM8, producing the perception of cold in the nervous system. For instance, the action of menthol on TRPM8 provides the "cool" sensation via activation of the channel and subsequent increase of intracellular calcium ions in cells expressing the channel. This calcium influx can be used as read-out in functional cell based assays.

The sequences that encode the members of the transient receptor potential cation channel families are available to the person skilled in the art (cf. National Center for Biotechnology Information website: http://www.ncbi.nlm.nih.gov). The methods of amplifying and cloning such sequences (e.g., by PCR) are also commonly known in the art. According to an optional embodiment, TRPM8 (human) has the nucleic acid or amino acid sequence as disclosed in GenBank Accession Number NM_024080 or NP_076985.4 and TRPA1 (human) has the nucleic acid or amino acid sequence as disclosed in GenBank Accession Number NM_007332 or NP_015628.2.

Methods of providing suitable test systems are known to the person skilled in the art. For example, a cell based test system can be based on stably transfected cell lines expressing human TRPM8 or TRPA1. Methods of producing suitable test systems are disclosed, inter alia, in Behrendt H J et al., Br. J. Pharmacol. 2004, 141:737-745, which is enclosed herein by reference. According to an optional embodiment, the functional cell based assay utilizes human HEK293 cells recombinantly expressing human TRPM8 or TRPA1. Agonistic or antagonistic action of a compound can be quantified via a $Ca^{2+}$-sensitive dye (such as FURA, Fluo-4, etc.), wherein agonists produce an increase of intracellular calcium ions and antagonists inhibit an increase of intracellular calcium ions (e.g., triggered by endogenous ligands). Such assays are routine and well known to the person skilled in the art.

According to an optional embodiment of the present invention, a compound library comprising suitable compounds is tested in a screening for agonistic and/or antagonistic activity towards TRPM8 and/or other channels. Optionally, compounds can be selected as development candidates, which compounds are agonists or partial agonists of TRPM8 in cells expressing the channel, but do substantially not exhibit agonist activity at another channel, such as TRPA1, or at least to a lesser extend. Optionally, the compounds can further be analyzed with regard to their $EC_{50}$ values as well as their efficacy values and/or can be analyzed in a structure-action relationship. Such screening methods are routine and well known to the person skilled in the art.

According to an embodiment, the present invention further encompasses compounds which are identified in such a screening as development candidates.

Embodiments of the Invention

The present invention relates to compounds which are capable of producing a cooling sensation when they are brought into contact with the human body. Such compounds have applications in many fields, for example in oral and personal hygiene products and foodstuffs, but also in cosmetics, pharmaceutical composition products, textile products and packaging products.

As discussed above, a known compound for producing a sensation of cold is menthol (2-isopropyl-5-methyl-cyclohexanol), which has been extensively applied as an additive in, for example, foodstuffs and oral hygiene products (see e.g. http://www.leffingwell.com/menthol1/menthinfo.htm; Fuffer S M et al., Chem. Percept. 2008, 1(2):119-126). It is used primarily because it elicits a sensation of coolness in the mouth, and because it has a pleasing mint flavour and odour. The cooling effect of menthol is due to the action of menthol as activating the TRPM8 ligand on sensory/free nerve endings which detect thermal stimuli. Without wishing to be bound by any theory, menthol is believed to activate cold receptors on nerve endings. However, the use of menthol is limited by its strong minty smell which is undesirable for some applications and its relative volatility and burning sensations at high concentrations through unintentional activation of other TRPs/ion channels.

It was found that icilin was capable of producing the same cooling effect as menthol. Icilin has a number of advantages over menthol, for example it is more potent, and has a lower acute toxicity, due to its lack of anaesthetic properties. Icilin was considered to be a particularly useful compound for pharmacological applications because it lacks the flavour and odour of menthol and is not readily absorbed through the skin (see e.g. US 2006/0280697 A1 and WO 03/092697 A1).

The compounds and compositions disclosed in the present invention have the ability to produce a cooling sensation when in contact with the skin and/or mucosal membrane of a human or animal body. The term "cooling sensation", as used herein, is thus intended to mean any sensation of coolness which is perceived by human or animal body. Such a cooling sensation is analogous to the sensation produced by compounds such as menthol, and/or the sensation elicited when cold-sensitive receptors, in particular TRPM8, are stimulated.

A cooling sensation is desirable in many different applications. For example, the compounds and compositions of the invention have applications in a number of products, such as cosmetic product compositions, food product compositions, textile products, pharmaceutical product compositions and packaging products.

In an embodiment, the present invention relates to a product comprising a compound that, optionally selectively, modulates the TRPM8 channel (e.g. as evaluated in a functional cell based assay under standard conditions as described herein), and wherein the product is selected from the group consisting of a cosmetic product composition, a food product composition, a textile product, a pharmaceutical product composition and a packaging product. It is understood that such products can comprise any combination of compounds as described herein above, and optionally can also comprise further cooling agents.

In a further embodiment, the present invention relates to a product comprising a compound that exhibits selective agonist activity at the TRPM8 channel (e.g. as evaluated in a functional cell based assay under standard conditions as described herein), and wherein the product is selected from the group consisting of a cosmetic product composition, a food product composition, a textile product, a pharmaceutical product composition and a packaging product.

In a further embodiment, the present invention relates to a product comprising a compound that acts as a selective TRPM8 agonist or partial agonist (e.g. as evaluated in a functional cell based assay under standard conditions as described herein), and wherein the product is selected from the group consisting of a cosmetic product composition, a food product composition, a textile product, a pharmaceutical product composition and a packaging product.

In a further embodiment, the present invention relates to a product comprising an effective amount of a compound that acts as a selective TRPM8 agonist or partial agonist (e.g. as evaluated in a functional cell based assay under standard conditions as described herein), and wherein the product is selected from the group consisting of a cosmetic product composition, a food product composition, a textile product, a pharmaceutical product composition and a packaging product.

In a further embodiment, the present invention relates to a product comprising a compound that exhibits an activity at TRPM8, which activity is at least three times or even at least four times, greater than the activity of the compound at TRPA1 (e.g. as evaluated in a functional cell based assay under standard conditions as described herein), and wherein the product is selected from the group consisting of a cosmetic product composition, a food product composition, a textile product, a pharmaceutical product composition and a packaging product.

In a further embodiment, the present invention relates to a product selected from the group consisting of a cosmetic product composition, a food product composition, a textile product, a pharmaceutical product composition and a packaging product, which product comprises a compound selected from the group consisting of Compounds I, II, III, IV, V, VI, VII, I.1, II.1, III.1, IV.1, V.1, VI.1, VII.1, I.2, II.2, III.2, IV.2, V.2, VI.2, VII.2, I.3, II.3, III.3, IV.3, V.3, VI.3, and VII.3, wherein the Compounds have the chemical structures as defined herein above.

In a further embodiment, the present invention relates to a product selected from the group consisting of a cosmetic product composition, a food product composition, a textile product, a pharmaceutical product composition and a packaging product, which product comprises a compound selected from the group consisting of Compounds I.1, II.1, III.1, IV.1, V.1, VI.1, VII.1, I.2, II.2, III.2, IV.2, V.2, VI.2, VII.2, I.3, II.3, III.3, IV.3, V.3, VI.3, and VII.3, wherein the Compounds have the chemical structures as defined herein above.

In a further embodiment, the present invention relates to a product selected from the group consisting of a cosmetic product composition, a food product composition, a textile product, a pharmaceutical product composition and a packaging product, which product comprises a compound selected from the group consisting of Compounds I.2, II.2, III.2, IV.2, V.2, VI.2, VII.2, I.3, II.3, III.3, IV.3, V.3, VI.3, and VII.3, wherein the Compounds have the chemical structures as defined herein above.

In a further embodiment, the present invention relates to a product selected from the group consisting of a cosmetic product composition, a food product composition, a textile product, a pharmaceutical product composition and a packaging product, which product comprises a compound selected from the group consisting of Compounds I.3, II.3, III.3, IV.3, V.3, VI.3, and VII.3, wherein the Compounds have the chemical structures as defined herein above.

In a further embodiment, the present invention relates to a compound selected from the group consisting of Compounds I, II, III, IV, V, VI, VII, I.1, II.1, III.1, IV.1, V.1, VI.1, VII.1, I.2, II.2, III.2, IV.2, V.2, VI.2, VII.2, I.3, II.3, III.3, IV.3, V.3, VI.3, and VII.3, wherein the Compounds have the chemical structures as defined herein above. In a further embodiment, the present invention relates to a compound selected from the group consisting of Compounds I.1, II.1, III.1, IV.1, V.1, VI.1, VII.1, I.2, II.2, III.2, IV.2, V.2, VI.2, VII.2, I.3, II.3, III.3, IV.3, V.3, VI.3, and VII.3, wherein the Compounds have the chemical structures as defined herein above. In a further embodiment, the present invention relates to a compound selected from the group consisting of Compounds I.2, II.2, III.2, IV.2, V.2, VI.2, VII.2, I.3, II.3, III.3, IV.3, V.3, VI.3, and VII.3, wherein the Compounds have the chemical structures as defined herein above. In a further embodiment, the present invention relates to a compound selected from the group consisting of Compounds I.2, II.2, III.2, IV.2, V.2, VI.2, VII.2, I.3, II.3, III.3, IV.3, V.3, VI.3, and VII.3, wherein the Compounds have the chemical structures as defined herein above. In a further embodiment, the present invention relates to a compound selected from the group consisting of Compounds I.3, II.3, III.3, IV.3, V.3, VI.3, and VII.3, wherein the Compounds have the chemical structures as defined herein above.

Optionally, the compound exhibits an activity at TRPM8, which activity is at least three times, optionally at least four times, five times, seven times, ten times, 12 times, 15 times or 20 times, greater than the activity of the compound at TRPA1 (e.g. as evaluated in a functional cell based assay under standard conditions as described herein).

According to an optional embodiment, the compound acts as a TRPM8 partial agonist or agonist (e.g. as evaluated in a functional cell based assay under standard conditions as described herein). According to an optional embodiment, the compound acts as a selective TRPM8 partial agonist or agonist (e.g. as evaluated in a functional cell based assay under standard conditions as described herein).

According to an optional embodiment, the compound acts as a selective TRPM8 partial antagonist or antagonist (e.g. as evaluated in a functional cell based assay under standard conditions as described herein).

According to a further optional embodiment, in a functional cell based assay the compound modulates the intracellular calcium level of human cells recombinantly expressing human TRPM8 at least four times, five times, seven times, ten times, 12 times, 15 times or 20 times more efficient than that of human cells recombinantly expressing human TRPA1 (e.g. as evaluated in a functional cell based assay under standard conditions as described herein).

According to an optional embodiment of the present invention, the efficacy value of the compound with regard to TRPM8 (compared to 20 µM menthol) is greater than 30%, 40%, 50%, 60%, 70%, 80%, 90%, 100% or 110% (as evaluated in a functional cell based assay under standard conditions as described herein). According to an optional embodiment of the present invention, the $EC_{50}$ value of the compound with regard to TRPM8 (agonistic activity) is less than 20 µM, 15 µM, 12 µM, 10 µM, 8 µM, 6 µM or 4 µM (as evaluated in a functional cell based assay under standard conditions as described herein). According to an optional embodiment of the present invention, the $EC_{50}$ value of the compound with regard to TRPA1 (agonistic activity) is greater than 50 µM, 70 µM, 90 µM, 100 µM, 110 µM, 120 µM or 130 µM (as evaluated in a functional cell based assay under standard conditions as described herein). According to an optional embodiment of the present invention, the $EC_{50}$ value of the compound with regard to TRPM8 (agonistic activity) is about 4 times, 5 times, 7 times, 10 times, 15 times, 20 times, 25 times or 30 times lower than the $EC_{50}$ value of a compound with regard to TRPA1 (agonistic activity) as evaluated in a functional cell based assay under standard conditions as described herein.

Optionally, the compound is selected from the group consisting of Compounds I, II, III, IV, V, VI, VII, I.1, II.1, III.1, IV.1, V.1, VI.1, VII.1, I.2, II.2, III.2, IV.2, V.2, VI.2, VII.2, I.3, II.3, III.3, IV.3, V.3, VI.3, and VII.3, wherein the Compounds have the chemical structures as defined herein above. Optionally, the compound is selected from the group consisting of Compounds I.1, II.1, III.1, IV.1, V.1, VI.1, VII.1, I.2, II.2, III.2, IV.2, V.2, VI.2, VII.2, I.3, II.3, III.3, IV.3, V.3, VI.3, and VII.3, wherein the Compounds have the chemical structures as defined herein above. Optionally, the compound is selected from the group consisting of Compounds I.2, II.2, III.2, IV.2, V.2, VI.2, VII.2, I.3, II.3, III.3, IV.3, V.3, VI.3, and VII.3, wherein the Compounds have the chemical structures as defined herein above. Optionally, the compound is selected from the group consisting of Compounds I.3, II.3, III.3, IV.3, V.3, VI.3, and VII.3, wherein the Compounds have the chemical structures as defined herein above.

In one further embodiment, the present invention relates to the use of a compound as defined herein above in a product selected from the group consisting of a cosmetic product composition, a food product composition, a textile product, a pharmaceutical product composition, and a packaging product. In one further embodiment, the present invention relates to a compound as defined herein above for use in therapy. In one further embodiment, the present invention relates to a compound as defined herein above for use in the treatment of pain. In one further embodiment, the present invention relates to an in vitro use of a compound as defined herein above as cooling agent. In one further embodiment, the present invention relates to a cosmetic use of a compound as defined herein above as cooling agent. In one further embodiment, the present invention relates to an in vitro method of modulating the cold and menthol receptor TRPM8, wherein TRPM8 is contacted with a compound as defined herein above.

In the context of the present invention, the phrase "effective amount", when used in connection with a compound of the invention, means an amount effective for: (a) treating or preventing a condition; or (b) detectably activating TRPM8 function in a cell (as evaluated in a functional cell based assay under standard conditions as described herein). The terms "modulate", "modulating", and the like as used herein with respect to TRPM8 or TRPA1 mean the mediation of a pharmacodynamic response in a cell from (i) inhibiting or activating the respective channel, or (ii) directly or indirectly affecting the normal regulation of the channel activity (e.g., as evaluated in a functional cell based assay under standard conditions as described herein). Compounds that modulate the channel activity include agonists, partial agonists, antagonists, mixed agonists/antagonists, mixed partial agonists/antagonists and compounds which directly or indirectly affect regulation of the channel activity (as evaluated in a functional cell based assay under standard conditions as described herein).

The terms "selective modulation", "selectively modulate", and the like as used herein with respect to TRPM8 or TRPA1 mean the mediation of a pharmacodynamic response in a cell from (i) inhibiting or activating the respective channel (in particular, TRPM8) without substantially triggering another channel (in particular, TRPA1), or (ii) directly or indirectly affecting the normal regulation of the activity of the respective channel (in particular, TRPM8) without substantially affecting the normal regulation of the activity of another channel (in particular, TRPA1) (e.g., as evaluated in a functional cell based assay under standard conditions as described herein).

The terms "selective modulation of TRPM8", "selectively modulate TRPM8", and the like as used herein with respect to TRPM8 mean the mediation of a pharmacodynamic response in a cell from (i) inhibiting or activating TRPM8 without substantially triggering TRPA1 (or at least to a lesser extend), or (ii) directly or indirectly affecting the normal regulation of the activity of TRPM8 without substantially affecting the normal regulation of the activity of TRPA1 (e.g., as evaluated in a functional cell based assay under standard conditions as described herein).

As used herein, a compound disclosed herein that binds to a channel and mimics the regulatory effect(s) of an endogenous ligand is defined as an "agonist" (e.g., as evaluated in a functional cell based assay under standard conditions as described herein). As used herein, a compound that binds to a channel and is only partly effective as an agonist is defined as a "partial agonist" (e.g., as evaluated in a functional cell based assay under standard conditions as described herein). As used herein, a compound that binds to a channel but produces no regulatory effect, but rather blocks binding of another agent to the channel or blocks the functional modulation of the channel by another agent is defined as an "antagonist" or "silent agonist" (i.e. a compound with no efficacy but binding capacity). For an overview of drug binding mechanisms see: Ross and Kenakin, *Pharmacodynamics: Mechanisms of Drug Action and the Relationship Between Drug Concentration and Effect,* Chapter 2 in *Goodman & Gilman's The Pharmacological Basis of Therapeutics* 31-32 (J. G. Hardman, L. E. Limbird and A. Goodman-Gilman eds., 10$^{th}$ ed 2001).

In the context of the present invention, the phrases "selective agonist" or "exhibit selective agonist activity" and the like, when used in connection with a compound of the invention, mean a compound disclosed herein that binds to a channel (in particular, TRPM8) and mimics the regulatory effect(s) of an endogenous ligand (e.g., as evaluated in a functional cell based assay under standard conditions as described herein), but does not substantially activate further channels (in particular, TRPA1), or at least to a lesser extend.

In the context of the present invention, the phrases "selective TRPM8 partial agonist or agonist" or "exhibit selective agonist activity at TRPM8" and the like, when used in connection with a compound of the invention, means a compound that binds to TRPM8 and mimics the regulatory effect(s) of an endogenous ligand (e.g., as evaluated in a functional cell based assay under standard conditions as described herein), but does not substantially activate TRPA1, or at least to a lesser extend.

In the context of the present invention, the phrase "antagonist" or "silent agonist", when used in connection with a compound of the invention, means a compound according to the invention that binds to a channel (in particular, TRPM8) and produces no regulatory effect, but rather blocks binding of another agent to the channel or blocks the functional modulation of the channel by another agent such as an endogenous ligand, e.g., as evaluated in a functional cell based assay under standard conditions as described herein.

The term "exhibit activity on TRPM8" and the like as used herein with respect to TRPM8 mean the agonist activity (if the compound acts as agonist) or inhibitory activity (if the compound acts as antagonist) at TRPM8, as can be evaluated in a functional cell based assay under standard conditions as described herein. Optionally, the term "exhibit activity at TRPM8" and the like as used herein with respect to TRPM8 mean the agonist activity at TRPM8, as can be evaluated in a functional cell based assay under standard conditions as described herein.

As used herein, a functional cell based assay under standard conditions means evaluating the cellular activity of compounds with regard to the modulation of the intracellular calcium level using cells recombinantly expressing human TRPM8 or human TRPA1. In particular, in this context the term "standard conditions" means an activity test using HEK293 cells recombinantly expressing either human TRPM8 or human TRPA1, which cells have been contacted with a calcium-sensitive dye (such as Fluo-4AM, i.e. Fluo-4-acetoxymethylester), wherein the cells are incubated with the compound to be tested, and receptor modulation is quantitatively detected by calcium-dependent changes is fluorescence intensity. Such a test system is disclosed, inter alia, in Behrendt H J et al., Br. J. Pharmacol. 2004, 141: 737-745, which is enclosed herein by reference.

According to an optional embodiment, the cosmetic product composition is selected from the group consisting of an insect repellent composition, an oral hygiene composition, a skin care composition, and a hair care composition. Personal hygiene applications such as skin care compositions and hair care compositions include lotions, shaving cream, post shaving preparations, shampoos, conditioners, facial cleansers, soaps, bath oils and foams, antiperspirants, deodorants. Oral hygiene applications include toothpastes, mouthwashes, dental floss, chewing gum and breath fresheners.

According to an optional embodiment, the food product composition is selected from the group consisting of ice cream, mousse, creme, beverages and confectionery. According to an optional embodiment, the textile product is selected from the group consisting of shirts, trousers, socks, towels, headgear, underwear and shoes. According to an optional embodiment, the pharmaceutical product composition is selected from the group consisting of anticancer medicaments, bladder disease medicaments and medicaments for the treatment of pain.

It is known in the art that modulators of TRPM8 (including its insect analoga) can act as insect repellent, can have an activity in the treatment of tumor (e.g., prostate tumors), can have an activity in the treatment of inflammatory pain/hyperalgesia, and can act as TRPM8 antagonists in the treatment of bladder syndrome or an hyperactive bladder (cf. WO 2010/026094).

Accordingly, the present invention further relates to a compound as defined herein above for use as insect repellent. The present invention further relates to a compound as defined herein above for use in the treatment of cancer, in particular prostate cancer. The present invention further relates to a compound as defined herein above for use in the treatment of inflammatory pain or hyperalgesia. The present invention further relates to a compound as defined herein above for use in the treatment of bladder syndrome or hyperactive bladder.

A cooling sensation can be desirable in packaging products, wherein such cooling sensation is particularly detected upon contact with the content of such packaging products (which can comprise different materials such as paper or plastics). Compounds according to the present invention may be associated with the packaging product material in various ways, e.g., by spin coating, printing, micro capsules, direct incorporation into the material (e.g. extrusion), covalent binding to molecules of the packaging material etc. Suitable methods are known to the person skilled in the art.

A cooling sensation can also be desirable in textile products, wherein such cooling sensation is particularly detected by wearing such products. Compounds according to the present invention may be associated with the textile product material in various ways, e.g., by spin coating, printing, micro capsules, direct incorporation into the material (e.g. extrusion), covalent binding to molecules of the packaging material etc. Suitable methods are known to the person skilled in the art.

The specific nature of the products and compositions of the present invention (e. g. the nature of the additional components, the relative proportions of the components and the physical nature of the composition) will depend on the particular application and are known to the skilled person.

While the above invention has been described with respect to some of its preferred embodiments, this is in no way to limit the scope of the invention. The person skilled in the art is clearly aware of further embodiments and alterations to the previously described embodiments that are still within the scope of the present invention.

EXAMPLES

A screening for novel modulators of TRPM8 was conducted. For the screening, a routine screening setup was used. In particular, the compounds comprised by a compound library were tested for agonistic activity towards TRPM8 and a dose response analysis of the most promising candidates was conducted (TRPM8 versus TRPA1). In particular, promising candidates were analyzed with regard to their $EC_{50}$ values as well as their efficacy values, and 7 development candidates were selected (i.e. Compounds I.3, II.3, III.3, IV.3, V.3, VI.3, and VII.3, as described herein above).

The IUPAC names of the compounds are as follows:
I.3=7-methoxy-2-methyl-3-phenyl-4H-chromen-4-one
II.3=2-{[(2,5-dimethoxyphenyl)amino]methylidene}-5,5-dimethylcyclohexane-1,3-dione
III.3=3-(5-methylthiophen-2-yl)-N'-[(1E)-pyridin-4-ylmethylidene]-1H-pyrazole-5-carbohydrazide
IV.3=N-(2,5-dichlorophenyl)-2-[(6-oxo-4-propyl-1,6-dihydropyrimidin-2-yl)sulfanyl]acetamide
V.3=1-[4-(2H-1,3-benzodioxol-5-ylmethyl)piperazin-1-yl]-3-(2-methyl-1H-1,3-benzodiazol-1-yl)propan-1-one
VI.3=4-methyl-N-[(4-phenyloxan-4-yl)methyl]benzamide
VII.3=[3-(4-chlorophenyl)-4-methylpentyl][3-(dimethylamino)propyl]amine These compounds are commercially available at, e.g., InterBioScreen Ltd. (Moscow, Russia), Vitas-M Laboratory Ltd. (Moskow, Russia) or Princeton BioMolecular Research. Inc. (Princeton, N.J., USA).

For the above analysis, a functional cell based assay under standard conditions as described herein was used, i.e. the cellular activity of the compounds with regard to the modulation of the intracellular calcium level was evaluated using cells recombinantly expressing human TRPM8 or human TRPA1. In particular, human cells recombinantly expressing either human TRPM8 or human TRPA1 were used, which cells have been contacted with a calcium-sensitive dye, wherein the cells were incubated with the compound to be tested, and receptor modulation was quantitatively detected by calcium-dependent changes in fluorescence intensity. Such a test system is disclosed, inter alia, in Behrendt H J et al., Br. J. Pharmacol. 2004, 141:737-745, which is enclosed herein by reference. Such a test system is also disclosed, inter alia, in WO 2010/026094, which is also enclosed herein by reference. However, it should be understood that any screening method and method suitable for evaluating the agonistic activity of compounds towards a channel (such as TRPM8) can be used. Suitable methods are routine and known to the skilled person.

The dose response analysis of the 7 development candidates are depicted in FIGS. 1-7 and summarized in Table 2.

TABLE 2

| Compound | $EC_{50}$ (TRPM8) (in µM) | $EC_{50}$ (TRPA1) (in µM) | Efficacy for TRPM8 activation (in %) (compared to 20 µM menthol) |
|---|---|---|---|
| I.3 | 2.01 | 72.42 | 110.06 |
| II.3 | 8.01 | 123.22 | 46.59 |
| III.3 | 5.27 | 113.40 | 97.65 |
| IV.3 | 4.12 | 117.89 | 34.14 |
| V.3 | 7.53 | 138.37 | 70.90 |
| VI.3 | 8.15 | 107.64 | 95.36 |
| VII.3 | 10.94 | 56.62 | 45.12 |

The invention claimed is:
1. A method of producing a cooling sensation, the method comprising contacting skin and/or a mucosal membrane of a human or animal with an effective amount of a Compound I.2 having the following general formula:

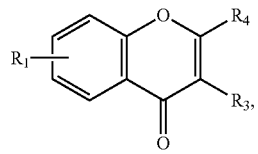

or a pharmaceutically acceptable derivative thereof, wherein:
$R_1$ is —H, —$OT_3$, -$ST_3$, or —($C_1$-$C_3$)alkyl, and wherein $T_3$ is —H or —($C_1$-$C_2$)alkyl;
$R_3$ is phenyl, pyridinyl, pyrazinyl, pyridazinyl or pyrimidinyl, each of which is unsubstituted or substituted with 1 or 2 moieties independently selected from $R_6$;
$R_4$ is —($C_1$-$C_3$)alkyl, —($C_2$-$C_3$)alkenyl, —($C_2$-$C_3$)alkynyl, or —($C_1$-$C_3$)alkoxy; and
$R_6$ is —H, —($C_1$-$C_2$)alkyl, —($C_2$)alkenyl, —($C_2$)alkynyl, —$OR_7$, —$SR_7$, —C(halo)$_3$, —CH(halo)$_2$, —$CH_2$(halo), —CN, -halo, —$N_3$, —$NO_2$, —N($R_7$)$_2$, —N($R_7$)OH, —C(=O)$R_7$, —C(=O)$OR_7$, —S(=O)$R_7$, or —S(=O)$_2R_7$;
each $R_7$ is independently —H, or —$CH_3$; and
each halo is independently —F, —Cl, —Br, or —I,
to produce the cooling sensation.

2. The method of claim 1, wherein the Compound I.2, or a pharmaceutically acceptable derivative thereof, exhibits selective agonist activity at TRPM8.

3. The method of claim 1, wherein the Compound I.2, or a pharmaceutically acceptable derivative thereof, exhibits activity at TRPM8, wherein the activity is at least three times, or even at least four times, greater than the activity of the Compound I.2, or a pharmaceutically acceptable derivative thereof, at TRPA1.

4. The method of claim 3, wherein in a functional cell-based assay the Compound I.2, or a pharmaceutically acceptable derivative thereof, modulates the intracellular calcium level of human cells recombinantly expressing human TRPM8 at least four times more efficiently than that of human cells recombinantly expressing human TRPA1.

5. The method of claim 1, wherein the Compound I.2, or a pharmaceutically acceptable derivative thereof, is comprised in a product selected from the group consisting of a cosmetic product composition, a food product composition, a textile product, a pharmaceutical product composition and a packaging product.

6. The method of claim 5, wherein:
the cosmetic product composition is selected from the group consisting of an oral hygiene composition, a skin care composition, and a hair care composition; or
the food product composition is selected from the group consisting of ice cream, mousse, crème, beverages and confectionery; or
the textile product is selected from the group consisting of shirts, trousers, socks, towels, headgear, underwear and shoes; or
the pharmaceutical product composition is selected from the group consisting of anticancer medicaments, bladder disease medicaments and medicaments for the treatment of pain.

7. The method of claim 1, wherein the Compound I.2, or a pharmaceutically acceptable derivative thereof, is Compound I.3 having the following chemical structure:

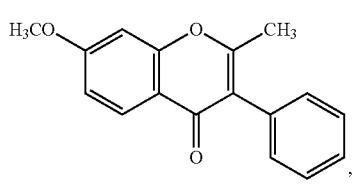

or a pharmaceutically acceptable derivative thereof.

8. The method of claim 7, wherein the Compound I.3, or a pharmaceutically acceptable derivative thereof, is comprised in a product selected from the group consisting of a cosmetic product composition, a food product composition, a textile product, a pharmaceutical product composition and a packaging product.

9. The method of claim 8, wherein:
the cosmetic product composition is selected from the group consisting of an oral hygiene composition, a skin care composition, and a hair care composition; or
the food product composition is selected from the group consisting of ice cream, mousse, crème, beverages and confectionery; or
the textile product is selected from the group consisting of shirts, trousers, socks, towels, headgear, underwear and shoes; or
the pharmaceutical product composition is selected from the group consisting of anticancer medicaments, bladder disease medicaments and medicaments for the treatment of pain.

* * * * *